(12) United States Patent
Jiang et al.

(10) Patent No.: US 10,723,805 B2
(45) Date of Patent: *Jul. 28, 2020

(54) ANTIBODIES SPECIFIC FOR CLL-1

(71) Applicant: Cellerant Therapeutics, Inc., San Carlos, CA (US)

(72) Inventors: Ping Jiang, Lafayette, CA (US); Holger Karsunky, Redwood City, CA (US); Rob Tressler, Soquel, CA (US)

(73) Assignee: Cellerant Therapeutics, Inc., Newark, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/853,056

(22) Filed: Dec. 22, 2017

(65) Prior Publication Data

US 2018/0273633 A1 Sep. 27, 2018

Related U.S. Application Data

(63) Continuation of application No. 14/853,881, filed on Sep. 14, 2015, now Pat. No. 9,850,314, which is a continuation of application No. 13/794,525, filed on Mar. 11, 2013, now Pat. No. 9,163,090.

(60) Provisional application No. 61/643,739, filed on May 7, 2012, provisional application No. 61/699,134, filed on Sep. 10, 2012.

(51) Int. Cl.
| *A61K 39/395* | (2006.01) |
| *A61K 39/00* | (2006.01) |
| *C07K 16/30* | (2006.01) |
| *A61K 47/68* | (2017.01) |
| *C07K 16/28* | (2006.01) |
| *G01N 33/574* | (2006.01) |

(52) U.S. Cl.
CPC ...... *C07K 16/3061* (2013.01); *A61K 47/6819* (2017.08); *A61K 47/6849* (2017.08); *C07K 16/2851* (2013.01); *G01N 33/57492* (2013.01); *A61K 2039/505* (2013.01); *C07K 2317/24* (2013.01); *C07K 2317/33* (2013.01); *C07K 2317/56* (2013.01); *C07K 2317/565* (2013.01); *C07K 2317/732* (2013.01); *C07K 2317/734* (2013.01); *C07K 2317/92* (2013.01); *G01N 2333/705* (2013.01); *G01N 2333/70596* (2013.01)

(58) Field of Classification Search
None
See application file for complete search history.

(56) References Cited

U.S. PATENT DOCUMENTS

| 7,741,443 | B2 | 6/2010 | Van Den Oudenrijn et al. |
| 8,536,310 | B2 | 9/2013 | Abo et al. |
| 9,163,090 | B2 * | 10/2015 | Jiang ............... C07K 16/3061 |
| 9,850,314 | B2 * | 12/2017 | Jiang ............... C07K 16/3061 |
| 2006/0177451 | A1 | 8/2006 | Van Den Oudenrijn et al. |
| 2009/0324491 | A1 | 12/2009 | Aburatani et al. |
| 2010/0285037 | A1 | 11/2010 | Abo et al. |
| 2011/0201104 | A1 | 8/2011 | Lee et al. |
| 2011/0291112 | A1 | 12/2011 | Sankin et al. |

FOREIGN PATENT DOCUMENTS

| WO | 2009-051974 A1 | 4/2009 |
| WO | 2011/070109 A1 | 6/2011 |

OTHER PUBLICATIONS

Rhenen et al. The novel AML stem cell-associated antigen CLL-1 aids in discrimination between normal and leukemic stem cells. Blood. 2007; 110:2659-2666. (Year: 2007).*
The International Search Report and Written Opinion from PCT/US2013/039645, dated Sep. 20, 2013.
Zhao et al.; "Targeting C-type lectin-like molecule-1 for antibody-mediated immunotherapy in acute myeloid leukemia"; *haematologica*; 95(1):71-78 (2010).
Bakker et al., "C-Type Lectin-Like Molecule-1: A Novel Myeloid Cell Surface Marker Associated with Acute Myeloid Leukemia", *Cancer Res.*, 64:8443-8450 (Nov. 2004).
Redelinghuys et al., "Inhibitory C-type lectin receptors in myeloid cells," *Immunol. Lett.*, 136(1): 1-12 (Apr. 2011).
Van Rhenen et al., The novel AML stem cell associated antigen CLL-1 cells, *Blood*, 110(7):2659-2666 (Oct. 2007).
M. H. Lahoud et al.: "The C-Type Lectin Clec12A Present on Mouse and Human Dendritic Cells Can Serve as a Target for Antigen Delivery and Enhancement of Antibody Responses", The Journal of Immunology, val. 182, No. 12, Jun. 3, 2009 (Jun. 3, 2009), pp. 7587-7594.
Andrews J. Marshall et al.: "Human MICL (CLEC12A) is differentially glycosylated and is down-regulated following cellular activation", European Journal of Immunology, vol. 36, No. 8, Aug. 1, 2006 (Aug. 1, 2006 ), pp. 2159-2169.
European Search Report dated Dec. 16, 2015 in European Patent Application No. 137873816, all pages.

* cited by examiner

*Primary Examiner* — Maher M Haddad
(74) *Attorney, Agent, or Firm* — Kilpatrick Townsend & Stockton LLP

(57) ABSTRACT

Provided herein are antibodies specific for CLL-1.

11 Claims, 11 Drawing Sheets

Specification includes a Sequence Listing.

SEQUENCE LISTING

```
<160> NUMBER OF SEQ ID NOS: 98

<210> SEQ ID NO 1
<211> LENGTH: 801
<212> TYPE: DNA
<213> ORGANISM: Homo sapiens
<220> FEATURE:
<223> OTHER INFORMATION: human C-type lectin-like molecule 1 (CLL-1),
      C-type lectin domain family 12 member A (CLEC12A), dendritic
      cell-associated lectin 2 (DCAL-2), myeloid inhibitory C-type
      lectin-like receptor (MICL), C-type lectin protein

<400> SEQUENCE: 1
atgtctgaag aagttactta tgcagatctt caattccaga actccagtga gatggaaaaa      60
atcccagaaa ttggcaaatt tggggaaaaa gcacctccag ctccctctca tgtatggcgt     120
ccagcagcct tgtttctgac tcttctgtgc cttctgttgc tcattggatt gggagtcttg     180
gcaagcatgt ttcatgtaac tttgaagata gaaatgaaaa aaatgaacaa actacaaaac     240
atcagtgaag agctccagag aaatatttct ctacaactga tgagtaacat gaatatctcc     300
aacaagatca ggaacctctc caccacactg caaacaatag ccaccaaatt atgtcgtgag     360
ctatatagca aagaacaaga gcacaaatgt aagccttgtc caaggagatg gatttggcat     420
aaggacagct gttatttcct aagtgatgat gtccaaacat ggcaggagag taaaatggcc     480
tgtgctgctc agaatgccag cctgttgaag ataaacaaca aaaatgcatt ggaatttata     540
aaatcccaga gtagatcata tgactattgg ctgggattat ctcctgaaga agattccact     600
cgtggtatga gagtggataa tataatcaac tcctctgcct gggttataag aaacgcacct     660
gacttaaata acatgtattg tggatatata aatagactat atgttcaata ttatcactgc     720
acttataaac aaagaatgat atgtgagaag atggccaatc cagtgcagct tggttctaca     780
tattttaggg aggcatgagg c                                              801

<210> SEQ ID NO 2
<211> LENGTH: 265
<212> TYPE: PRT
<213> ORGANISM: Homo sapiens
<220> FEATURE:
<223> OTHER INFORMATION: human C-type lectin-like molecule 1 (CLL-1),
      C-type lectin domain family 12 member A (CLEC12A), dendritic
      cell-associated lectin 2 (DCAL-2), myeloid inhibitory C-type
      lectin-like receptor (MICL), C-type lectin protein
<220> FEATURE:
<221> NAME/KEY: DOMAIN
<222> LOCATION: (1)...(43)
<223> OTHER INFORMATION: cytoplasmic domain
<220> FEATURE:
<221> NAME/KEY: DOMAIN
<222> LOCATION: (44)...(64)
<223> OTHER INFORMATION: transmembrane domain
<220> FEATURE:
<221> NAME/KEY: DOMAIN
<222> LOCATION: (65)...(139)
<223> OTHER INFORMATION: stalk domain
<220> FEATURE:
<221> NAME/KEY: DOMAIN
```

```
<222> LOCATION: (140)...(249)
<223> OTHER INFORMATION: C lectin domain
<220> FEATURE:
<221> NAME/KEY: DOMAIN
<222> LOCATION: (65)...(265)
<223> OTHER INFORMATION: extracellular domain

<400> SEQUENCE: 2

Met Ser Glu Glu Val Thr Tyr Ala Asp Leu Gln Phe Gln Asn Ser Ser
1               5                   10                  15

Glu Met Glu Lys Ile Pro Glu Ile Gly Lys Phe Gly Glu Lys Ala Pro
            20                  25                  30

Pro Ala Pro Ser His Val Trp Arg Pro Ala Ala Leu Phe Leu Thr Leu
        35                  40                  45

Leu Cys Leu Leu Leu Leu Ile Gly Leu Gly Val Leu Ala Ser Met Phe
    50                  55                  60

His Val Thr Leu Lys Ile Glu Met Lys Lys Met Asn Lys Leu Gln Asn
65                  70                  75                  80

Ile Ser Glu Glu Leu Gln Arg Asn Ile Ser Leu Gln Leu Met Ser Asn
                85                  90                  95

Met Asn Ile Ser Asn Lys Ile Arg Asn Leu Ser Thr Thr Leu Gln Thr
            100                 105                 110

Ile Ala Thr Lys Leu Cys Arg Glu Leu Tyr Ser Lys Glu Gln Glu His
        115                 120                 125

Lys Cys Lys Pro Cys Pro Arg Arg Trp Ile Trp His Lys Asp Ser Cys
    130                 135                 140

Tyr Phe Leu Ser Asp Asp Val Gln Thr Trp Gln Glu Ser Lys Met Ala
145                 150                 155                 160

Cys Ala Ala Gln Asn Ala Ser Leu Leu Lys Ile Asn Asn Lys Asn Ala
                165                 170                 175

Leu Glu Phe Ile Lys Ser Gln Ser Arg Ser Tyr Asp Tyr Trp Leu Gly
            180                 185                 190

Leu Ser Pro Glu Glu Asp Ser Thr Arg Gly Met Arg Val Asp Asn Ile
        195                 200                 205

Ile Asn Ser Ser Ala Trp Val Ile Arg Asn Ala Pro Asp Leu Asn Asn
    210                 215                 220

Met Tyr Cys Gly Tyr Ile Asn Arg Leu Tyr Val Gln Tyr Tyr His Cys
225                 230                 235                 240

Thr Tyr Lys Lys Arg Met Ile Cys Glu Lys Met Ala Asn Pro Val Gln
                245                 250                 255

Leu Gly Ser Thr Tyr Phe Arg Glu Ala
            260                 265

<210> SEQ ID NO 3
<211> LENGTH: 360
<212> TYPE: DNA
<213> ORGANISM: Artificial Sequence
<220> FEATURE:
<223> OTHER INFORMATION: synthetic anti-CLL-1 monoclonal antibody M26
      heavy chain coding sequence

<400> SEQUENCE: 3
gaggtccagc tgcagcagtc tggacctgag ctggtaaagc ctggggcttc agtgaagatg      60
tcctgcaagg cttctggata cacattcact agctatttta tacactgggt gaagcagaag    120
cctggacagg gccttgagtg gattggattt attaatcctt acaatgatgg ttctaagtac    180
aatgagaagt tcaaaggcaa ggccacactg acttcagaca atcctccag cacagcctac    240
```

```
atggagctca gcagcctgac ctctgaagac tcagcggtct attactgtac aagagatgat    300
ggttattacg ctatgctat ggactactgg ggtcaaggaa cctcagtcac cgtctcctca    360
```

<210> SEQ ID NO 4
<211> LENGTH: 120
<212> TYPE: PRT
<213> ORGANISM: Artificial Sequence
<220> FEATURE:
<223> OTHER INFORMATION: synthetic anti-CLL-1 monoclonal antibody M26
      heavy chain

<400> SEQUENCE: 4

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Phe Ile His Trp Val Lys Gln Lys Pro Gly Gln Gly Leu Glu Trp Ile
        35                  40                  45

Gly Phe Ile Asn Pro Tyr Asn Asp Gly Ser Lys Tyr Asn Glu Lys Phe
    50                  55                  60

Lys Gly Lys Ala Thr Leu Thr Ser Asp Lys Ser Ser Thr Ala Tyr
65                  70                  75                  80

Met Glu Leu Ser Ser Leu Thr Ser Glu Asp Ser Ala Val Tyr Tyr Cys
                85                  90                  95

Thr Arg Asp Asp Gly Tyr Tyr Gly Tyr Ala Met Asp Tyr Trp Gly Gln
            100                 105                 110

Gly Thr Ser Val Thr Val Ser Ser
        115                 120

<210> SEQ ID NO 5
<211> LENGTH: 323
<212> TYPE: DNA
<213> ORGANISM: Artificial Sequence
<220> FEATURE:
<223> OTHER INFORMATION: synthetic anti-CLL-1 monoclonal antibody M26
      light chain coding sequence

<400> SEQUENCE: 5

```
gacatccaga tgacccagtc tccatcctcc ttatctgcct ctctgggaga aagagtcagt    60
ctcacttgtc gggcaactca ggaacttagt ggttacttaa gctggcttca gcagaaacca    120
gatggaacta ttaaacgcct gatctacgcc gcatccactt tagattctgg tgtcccaaaa    180
aggttcagtg caataggtc tgggtcagat tattctctca ccatcagcag ccttgagtct    240
gaagattttg cagactatta ctgtctacaa tatgctattt atccgtacac gttcggaggg    300 ggaccaagc tggaaataaa acg                                             323
```

<210> SEQ ID NO 6
<211> LENGTH: 108
<212> TYPE: PRT
<213> ORGANISM: Artificial Sequence
<220> FEATURE:
<223> OTHER INFORMATION: synthetic anti-CLL-1 monoclonal antibody M26
      light chain

<400> SEQUENCE: 6

Asp Ile Gln Met Thr Gln Ser Pro Ser Ser Leu Ser Ala Ser Leu Gly
1               5                   10                  15

Glu Arg Val Ser Leu Thr Cys Arg Ala Thr Gln Glu Leu Ser Gly Tyr
            20                  25                  30

```
Leu Ser Trp Leu Gln Gln Lys Pro Asp Gly Thr Ile Lys Arg Leu Ile
        35                  40                  45

Tyr Ala Ala Ser Thr Leu Asp Ser Gly Val Pro Lys Arg Phe Ser Gly
 50                  55                  60

Asn Arg Ser Gly Ser Asp Tyr Ser Leu Thr Ile Ser Ser Leu Glu Ser
 65                  70                  75                  80

Glu Asp Phe Ala Asp Tyr Tyr Cys Leu Gln Tyr Ala Ile Tyr Pro Tyr
                 85                  90                  95

Thr Phe Gly Gly Gly Thr Lys Leu Glu Ile Lys Arg
            100                 105

<210> SEQ ID NO 7
<211> LENGTH: 360
<212> TYPE: DNA
<213> ORGANISM: Artificial Sequence
<220> FEATURE:
<223> OTHER INFORMATION: synthetic anti-CLL-1 monoclonal antibody M31
      heavy chain coding sequence

<400> SEQUENCE: 7
gaggtccagc tgcagcagtc tggacctgag ctggtaaagc ctggggcttc agtgaagatg      60
tcctgcaagg cttctggata cacattcacc agctatgtta tgcactgggt gaagcagaag     120
cctgggcagg gccttgagtg gattggatat attaatcctt acaatgatgg tactaagtat     180
aatgagaagt tcaaaggcaa ggccacactg acttcagaca catcctccag cacagcctac     240
atggagctca acagcctgac ctctgaggac tctgcggtct atttctgtgc aagacccatc     300
tactttgata cgactacttt tgactactgg ggccaaggca ccactctcaa agtctcttca     360

<210> SEQ ID NO 8
<211> LENGTH: 120
<212> TYPE: PRT
<213> ORGANISM: Artificial Sequence
<220> FEATURE:
<223> OTHER INFORMATION: synthetic anti-CLL-1 monoclonal antibody M31
      heavy chain

<400> SEQUENCE: 8

Glu Val Gln Leu Gln Gln Ser Gly Pro Glu Leu Val Lys Pro Gly Ala
 1               5                  10                  15

Ser Val Lys Met Ser Cys Lys Ala Ser Gly Tyr Thr Phe Thr Ser Tyr
             20                  25                  30

Val Met His Trp Val Lys Gln Lys Pro Gly Gln Gly Leu Glu Trp Ile
         35                  40                  45

Gly Tyr Ile Asn Pro Tyr Asn Asp Gly Thr Lys Tyr Asn Glu Lys Phe
 50                  55                  60

Lys Gly Lys Ala Thr Leu Thr Ser Asp Thr Ser Ser Ser Thr Ala Tyr
 65                  70                  75                  80

Met Glu Leu Asn Ser Leu Thr Ser Glu Asp Ser Ala Val Tyr Phe Cys
                 85                  90                  95

Ala Arg Pro Ile Tyr Phe Asp Asn Asp Tyr Phe Asp Tyr Trp Gly Gln
            100                 105                 110

Gly Thr Thr Leu Lys Val Ser Ser
        115                 120

<210> SEQ ID NO 9
<211> LENGTH: 334
<212> TYPE: DNA
<213> ORGANISM: Artificial Sequence
<220> FEATURE:
```

<223> OTHER INFORMATION: synthetic anti-CLL-1 monoclonal antibody M31
      light chain coding sequence

<400> SEQUENCE: 9

```
accattgtgc tgacccaatc tccagcttct ttggctgtgt ctctagggca gagggccacc    60
atatcctgca gagccagtga aagtgttgat agttatggca atagttttat gcactggtac   120
cagcagaaac aggacagcc acccaaactc ctcatctatc ttgcatccaa cctagaatct    180
ggggtccctg ccaggttcag tggcagtggg tctaggacag acttcaccct caccattgat   240
cctgtggagg ctgatgatgc tgcaacctat tactgtcaac aaaataatta tgatccgtgg   300
acgttcggtg gaggcaccaa gctggaaatc aaac                                334
```

<210> SEQ ID NO 10
<211> LENGTH: 111
<212> TYPE: PRT
<213> ORGANISM: Artificial Sequence
<220> FEATURE:
<223> OTHER INFORMATION: synthetic anti-CLL-1 monoclonal antibody M31
      light chain

<400> SEQUENCE: 10

```
Thr Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Ala Asp Asp Ala Ala Thr Tyr Tyr Cys Gln Gln Asn Asn
                85                  90                  95

Tyr Asp Pro Trp Thr Phe Gly Gly Gly Thr Lys Leu Glu Ile Lys
            100                 105                 110
```

<210> SEQ ID NO 11
<211> LENGTH: 360
<212> TYPE: DNA
<213> ORGANISM: Artificial Sequence
<220> FEATURE:
<223> OTHER INFORMATION: synthetic anti-CLL-1 monoclonal antibody G4
      heavy chain coding sequence

<400> SEQUENCE: 11

```
gaggtccagc tgcaacagtc tggacctgag ctggtgaagc ctggagcttc aatgaagata    60
tcctgcaagg cttctggtta tcattcact ggctacacca tgaactgggt gaagcagagc    120
catgaaaaga ccttgagtg gattggccct attaatcctt acaatgatgg tactatctac    180
aacccgaact caagggcaa ggccacatta actgtagaca aggcatccag cacagcctac    240
atggagctcc tcagtctgac atctgacgac cctgcagtct attactgtgc cagaacggat    300
gattacgatg attatactat ggactactgg ggtcaaggaa cctcagtcac cgtctcctca   360
```

<210> SEQ ID NO 12
<211> LENGTH: 120
<212> TYPE: PRT
<213> ORGANISM: Artificial Sequence
<220> FEATURE:
<223> OTHER INFORMATION: synthetic anti-CLL-1 monoclonal antibody G4 heavy chain

<400> SEQUENCE: 12

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
            20                  25                  30

Thr Met Asn Trp Val Lys Gln Ser His Glu Lys Asn Leu Glu Trp Ile
        35                  40                  45

Gly Pro Ile Asn Pro Tyr Asn Asp Gly Thr Ile Tyr Asn Pro Asn Phe
    50                  55                  60

Lys Gly Lys Ala Thr Leu Thr Val Asp Lys Ala Ser Ser Thr Ala Tyr
65                  70                  75                  80

Met Glu Leu Leu Ser Leu Thr Ser Asp Asp Pro Ala Val Tyr Tyr Cys
                85                  90                  95

Ala Arg Thr Asp Asp Tyr Asp Asp Tyr Thr Met Asp Tyr Trp Gly Gln
            100                 105                 110

Gly Thr Ser Val Thr Val Ser Ser
        115                 120

<210> SEQ ID NO 13
<211> LENGTH: 322
<212> TYPE: DNA
<213> ORGANISM: Artificial Sequence
<220> FEATURE:
<223> OTHER INFORMATION: synthetic anti-CLL-1 monoclonal antibody G4
      light chain coding sequence

<400> SEQUENCE: 13
gaaatccaga tgacacagac tccatcctcc ctgtctgcct ctctgggaga cagagtcacc      60
atcagttgca gggcaagtca tgacattagc aattatttaa actggtatca gcagaaacca    120
gatggaactc ttaaactcct gatctactac acatcaagac tacactcagg agtcccatca    180
agattcagtg gcagtgggtc tggaacagat tattctctca ccattagcaa cctggagcaa    240
gaagatattg ccacttattt ttgccaacag ggtaaaacgc ttctgtggac gttcggtgga    300
ggcaccaagc tggaaatcaa ac                                              322

<210> SEQ ID NO 14
<211> LENGTH: 107
<212> TYPE: PRT
<213> ORGANISM: Artificial Sequence
<220> FEATURE:
<223> OTHER INFORMATION: synthetic anti-CLL-1 monoclonal antibody G4
      light chain

<400> SEQUENCE: 14

Glu Ile Gln Met Thr Gln Thr Pro Ser Ser Leu Ser Ala Ser Leu Gly
1               5                   10                  15

Asp Arg Val Thr Ile Ser Cys Arg Ala Ser His Asp Ile Ser Asn Tyr
            20                  25                  30

Leu Asn Trp Tyr Gln Gln Lys Pro Asp Gly Thr Leu Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Lys Thr Leu Leu Trp
                85                  90                  95

Thr Phe Gly Gly Gly Thr Lys Leu Glu Ile Lys
            100                 105

<210> SEQ ID NO 15
<211> LENGTH: 363
<212> TYPE: DNA
<213> ORGANISM: Artificial Sequence
<220> FEATURE:
<223> OTHER INFORMATION: synthetic anti-CLL-1 monoclonal antibody M22
      heavy chain coding sequence

<400> SEQUENCE: 15
caggtccaac tgcagcagcc tggggctgag ctggtgaagc ctggggcttc agtgaagctg      60
tcctgtaagg cttctggcta caccttcacc aggtactgga tgcactgggt gaagcagagg     120
cctggacaag gccttgaatg gattggtaat attgacccct ctgatactga aactcactac     180
aatcaacagt tcaaggacaa ggccacattg actgtagaca atcctccag cacagcctac      240 atgcagctca gcagcctgac atctgaggac tctgcggtct attactgtgc aatctactat     300
ggtaacccgt cttactatgc tatggactac tggggtcaag gaacctcagt caccgtctcc     360
tca                                                                   363

<210> SEQ ID NO 16
<211> LENGTH: 121
<212> TYPE: PRT
<213> ORGANISM: Artificial Sequence
<220> FEATURE:
<223> OTHER INFORMATION: synthetic anti-CLL-1 monoclonal antibody M22
      heavy chain

<400> SEQUENCE: 16

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Arg Tyr
            20                  25                  30

Trp Met His Trp Val Lys Gln Arg Pro Gly Gln Gly Leu Glu Trp Ile
        35                  40                  45

Gly Asn Ile Asp Pro Ser Asp Thr Glu Thr His Tyr Asn Gln Gln Phe
    50                  55                  60

Lys Asp Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Ile Tyr Tyr Gly Asn Pro Ser Tyr Tyr Ala Met Asp Tyr Trp Gly
            100                 105                 110

Gln Gly Thr Ser Val Thr Val Ser Ser
        115                 120

<210> SEQ ID NO 17
<211> LENGTH: 340
<212> TYPE: DNA
<213> ORGANISM: Artificial Sequence
<220> FEATURE:
<223> OTHER INFORMATION: synthetic anti-CLL-1 monoclonal antibody M22
      light chain coding sequence

<400> SEQUENCE: 17
gacattgtga tgacacagtc tccatcctcc ctgactgtga cagcaggaga gaaggtcact      60
atgagctgca agtccagtca gaatctgtta aacagtggaa atcaaaagaa atacttgaac     120
tggtaccagc agaaaccagg gcagcctcct aaattgttga tctactgggc atccactagg    180
gaatctgggg tccctgatcg cttcacaggc agtggatctg gaacagattt cactctcacc    240
atcagcagtg tgcaggctga agacctggca gtttatttct gtcagaatga ttatagttat    300
ccgttcacgt tcggtgctgg gaccaagctg gagctgaaac    340

<210> SEQ ID NO 18
<211> LENGTH: 113
<212> TYPE: PRT
<213> ORGANISM: Artificial Sequence
<220> FEATURE:
<223> OTHER INFORMATION: synthetic anti-CLL-1 monoclonal antibody M22
      light chain

<400> SEQUENCE: 18

Asp Ile Val Met Thr Gln Ser Pro Ser Ser Leu Thr Val Thr Ala Gly
1               5                   10                  15

Glu Lys Val Thr Met Ser Cys Lys Ser Ser Gln Asn Leu Leu Asn Ser
            20                  25                  30

Gly Asn Gln Lys Lys Tyr Leu Asn Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Phe Cys Gln Asn
                85                  90                  95

Asp Tyr Ser Tyr Pro Phe Thr Phe Gly Ala Gly Thr Lys Leu Glu Leu
            100                 105                 110

Lys

<210> SEQ ID NO 19
<211> LENGTH: 357
<212> TYPE: DNA
<213> ORGANISM: Artificial Sequence
<220> FEATURE:
<223> OTHER INFORMATION: synthetic anti-CLL-1 monoclonal antibody M29
      heavy chain coding sequence

<400> SEQUENCE: 19
gaggtccagc tgcagcagtc tggacctgag ctggttaagc ctggggcttc agtgaagatg    60
tcctgcaagg cttctggata catattcact agctatgtta tgtactgggt gaagcagaag    120
cctgggcagg gccttgagtg gattggatat attaatcctt acaatgatgg tactaagtac    180
aatgagaagt tcaaaggcaa ggccacactg acttcagaca atcctccag cacagcctac    240 atggagctca gcagcctgac ctctgaggac tctgcggtct attactgtgc aagatactat    300
gattacgact actactttga ctactggggc caaggcacca ctctcacagt ctcctca       357

<210> SEQ ID NO 20
<211> LENGTH: 119
<212> TYPE: PRT
<213> ORGANISM: Artificial Sequence
<220> FEATURE:
<223> OTHER INFORMATION: synthetic anti-CLL-1 monoclonal antibody M29
      heavy chain

<400> SEQUENCE: 20

Glu Val Gln Leu Gln Gln Ser Gly Pro Glu Leu Val Lys Pro Gly Ala
1               5                   10                  15

```
Ser Val Lys Met Ser Cys Lys Ala Ser Gly Tyr Ile Phe Thr Ser Tyr
            20                  25                  30

Val Met Tyr Trp Val Lys Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Tyr Tyr Asp Tyr Asp Tyr Tyr Phe Asp Tyr Trp Gly Gln Gly
            100                 105                 110

Thr Thr Leu Thr Val Ser Ser
            115
```

<210> SEQ ID NO 21
<211> LENGTH: 319
<212> TYPE: DNA
<213> ORGANISM: Artificial Sequence
<220> FEATURE:
<223> OTHER INFORMATION: synthetic anti-CLL-1 monoclonal antibody M29
      light chain coding sequence

<400> SEQUENCE: 21

```
gacatccaga tgacacagtc tccatcctca ctgtctgcat ctctgggagg caaagtcacc    60
atcacttgca aggcaagcca agacattaac aagtatatag cttggtacca acacaagcct   120
ggaaaaggtc ctaggctgct catacattac acatctacat tacagccagg catcccatca   180
aggttcagtg gaagtgggtc tgggagagat tattccttca gcatcagcaa cctggagcct   240
gaagatattg caacttatta ttgtctacag tatgattatc tgtggacgtt cggtggaggc   300
accaagctgg aaatcaaac                                                319
```

<210> SEQ ID NO 22
<211> LENGTH: 106
<212> TYPE: PRT
<213> ORGANISM: Artificial Sequence
<220> FEATURE:
<223> OTHER INFORMATION: synthetic anti-CLL-1 monoclonal antibody M29
      light chain

<400> SEQUENCE: 22

```
Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Lys Tyr
            20                  25                  30

Ile Ala Trp Tyr Gln His Lys Pro Gly Lys Gly Pro Arg Leu Leu Ile
        35                  40                  45

His Tyr Thr Ser Thr Leu Gln Pro Gly Ile Pro Ser Arg Phe Ser Gly
    50                  55                  60

Ser Gly Ser Gly Arg Asp Tyr Ser Phe Ser Ile Ser Asn Leu Glu Pro
65                  70                  75                  80

Glu Asp Ile Ala Thr Tyr Tyr Cys Leu Gln Tyr Asp Tyr Leu Trp Thr
                85                  90                  95

Phe Gly Gly Gly Thr Lys Leu Glu Ile Lys
            100                 105
```

<210> SEQ ID NO 23
<211> LENGTH: 360

```
<212> TYPE: DNA
<213> ORGANISM: Artificial Sequence
<220> FEATURE:
<223> OTHER INFORMATION: synthetic anti-CLL-1 monoclonal antibody M2
      heavy chain coding sequence

<400> SEQUENCE: 23
gaggtccagc tgcggcagtc tggacctgag ctggtaaagc ctggggcttc agtgaagatg      60
tcctgcaagg cttctggata cacgttcact agctatttta tgcactgggt gaagcagaag     120
cctgggcagg gccttgagtg gattggattt attaatcctt acaatgatgg tactaagtat     180
aatgagaagt tcaaaggcaa ggccacactg acttcagaca atcctccag cacagcctac      240 atggagctca acagcctgac ctctgaggac tctgcggtct attactgtac aagagatgat     300
ggttattacg actatgctat ggactactgg ggtcaaggaa cctcagtcac cgtctcctca     360

<210> SEQ ID NO 24
<211> LENGTH: 120
<212> TYPE: PRT
<213> ORGANISM: Artificial Sequence
<220> FEATURE:
<223> OTHER INFORMATION: synthetic anti-CLL-1 monoclonal antibody M2
      heavy chain

<400> SEQUENCE: 24

Glu Val Gln Leu Arg Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Phe Met His Trp Val Lys Gln Lys Pro Gly Gln Gly Leu Glu Trp Ile
        35                  40                  45

Gly Phe Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Thr Ala Tyr
65                  70                  75                  80

Met Glu Leu Asn Ser Leu Thr Ser Glu Asp Ser Ala Val Tyr Tyr Cys
                85                  90                  95

Thr Arg Asp Asp Gly Tyr Tyr Asp Tyr Ala Met Asp Tyr Trp Gly Gln
            100                 105                 110

Gly Thr Ser Val Thr Val Ser Ser
        115                 120

<210> SEQ ID NO 25
<211> LENGTH: 323
<212> TYPE: DNA
<213> ORGANISM: Artificial Sequence
<220> FEATURE:
<223> OTHER INFORMATION: synthetic anti-CLL-1 monoclonal antibody M2
      light chain coding sequence

<400> SEQUENCE: 25
gacatccaga tgacccagtc tccatcctcc ttatctgcct ctctgggaga aagagtcagt      60
ctcacttgtc gggcaagtca ggaaattagt gtttacttaa gctggcttca gcagaaacca     120
gatggaacta ttaaacgcct gatctacgcc gcatccactt tagattctgg tgtcccagaa     180
aggttcagtg gcagtaggtc tgggtcagat tattctctca ccatcagcag ccttgagtct     240
gaagattttg cagactatta ctgtctacaa tatgctagtt atccgtacac gttcggaggg     300
gggaccaagc tggaaataaa acg                                             323
```

<210> SEQ ID NO 26
<211> LENGTH: 108
<212> TYPE: PRT
<213> ORGANISM: Artificial Sequence
<220> FEATURE:
<223> OTHER INFORMATION: synthetic anti-CLL-1 monoclonal antibody M2
     light chain

<400> SEQUENCE: 26

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Glu Ile Ser Val Tyr
            20                  25                  30

Leu Ser Trp Leu Gln Gln Lys Pro Asp Gly Thr Ile Lys Arg Leu Ile
        35                  40                  45

Tyr Ala Ala Ser Thr Leu Asp Ser Gly Val Pro Glu Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Ala Ser Tyr Pro Tyr
                85                  90                  95

Thr Phe Gly Gly Gly Thr Lys Leu Glu Ile Lys Arg
            100                 105

<210> SEQ ID NO 27
<211> LENGTH: 345
<212> TYPE: DNA
<213> ORGANISM: Artificial Sequence
<220> FEATURE:
<223> OTHER INFORMATION: synthetic anti-CLL-1 monoclonal antibody M5
     heavy chain coding sequence

<400> SEQUENCE: 27
gaggttcagc tgcagcagtc tggggctgag cttgtgaggc caggggcctc agtcaagttg      60
tcctgcacag cttctggctt aacattaaa gacgactata tacactgggt gaagcagagg      120
cctgaacagg gcctggagtg gattggatgg attgatcctg agaaggtga tactgcatat      180
gcctcgaagt tccaggacaa ggccactata acctcagaca catcctccaa cacagcctac      240
ctgcagctca gcagcctgac atctgaggac actgccgtct attactgtac tttaactggg      300
aggtttgact attggggcca aggcaccact ctcacagtct cctca                     345

<210> SEQ ID NO 28
<211> LENGTH: 115
<212> TYPE: PRT
<213> ORGANISM: Artificial Sequence
<220> FEATURE:
<223> OTHER INFORMATION: synthetic anti-CLL-1 monoclonal antibody M5
     heavy chain

<400> SEQUENCE: 28

Glu Val Gln Leu Gln Gln Ser Gly Ala Glu Leu Val Arg Pro Gly Ala
1               5                   10                  15

Ser Val Lys Leu Ser Cys Thr Ala Ser Gly Phe Asn Ile Lys Asp Asp
            20                  25                  30

Tyr Ile His Trp Val Lys Gln Arg Pro Glu Gln Gly Leu Glu Trp Ile
        35                  40                  45

Gly Trp Ile Asp Pro Glu Lys Gly Asp Thr Ala Tyr Ala Ser Lys Phe
    50                  55                  60

Gln Asp Lys Ala Thr Ile Thr Ser Asp Thr Ser Ser Asn Thr Ala Tyr
65                  70                  75                  80

```
Leu Gln Leu Ser Ser Leu Thr Ser Glu Asp Thr Ala Val Tyr Tyr Cys
                85                  90                  95

Thr Leu Thr Gly Arg Phe Asp Tyr Trp Gly Gln Gly Thr Thr Leu Thr
            100                 105                 110

Val Ser Ser
        115

<210> SEQ ID NO 29
<211> LENGTH: 337
<212> TYPE: DNA
<213> ORGANISM: Artificial Sequence
<220> FEATURE:
<223> OTHER INFORMATION: synthetic anti-CLL-1 monoclonal antibody M5
      light chain coding sequence

<400> SEQUENCE: 29
gacattgtga tgtcacagtc tccatcctcc ctagctgtgt cagttggaga aaggttact      60 atgagctgca agtccagtca gagcctttta tatagtagta atcaaaaaaa taacttggcc   120
tggtaccagc agaaaccagg gcagtctcct aaactgctga tttactgggc atccactagg   180
gaatctgggg tccctgatcg cttcacaggc agtggatctg ggacagattt cactctcacc   240
atcagcagtg tgcaggctga agacctggca gtttattact gtcagcaata ttatagctat   300
cggacgttcg gtggaggcac caagctggaa atcaaac                            337

<210> SEQ ID NO 30
<211> LENGTH: 112
<212> TYPE: PRT
<213> ORGANISM: Artificial Sequence
<220> FEATURE:
<223> OTHER INFORMATION: synthetic anti-CLL-1 monoclonal antibody M5
      light chain

<400> SEQUENCE: 30

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Gln
                85                  90                  95

Tyr Tyr Ser Tyr Arg Thr Phe Gly Gly Gly Thr Lys Leu Glu Ile Lys
            100                 105                 110

<210> SEQ ID NO 31
<211> LENGTH: 351
<212> TYPE: DNA
<213> ORGANISM: Artificial Sequence
<220> FEATURE:
<223> OTHER INFORMATION: synthetic anti-CLL-1 monoclonal antibody G12
      heavy chain coding sequence

<400> SEQUENCE: 31
caggtgcaac tgcagcagcc tggggctgag ctggtgaagc ctggggcctc aatgaagatg      60
tcctgcaagg cttctggcta cacatttccc agttccaata tacactggct aaagcagaca   120
```

-continued

```
cctggacagg gcctggaatg gattggagtt atttatccag gaaatggtga tacttcctac      180
aatcagaagt tcaaagacaa ggccacattg actacagaca gtcctccag cacagcctac       240 atgcagctca gcagcctgac gtctgaggac tctgcgatct atttctgtgc aagagtgtat     300
aactggcact cgatgtctg gggcgcaggg accacggtca ccgtctcctc a                351
```

<210> SEQ ID NO 32
<211> LENGTH: 117
<212> TYPE: PRT
<213> ORGANISM: Artificial Sequence
<220> FEATURE:
<223> OTHER INFORMATION: synthetic anti-CLL-1 monoclonal antibody G12
      heavy chain

<400> SEQUENCE: 32

```
Gln Val Gln Leu Gln Gln Pro Gly Ala Glu Leu Val Lys Pro Gly Ala
1               5                   10                  15

Ser Met Lys Met Ser Cys Lys Ala Ser Gly Tyr Thr Phe Pro Ser Ser
            20                  25                  30

Asn Ile His Trp Leu Lys Gln Thr Pro Gly Gln Gly Leu Glu Trp Ile
        35                  40                  45

Gly Val Ile Tyr Pro Gly Asn Gly Asp Thr Ser Tyr Asn Gln Lys Phe
    50                  55                  60

Lys Asp Lys Ala Thr Leu Thr Thr Asp Lys Ser Ser Thr Ala Tyr
65                  70                  75                  80

Met Gln Leu Ser Ser Leu Thr Ser Glu Asp Ser Ala Ile Tyr Phe Cys
                85                  90                  95

Ala Arg Val Tyr Asn Trp His Phe Asp Val Trp Gly Ala Gly Thr Thr
            100                 105                 110

Val Thr Val Ser Ser
        115
```

<210> SEQ ID NO 33
<211> LENGTH: 335
<212> TYPE: DNA
<213> ORGANISM: Artificial Sequence
<220> FEATURE:
<223> OTHER INFORMATION: synthetic anti-CLL-1 monoclonal antibody G12
      light chain coding sequence

<400> SEQUENCE: 33

```
aacattgtgc tgacccaatc tccagcttct ttggctgtgt ctctagggca gagggccacc      60
atatcctgca gagccagtga aagtgttgat ggttatggcg atatttttat gctctggtac     120
cagcagaaac caggacagcc acccaaactc ctcatctatt ttgcatccaa cctagaatct     180
ggggtccctg ccaggttcag tggcagtggg tcgaggacac acttcaccct caccattgat     240
cctgtggagg ctgatgatgc tgcaacctat tactgtcagc aaaataatga ggatccatac     300
acgttcggag gggggactaa gctggaaata aaacg                                 335
```

<210> SEQ ID NO 34
<211> LENGTH: 112
<212> TYPE: PRT
<213> ORGANISM: Artificial Sequence
<220> FEATURE:
<223> OTHER INFORMATION: synthetic anti-CLL-1 monoclonal antibody G12
      light chain

<400> SEQUENCE: 34

```
Asn Ile Val Leu Thr Gln Ser Pro Ala Ser Leu Ala Val Ser Leu Gly
```

```
                1               5                   10                  15
Gln Arg Ala Thr Ile Ser Cys Arg Ala Ser Glu Ser Val Asp Gly Tyr
                20                  25                  30

Gly Asp Ile Phe Met Leu Trp Tyr Gln Gln Lys Pro Gly Gln Pro Pro
                35                  40                  45

Lys Leu Leu Ile Tyr Phe Ala Ser Asn Leu Glu Ser Gly Val Pro Ala
                50                  55                  60

Arg Phe Ser Gly Ser Gly Ser Arg Thr Asp Phe Thr Leu Thr Ile Asp
65                  70                  75                  80

Pro Val Glu Ala Asp Asp Ala Ala Thr Tyr Tyr Cys Gln Gln Asn Asn
                    85                  90                  95

Glu Asp Pro Tyr Thr Phe Gly Gly Gly Thr Lys Leu Glu Ile Lys Arg
                100                 105                 110
```

<210> SEQ ID NO 35
<211> LENGTH: 15
<212> TYPE: PRT
<213> ORGANISM: Artificial Sequence
<220> FEATURE:
<223> OTHER INFORMATION: synthetic anti-CLL-1 monoclonal antibody M26
      heavy chain J sequence

<400> SEQUENCE: 35

```
Cys Thr Arg Asp Asp Gly Tyr Tyr Gly Tyr Ala Met Asp Tyr Trp
1               5                   10                  15
```

<210> SEQ ID NO 36
<211> LENGTH: 15
<212> TYPE: PRT
<213> ORGANISM: Artificial Sequence
<220> FEATURE:
<223> OTHER INFORMATION: synthetic anti-CLL-1 monoclonal antibody M31
      heavy chain J sequence

<400> SEQUENCE: 36

```
Cys Ala Arg Pro Ile Tyr Phe Asp Asn Asp Tyr Phe Asp Tyr Trp
1               5                   10                  15
```

<210> SEQ ID NO 37
<211> LENGTH: 15
<212> TYPE: PRT
<213> ORGANISM: Artificial Sequence
<220> FEATURE:
<223> OTHER INFORMATION: synthetic anti-CLL-1 monoclonal antibody G4
      heavy chain J sequence

<400> SEQUENCE: 37

```
Cys Ala Arg Thr Asp Asp Tyr Asp Asp Tyr Thr Met Asp Tyr Trp
1               5                   10                  15
```

<210> SEQ ID NO 38
<211> LENGTH: 16
<212> TYPE: PRT
<213> ORGANISM: Artificial Sequence
<220> FEATURE:
<223> OTHER INFORMATION: synthetic anti-CLL-1 monoclonal antibody M22
      heavy chain J sequence

<400> SEQUENCE: 38

```
Cys Ala Ile Tyr Tyr Gly Asn Pro Ser Tyr Tyr Ala Met Asp Tyr Trp
1               5                   10                  15
```

<210> SEQ ID NO 39
<211> LENGTH: 14

```
<212> TYPE: PRT
<213> ORGANISM: Artificial Sequence
<220> FEATURE:
<223> OTHER INFORMATION: synthetic anti-CLL-1 monoclonal antibody M29
      heavy chain J sequence

<400> SEQUENCE: 39

Cys Ala Arg Tyr Tyr Asp Tyr Asp Tyr Tyr Phe Asp Tyr Trp
1               5                   10

<210> SEQ ID NO 40
<211> LENGTH: 15
<212> TYPE: PRT
<213> ORGANISM: Artificial Sequence
<220> FEATURE:
<223> OTHER INFORMATION: synthetic anti-CLL-1 monoclonal antibody M2
      heavy chain J sequence

<400> SEQUENCE: 40

Cys Thr Arg Asp Asp Gly Tyr Tyr Asp Tyr Ala Met Asp Tyr Trp
1               5                   10                  15

<210> SEQ ID NO 41
<211> LENGTH: 10
<212> TYPE: PRT
<213> ORGANISM: Artificial Sequence
<220> FEATURE:
<223> OTHER INFORMATION: synthetic anti-CLL-1 monoclonal antibody M5
      heavy chain J sequence

<400> SEQUENCE: 41

Cys Thr Leu Thr Gly Arg Phe Asp Tyr Trp
1               5                   10

<210> SEQ ID NO 42
<211> LENGTH: 12
<212> TYPE: PRT
<213> ORGANISM: Artificial Sequence
<220> FEATURE:
<223> OTHER INFORMATION: synthetic anti-CLL-1 monoclonal antibody G12
      heavy chain J sequence

<400> SEQUENCE: 42

Cys Ala Arg Val Tyr Asn Trp His Phe Asp Val Trp
1               5                   10

<210> SEQ ID NO 43
<211> LENGTH: 11
<212> TYPE: PRT
<213> ORGANISM: Artificial Sequence
<220> FEATURE:
<223> OTHER INFORMATION: synthetic anti-CLL-1 monoclonal antibody M26
      light chain J sequence

<400> SEQUENCE: 43

Cys Leu Gln Tyr Ala Ile Tyr Pro Tyr Thr Phe
1               5                   10

<210> SEQ ID NO 44
<211> LENGTH: 11
<212> TYPE: PRT
<213> ORGANISM: Artificial Sequence
<220> FEATURE:
<223> OTHER INFORMATION: synthetic anti-CLL-1 monoclonal antibody M31
      light chain J sequence

<400> SEQUENCE: 44

Cys Gln Gln Asn Asn Tyr Asp Pro Trp Thr Phe
```

```
<210> SEQ ID NO 45
<211> LENGTH: 11
<212> TYPE: PRT
<213> ORGANISM: Artificial Sequence
<220> FEATURE:
<223> OTHER INFORMATION: synthetic anti-CLL-1 monoclonal antibody G4
      light chain J sequence

<400> SEQUENCE: 45

Cys Gln Gln Gly Lys Thr Leu Leu Trp Thr Phe
1               5                   10

<210> SEQ ID NO 46
<211> LENGTH: 11
<212> TYPE: PRT
<213> ORGANISM: Artificial Sequence
<220> FEATURE:
<223> OTHER INFORMATION: synthetic anti-CLL-1 monoclonal antibody M22
      light chain J sequence

<400> SEQUENCE: 46

Cys Gln Asn Asp Tyr Ser Tyr Pro Phe Thr Phe
1               5                   10

<210> SEQ ID NO 47
<211> LENGTH: 10
<212> TYPE: PRT
<213> ORGANISM: Artificial Sequence
<220> FEATURE:
<223> OTHER INFORMATION: synthetic anti-CLL-1 monoclonal antibody M29
      light chain J sequence

<400> SEQUENCE: 47

Cys Leu Gln Tyr Asp Tyr Leu Trp Thr Phe
1               5                   10

<210> SEQ ID NO 48
<211> LENGTH: 11
<212> TYPE: PRT
<213> ORGANISM: Artificial Sequence
<220> FEATURE:
<223> OTHER INFORMATION: synthetic anti-CLL-1 monoclonal antibody M2
      light chain J sequence

<400> SEQUENCE: 48

Cys Leu Gln Tyr Ala Ser Tyr Pro Tyr Thr Phe
1               5                   10

<210> SEQ ID NO 49
<211> LENGTH: 10
<212> TYPE: PRT
<213> ORGANISM: Artificial Sequence
<220> FEATURE:
<223> OTHER INFORMATION: synthetic anti-CLL-1 monoclonal antibody M5
      light chain J sequence

<400> SEQUENCE: 49

Cys Gln Gln Tyr Tyr Ser Tyr Arg Thr Phe
1               5                   10

<210> SEQ ID NO 50
<211> LENGTH: 11
<212> TYPE: PRT
<213> ORGANISM: Artificial Sequence
<220> FEATURE:
<223> OTHER INFORMATION: synthetic anti-CLL-1 monoclonal antibody G12
``` light chain J sequence

<400> SEQUENCE: 50

Cys Gln Gln Asn Asn Glu Asp Pro Tyr Thr Phe
1               5                   10

<210> SEQ ID NO 51
<211> LENGTH: 8
<212> TYPE: PRT
<213> ORGANISM: Artificial Sequence
<220> FEATURE:
<223> OTHER INFORMATION: synthetic anti-CLL-1 monoclonal antibody M26
      CDR H1

<400> SEQUENCE: 51

Gly Tyr Thr Phe Thr Ser Tyr Phe
1               5

<210> SEQ ID NO 52
<211> LENGTH: 8
<212> TYPE: PRT
<213> ORGANISM: Artificial Sequence
<220> FEATURE:
<223> OTHER INFORMATION: synthetic anti-CLL-1 monoclonal antibody M31
      CDR H1

<400> SEQUENCE: 52

Gly Tyr Thr Phe Thr Ser Tyr Val
1               5

<210> SEQ ID NO 53
<211> LENGTH: 8
<212> TYPE: PRT
<213> ORGANISM: Artificial Sequence
<220> FEATURE:
<223> OTHER INFORMATION: synthetic anti-CLL-1 monoclonal antibody G4
      CDR H1

<400> SEQUENCE: 53

Gly Tyr Ser Phe Thr Gly Tyr Thr
1               5

<210> SEQ ID NO 54
<211> LENGTH: 8
<212> TYPE: PRT
<213> ORGANISM: Artificial Sequence
<220> FEATURE:
<223> OTHER INFORMATION: synthetic anti-CLL-1 monoclonal antibody M22
      CDR H1

<400> SEQUENCE: 54

Gly Tyr Thr Phe Thr Arg Tyr Trp
1               5

<210> SEQ ID NO 55
<211> LENGTH: 8
<212> TYPE: PRT
<213> ORGANISM: Artificial Sequence
<220> FEATURE:
<223> OTHER INFORMATION: synthetic anti-CLL-1 monoclonal antibody M29
      CDR H1

<400> SEQUENCE: 55

Gly Tyr Ile Phe Thr Ser Tyr Val
1               5

<210> SEQ ID NO 56

```
<211> LENGTH: 8
<212> TYPE: PRT
<213> ORGANISM: Artificial Sequence
<220> FEATURE:
<223> OTHER INFORMATION: synthetic anti-CLL-1 monoclonal antibody M2
      CDR H1

<400> SEQUENCE: 56

Gly Tyr Thr Phe Thr Ser Tyr Phe
1               5

<210> SEQ ID NO 57
<211> LENGTH: 8
<212> TYPE: PRT
<213> ORGANISM: Artificial Sequence
<220> FEATURE:
<223> OTHER INFORMATION: synthetic anti-CLL-1 monoclonal antibody M5
      CDR H1

<400> SEQUENCE: 57

Gly Phe Asn Ile Lys Asp Asp Tyr
1               5

<210> SEQ ID NO 58
<211> LENGTH: 8
<212> TYPE: PRT
<213> ORGANISM: Artificial Sequence
<220> FEATURE:
<223> OTHER INFORMATION: synthetic anti-CLL-1 monoclonal antibody G12
      CDR H1

<400> SEQUENCE: 58

Gly Tyr Thr Phe Pro Ser Ser Asn
1               5

<210> SEQ ID NO 59
<211> LENGTH: 8
<212> TYPE: PRT
<213> ORGANISM: Artificial Sequence
<220> FEATURE:
<223> OTHER INFORMATION: synthetic anti-CLL-1 monoclonal antibody M26
      CDR H2

<400> SEQUENCE: 59

Ile Asn Pro Tyr Asn Asp Gly Ser
1               5

<210> SEQ ID NO 60
<211> LENGTH: 8
<212> TYPE: PRT
<213> ORGANISM: Artificial Sequence
<220> FEATURE:
<223> OTHER INFORMATION: synthetic anti-CLL-1 monoclonal antibody M31
      CDR H2

<400> SEQUENCE: 60

Ile Asn Pro Tyr Asn Asp Gly Thr
1               5

<210> SEQ ID NO 61
<211> LENGTH: 8
<212> TYPE: PRT
<213> ORGANISM: Artificial Sequence
<220> FEATURE:
<223> OTHER INFORMATION: synthetic anti-CLL-1 monoclonal antibody G4
      CDR H2

<400> SEQUENCE: 61
```

```
Ile Asn Pro Tyr Asn Asp Gly Thr
1               5

<210> SEQ ID NO 62
<211> LENGTH: 8
<212> TYPE: PRT
<213> ORGANISM: Artificial Sequence
<220> FEATURE:
<223> OTHER INFORMATION: synthetic anti-CLL-1 monoclonal antibody M22
      CDR H2

<400> SEQUENCE: 62

Ile Asp Pro Ser Asp Thr Glu Thr
1               5

<210> SEQ ID NO 63
<211> LENGTH: 8
<212> TYPE: PRT
<213> ORGANISM: Artificial Sequence
<220> FEATURE:
<223> OTHER INFORMATION: synthetic anti-CLL-1 monoclonal antibody M29
      CDR H2

<400> SEQUENCE: 63

Ile Asn Pro Tyr Asn Asp Gly Thr
1               5

<210> SEQ ID NO 64
<211> LENGTH: 8
<212> TYPE: PRT
<213> ORGANISM: Artificial Sequence
<220> FEATURE:
<223> OTHER INFORMATION: synthetic anti-CLL-1 monoclonal antibody M2
      CDR H2

<400> SEQUENCE: 64

Ile Asn Pro Tyr Asn Asp Gly Thr
1               5

<210> SEQ ID NO 65
<211> LENGTH: 8
<212> TYPE: PRT
<213> ORGANISM: Artificial Sequence
<220> FEATURE:
<223> OTHER INFORMATION: synthetic anti-CLL-1 monoclonal antibody M5
      CDR H2

<400> SEQUENCE: 65

Ile Asp Pro Glu Lys Gly Asp Thr
1               5

<210> SEQ ID NO 66
<211> LENGTH: 8
<212> TYPE: PRT
<213> ORGANISM: Artificial Sequence
<220> FEATURE:
<223> OTHER INFORMATION: synthetic anti-CLL-1 monoclonal antibody G12
      CDR H2

<400> SEQUENCE: 66

Ile Tyr Pro Gly Asn Gly Asp Thr
1               5

<210> SEQ ID NO 67
<211> LENGTH: 13
<212> TYPE: PRT
<213> ORGANISM: Artificial Sequence
<220> FEATURE:
```

<223> OTHER INFORMATION: synthetic anti-CLL-1 monoclonal antibody M26
    CDR H3

<400> SEQUENCE: 67

Thr Arg Asp Asp Gly Tyr Tyr Gly Tyr Ala Met Asp Tyr
1               5                   10

<210> SEQ ID NO 68
<211> LENGTH: 13
<212> TYPE: PRT
<213> ORGANISM: Artificial Sequence
<220> FEATURE:
<223> OTHER INFORMATION: synthetic anti-CLL-1 monoclonal antibody M31
    CDR H3

<400> SEQUENCE: 68

Ala Arg Pro Ile Tyr Phe Asp Asn Asp Tyr Phe Asp Tyr
1               5                   10

<210> SEQ ID NO 69
<211> LENGTH: 13
<212> TYPE: PRT
<213> ORGANISM: Artificial Sequence
<220> FEATURE:
<223> OTHER INFORMATION: synthetic anti-CLL-1 monoclonal antibody G4
    CDR H3

<400> SEQUENCE: 69

Ala Arg Thr Asp Asp Tyr Asp Asp Tyr Thr Met Asp Tyr
1               5                   10

<210> SEQ ID NO 70
<211> LENGTH: 14
<212> TYPE: PRT
<213> ORGANISM: Artificial Sequence
<220> FEATURE:
<223> OTHER INFORMATION: synthetic anti-CLL-1 monoclonal antibody M22
    CDR H3

<400> SEQUENCE: 70

Ala Ile Tyr Tyr Gly Asn Pro Ser Tyr Tyr Ala Met Asp Tyr
1               5                   10

<210> SEQ ID NO 71
<211> LENGTH: 12
<212> TYPE: PRT
<213> ORGANISM: Artificial Sequence
<220> FEATURE:
<223> OTHER INFORMATION: synthetic anti-CLL-1 monoclonal antibody M29
    CDR H3

<400> SEQUENCE: 71

Ala Arg Tyr Tyr Asp Tyr Asp Tyr Tyr Phe Asp Tyr
1               5                   10

<210> SEQ ID NO 72
<211> LENGTH: 13
<212> TYPE: PRT
<213> ORGANISM: Artificial Sequence
<220> FEATURE:
<223> OTHER INFORMATION: synthetic anti-CLL-1 monoclonal antibody M2
    CDR H3

<400> SEQUENCE: 72

Thr Arg Asp Asp Gly Tyr Tyr Asp Tyr Ala Met Asp Tyr
1               5                   10

```
<210> SEQ ID NO 73
<211> LENGTH: 8
<212> TYPE: PRT
<213> ORGANISM: Artificial Sequence
<220> FEATURE:
<223> OTHER INFORMATION: synthetic anti-CLL-1 monoclonal antibody M5
      CDR H3

<400> SEQUENCE: 73

Thr Leu Thr Gly Arg Phe Asp Tyr
1               5

<210> SEQ ID NO 74
<211> LENGTH: 10
<212> TYPE: PRT
<213> ORGANISM: Artificial Sequence
<220> FEATURE:
<223> OTHER INFORMATION: synthetic anti-CLL-1 monoclonal antibody G12
      CDR H3

<400> SEQUENCE: 74

Ala Arg Val Tyr Asn Trp His Phe Asp Val
1               5                   10

<210> SEQ ID NO 75
<211> LENGTH: 6
<212> TYPE: PRT
<213> ORGANISM: Artificial Sequence
<220> FEATURE:
<223> OTHER INFORMATION: synthetic anti-CLL-1 monoclonal antibody M26
      CDR L1

<400> SEQUENCE: 75

Gln Glu Leu Ser Gly Tyr
1               5

<210> SEQ ID NO 76
<211> LENGTH: 10
<212> TYPE: PRT
<213> ORGANISM: Artificial Sequence
<220> FEATURE:
<223> OTHER INFORMATION: synthetic anti-CLL-1 monoclonal antibody M31
      CDR L1

<400> SEQUENCE: 76

Glu Ser Val Asp Ser Tyr Gly Asn Ser Phe
1               5                   10

<210> SEQ ID NO 77
<211> LENGTH: 6
<212> TYPE: PRT
<213> ORGANISM: Artificial Sequence
<220> FEATURE:
<223> OTHER INFORMATION: synthetic anti-CLL-1 monoclonal antibody G4
      CDR L1

<400> SEQUENCE: 77

His Asp Ile Ser Asn Tyr
1               5

<210> SEQ ID NO 78
<211> LENGTH: 12
<212> TYPE: PRT
<213> ORGANISM: Artificial Sequence
<220> FEATURE:
<223> OTHER INFORMATION: synthetic anti-CLL-1 monoclonal antibody M22
      CDR L1

<400> SEQUENCE: 78
```

Gln Asn Leu Leu Asn Ser Gly Asn Gln Lys Lys Tyr
1               5                   10

<210> SEQ ID NO 79
<211> LENGTH: 6
<212> TYPE: PRT
<213> ORGANISM: Artificial Sequence
<220> FEATURE:
<223> OTHER INFORMATION: synthetic anti-CLL-1 monoclonal antibody M29
      CDR L1

<400> SEQUENCE: 79

Gln Asp Ile Asn Lys Tyr
1               5

<210> SEQ ID NO 80
<211> LENGTH: 6
<212> TYPE: PRT
<213> ORGANISM: Artificial Sequence
<220> FEATURE:
<223> OTHER INFORMATION: synthetic anti-CLL-1 monoclonal antibody M2
      CDR L1

<400> SEQUENCE: 80

Gln Glu Ile Ser Val Tyr
1               5

<210> SEQ ID NO 81
<211> LENGTH: 12
<212> TYPE: PRT
<213> ORGANISM: Artificial Sequence
<220> FEATURE:
<223> OTHER INFORMATION: synthetic anti-CLL-1 monoclonal antibody M5
      CDR L1

<400> SEQUENCE: 81

Gln Ser Leu Leu Tyr Ser Ser Asn Gln Lys Asn Asn
1               5                   10

<210> SEQ ID NO 82
<211> LENGTH: 10
<212> TYPE: PRT
<213> ORGANISM: Artificial Sequence
<220> FEATURE:
<223> OTHER INFORMATION: synthetic anti-CLL-1 monoclonal antibody G12
      CDR L1

<400> SEQUENCE: 82

Glu Ser Val Asp Gly Tyr Gly Asp Ile Phe
1               5                   10

<210> SEQ ID NO 83
<211> LENGTH: 3
<212> TYPE: PRT
<213> ORGANISM: Artificial Sequence
<220> FEATURE:
<223> OTHER INFORMATION: synthetic anti-CLL-1 monoclonal antibody M26
      CDR L2

<400> SEQUENCE: 83

Ala Ala Ser
1

<210> SEQ ID NO 84
<211> LENGTH: 3
<212> TYPE: PRT
<213> ORGANISM: Artificial Sequence

```
<220> FEATURE:
<223> OTHER INFORMATION: synthetic anti-CLL-1 monoclonal antibody M31
      CDR L2

<400> SEQUENCE: 84

Leu Ala Ser
1

<210> SEQ ID NO 85
<211> LENGTH: 3
<212> TYPE: PRT
<213> ORGANISM: Artificial Sequence
<220> FEATURE:
<223> OTHER INFORMATION: synthetic anti-CLL-1 monoclonal antibody G4
      CDR L2

<400> SEQUENCE: 85

Tyr Thr Ser
1

<210> SEQ ID NO 86
<211> LENGTH: 3
<212> TYPE: PRT
<213> ORGANISM: Artificial Sequence
<220> FEATURE:
<223> OTHER INFORMATION: synthetic anti-CLL-1 monoclonal antibody M22
      CDR L2

<400> SEQUENCE: 86

Trp Ala Ser
1

<210> SEQ ID NO 87
<211> LENGTH: 3
<212> TYPE: PRT
<213> ORGANISM: Artificial Sequence
<220> FEATURE:
<223> OTHER INFORMATION: synthetic anti-CLL-1 monoclonal antibody M29
      CDR L2

<400> SEQUENCE: 87

Tyr Thr Ser
1

<210> SEQ ID NO 88
<211> LENGTH: 3
<212> TYPE: PRT
<213> ORGANISM: Artificial Sequence
<220> FEATURE:
<223> OTHER INFORMATION: synthetic anti-CLL-1 monoclonal antibody M2
      CDR L2

<400> SEQUENCE: 88

Ala Ala Ser
1

<210> SEQ ID NO 89
<211> LENGTH: 3
<212> TYPE: PRT
<213> ORGANISM: Artificial Sequence
<220> FEATURE:
<223> OTHER INFORMATION: synthetic anti-CLL-1 monoclonal antibody M5
      CDR L2

<400> SEQUENCE: 89

Trp Ala Ser
1
```

<210> SEQ ID NO 90
<211> LENGTH: 3
<212> TYPE: PRT
<213> ORGANISM: Artificial Sequence
<220> FEATURE:
<223> OTHER INFORMATION: synthetic anti-CLL-1 monoclonal antibody G12
      CDR L2

<400> SEQUENCE: 90

Phe Ala Ser
1

<210> SEQ ID NO 91
<211> LENGTH: 9
<212> TYPE: PRT
<213> ORGANISM: Artificial Sequence
<220> FEATURE:
<223> OTHER INFORMATION: synthetic anti-CLL-1 monoclonal antibody M26
      CDR L3

<400> SEQUENCE: 91

Leu Gln Tyr Ala Ile Tyr Pro Tyr Thr
1               5

<210> SEQ ID NO 92
<211> LENGTH: 9
<212> TYPE: PRT
<213> ORGANISM: Artificial Sequence
<220> FEATURE:
<223> OTHER INFORMATION: synthetic anti-CLL-1 monoclonal antibody M31
      CDR L3

<400> SEQUENCE: 92

Gln Gln Asn Asn Tyr Asp Pro Trp Thr
1               5

<210> SEQ ID NO 93
<211> LENGTH: 9
<212> TYPE: PRT
<213> ORGANISM: Artificial Sequence
<220> FEATURE:
<223> OTHER INFORMATION: synthetic anti-CLL-1 monoclonal antibody G4
      CDR L3

<400> SEQUENCE: 93

Gln Gln Gly Lys Thr Leu Leu Trp Thr
1               5

<210> SEQ ID NO 94
<211> LENGTH: 9
<212> TYPE: PRT
<213> ORGANISM: Artificial Sequence
<220> FEATURE:
<223> OTHER INFORMATION: synthetic anti-CLL-1 monoclonal antibody M22
      CDR L3

<400> SEQUENCE: 94

Gln Asn Asp Tyr Ser Tyr Pro Phe Thr
1               5

<210> SEQ ID NO 95
<211> LENGTH: 8
<212> TYPE: PRT
<213> ORGANISM: Artificial Sequence
<220> FEATURE:
<223> OTHER INFORMATION: synthetic anti-CLL-1 monoclonal antibody M29
      CDR L3

```
<400> SEQUENCE: 95

Leu Gln Tyr Asp Tyr Leu Trp Thr
1               5

<210> SEQ ID NO 96
<211> LENGTH: 9
<212> TYPE: PRT
<213> ORGANISM: Artificial Sequence
<220> FEATURE:
<223> OTHER INFORMATION: synthetic anti-CLL-1 monoclonal antibody M2
      CDR L3

<400> SEQUENCE: 96

Leu Gln Tyr Ala Ser Tyr Pro Tyr Thr
1               5

<210> SEQ ID NO 97
<211> LENGTH: 8
<212> TYPE: PRT
<213> ORGANISM: Artificial Sequence
<220> FEATURE:
<223> OTHER INFORMATION: synthetic anti-CLL-1 monoclonal antibody M5
      CDR L3

<400> SEQUENCE: 97

Gln Gln Tyr Tyr Ser Tyr Arg Thr
1               5

<210> SEQ ID NO 98
<211> LENGTH: 9
<212> TYPE: PRT
<213> ORGANISM: Artificial Sequence
<220> FEATURE:
<223> OTHER INFORMATION: synthetic anti-CLL-1 monoclonal antibody G12
      CDR L3

<400> SEQUENCE: 98

Gln Gln Asn Asn Glu Asp Pro Tyr Thr
1               5
```

ANTIBODIES SPECIFIC FOR CLL-1

CROSS REFERENCE TO RELATED APPLICATION

This application is a continuation of U.S. patent application Ser. No. 14/853,881, filed Sep. 14, 2015, which is a continuation of U.S. patent application Ser. No. 13/794,525, filed Mar. 11, 2013, which claims priority to U.S. Provisional Application No. 61/643,739, filed May 7, 2012, and U.S. Provisional Application No. 61/699,134, filed Sep. 10, 2012, the disclosures of which are incorporated by reference in their entireties.

REFERENCE TO SUBMISSION OF A SEQUENCE LISTING

This application includes a Sequence Listing as a text file named "092950-0950734 SEQ" created Sep. 9, 2015 and containing 45,885 bytes. The material contained in this text file is incorporated by reference in its entirety for all purposes.

BACKGROUND OF THE INVENTION

C type Lectin Like molecule 1 (CLL-1) is expressed on AML cells, and on cancer stem cells (CSCs), which are cells that can give rise to additional cancer cells.

One of the major limitations of chemotherapy is the general inability of anticancer drugs to discriminate between normal and cancer cells. Almost all members of the major categories of antineoplastic agents have considerable toxicity for normal cells.

Compositions that specifically target cancer cells can avoid this problem. However, existing cancer targets do not target CSCs. For this reason, existing chemotherapeutic strategies, even when specifically delivered to cancer cells, do not effectively eliminate the cancer. Risk of recurrence remains because the surviving CSCs can give rise to new cancer cells.

CSCs express CD34, similar to hematopoietic stem cells (HSCs), but CLL-1 is not expressed on HSCs. This allows CSCs to be specifically targeted using CLL-1. Provided herein are CLL-1 antibodies that recognize a high percentage of CLL-1 expressing cells. The present CLL-1 antibodies are effective for both complement dependent and antibody dependent cytoxicity of CLL-1 expressing cells, and inhibit tumor growth of CLL-1 expressing cancer cells. The presently described antibodies provide novel diagnostic and therapeutic strategies for targeting CLL-1-associated disorders.

BRIEF SUMMARY OF THE INVENTION

Provided herein are antibodies specific for CLL-1 ("CLL-1 antibodies") that bind a high percentage of CLL-1 expressing primary cells from AML patient samples. In some embodiments, the CLL-1 antibody specifically binds the extracellular domain of human CLL-1 with a Kd of 10 nM or less, e.g., any of 5 nM, 1 nM, 500 pM, 200 pM, 100 pM, 50 pM or less. In some embodiments, the CLL-1 antibody binds cynomolgus CLL-1 with a Kd of 100 nM, 10 nM, 1 nM, 100 pM or less. For example, in some embodiments, cynomolgus CLL-1 and human CLL-1 compete for binding to the CLL-1 antibody. One of skill will understand that higher affinity binding is expressed as lower Kd (lower concentration of antibody target necessary for binding).

In some embodiments, the CLL-1 antibody binds a polypeptide consisting of the C-lectin domain of CLL-1 with a Kd at least 5-fold higher than a polypeptide comprising or consisting of the C-lectin and stalk domains of CLL-1, e.g., at least any of 10, 20, 50, or 100-fold higher. That is, the antibody binds a polypeptide comprising the stalk and C-lectin domains of CLL-1 with a higher affinity than it binds the C-lectin domain alone or the stalk domain alone. In some embodiments, the CLL-1 antibody binds an epitope that includes part of the stalk and part of the C-lectin domains. In some embodiments, the CLL-1 antibody binds a polypeptide consisting of the C-lectin and stalk domains of human C-type lectin like molecule (CLL-1) with greater affinity than it binds either (a) a polypeptide consisting of the C-lectin domain of human CLL-1 or (b) a polypeptide consisting of the stalk domain of human CLL-1. For example, the CLL-1 antibodies designated as M26 and M31 bind amino acids 101-265 of human CLL-1 with higher affinity than amino acids 141-265 of human CLL-1 (with reference to SEQ ID NO:2).

In some embodiments, the CLL-1 antibody binds the C-lectin domain of CLL-1 with a Kd at least 5-fold higher than it binds the full length CLL-1 extracellular domain, e.g., at least any of 10, 20, 50, or 100-fold higher. That is, the affinity of the CLL-1 antibody is at least any of 5, 10, 20, 50, or 100 fold lower than for the full length CLL-1 extracellular domain (e.g., as expressed on a cell). In some embodiments, the CLL-1 antibody binds quiescent CLL-1 expressing cells. In some embodiments, the CLL-1 antibody binds quiescent CLL-1 expressing cells with a Kd of 10 nM or less, e.g., any of 1 nM, 500 pM, 200 pM, 100 pM, 50 pM or less.

In some embodiments, the CLL-1 antibody binds at least 60% of the cells in a culture of HL60 cells, e.g., at least any of 70, 75, 80, 85, 90, 95, or higher % of the HL60 cells. In some embodiments, the CLL-1 antibody binds at least 30% of the nucleated cells in a sample of primary cells from an AML patient (e.g., any of 40, 50, 60, 70, 80, 85, 90, 95 or higher %), wherein the sample of primary cells is peripheral blood or biopsy of tumor tissue. One of skill will understand that, in such a cell binding assay, an appropriate concentration of antibody is added, e.g., so that there are sufficient antibody molecules present to bind the number of cells in the culture or sample.

In some embodiments, the CLL-1 antibody has an EC50 of less than 1 nM in an antibody drug conjugate (ADC) cytotoxicity assay with CLL-1 expressing cells, e.g., HL60 cells or primary AML cells. In some embodiments, the EC50 in the ADC assay is any of 500, 200, 100, 50 pM or less. In some embodiments, the CLL-1 antibody reduces colony formation of AML cells by at least 50%, e.g., at least 60%, 70%, 80% or more in an ADC cytotoxicity assay.

In some embodiments, the cells are primary patient AML cells. In some embodiments, the cells are AML cancer stem cells. In some embodiments, the CLL-1 antibody does not affect normal CD34+ hematopoietic stem cells (HSCs), or significantly reduce colony formation of normal CD34+ HSCs in an ADC cytotoxicity assay.

In some embodiments, the CLL-1 antibody has an EC50 of 1 ug/ml or less in a complement dependent cytotoxicity (CDC) assay with CLL-1 expressing cells, e.g., HL60 cells or primary AML cells. In some embodiments, the EC50 in the CDC assay is any of 500, 200, 100, 50, 20, 10 ng/ml or less. In some embodiments, the CLL-1 antibody has an EC50 of 1 ug/ml or less in an antibody dependent cell-mediated cytotoxicity (ADCC) assay with CLL-1 expressing cells, e.g., CLL-1 transfected 293 cells, HL60 cells, or primary AML cells. In some embodiments, the EC50 in the ADCC assay is any of 500, 200, 100 ng/ml or less. In some embodiments, the CLL-1 antibody, when administered to a mouse carrying an AML xenograft for at least 4 weeks reduces tumor burden at least 10-fold compared to an untreated control (i.e., a mouse carrying the AML xenograft but not treated with the CLL-1 antibody). In some embodiments, the AML xenograft is from a human AML cell line, e.g., HL60 or OCI AML-5 cells. In some embodiments, the AML xenograft is from primary human or primate (e.g., cynomolgus) AML cells.

In some embodiments, the CLL-1 antibody is selected from the group consisting of an antibody that competes for binding to CLL-1 (e.g., a CLL-1 expressing cell or AML cell) with an antibody selected from the group consisting of:
an antibody comprising the heavy and light chain CDRs of M26 (see Example 1);
an antibody comprising the heavy and light chain CDRs of M31;
an antibody comprising the heavy and light chain CDRs of G4;
an antibody comprising the heavy and light chain CDRs of M22;
an antibody comprising the heavy and light chain CDRs of M29;
an antibody comprising the heavy and light chain CDRs of M2;
an antibody comprising the heavy and light chain CDRs of M5;
an antibody comprising the heavy and light chain CDRs of G12;
an antibody comprising the heavy and light chain CDRs of M41;
an antibody comprising the heavy and light chain CDRs of E3;
an antibody comprising the heavy and light chain CDRs of B10;
an antibody comprising the heavy and light chain CDRs of G2;
an antibody comprising the heavy and light chain CDRs of G6;
an antibody comprising the heavy and light chain CDRs of G8;
an antibody comprising the heavy and light chain CDRs of G10;
an antibody comprising the heavy and light chain CDRs of G14;
an antibody comprising the heavy and light chain CDRs of G16;
an antibody comprising the heavy and light chain CDRs of G23;
an antibody comprising the heavy and light chain CDRs of G26;
an antibody comprising the heavy and light chain CDRs of G28; and
an antibody comprising the heavy and light chain CDRs of G30.

In some embodiments, the CLL-1 antibody is selected from an antibody selected from the group consisting of:
an antibody comprising the heavy and light chain CDRs of M26 (see Example 1);
an antibody comprising the heavy and light chain CDRs of M31;
an antibody comprising the heavy and light chain CDRs of G4;
an antibody comprising the heavy and light chain CDRs of M22;
an antibody comprising the heavy and light chain CDRs of M29;
an antibody comprising the heavy and light chain CDRs of M2;
an antibody comprising the heavy and light chain CDRs of M5;
an antibody comprising the heavy and light chain CDRs of G12;
an antibody comprising the heavy and light chain CDRs of M41;
an antibody comprising the heavy and light chain CDRs of E3;
an antibody comprising the heavy and light chain CDRs of B10;
an antibody comprising the heavy and light chain CDRs of G2;
an antibody comprising the heavy and light chain CDRs of G6;
an antibody comprising the heavy and light chain CDRs of G8;
an antibody comprising the heavy and light chain CDRs of G10;
an antibody comprising the heavy and light chain CDRs of G14;
an antibody comprising the heavy and light chain CDRs of G16;
an antibody comprising the heavy and light chain CDRs of G23;
an antibody comprising the heavy and light chain CDRs of G26;
an antibody comprising the heavy and light chain CDRs of G28; and
an antibody comprising the heavy and light chain CDRs of G30,
wherein any one or more of the the selected CDRs can have 1, 2, or 3 conservative amino acid substitutions compared to the original CDR sequence.

In some embodiments, the CLL-1 antibody comprises the heavy and light chain CDRs of M26. In some embodiments, the CLL-1 antibody comprises the heavy and light chain CDRs of M31. In some embodiments, the CLL-1 antibody comprises the heavy and light chain CDRs of G4.

In some embodiments, the CLL-1 antibody as described above binds a polypeptide consisting of the C-lectin domain of CLL-1 with a Kd at least 5-fold higher than a polypeptide consisting of the C-lectin and stalk domains of CLL-1 (e.g., any of 10, 20, 50, 100 or higher fold). In some embodiments, the CLL-1 antibody binds the C-lectin domain of CLL-1 with a Kd at least 5-fold higher than it binds full length CLL-1 extracellular domain (e.g., any of 10, 20, 50, 100 or higher fold). In some embodiments, the CLL-1 antibody as described above further binds at least 80% of the cells in a culture of HL60 cells (e.g., any of 85, 90, 95 or higher %). In some embodiments, the CLL-1 antibody as described above further binds at least 30% of the nucleated cells in a sample of AML cells from an individual with AML (e.g., any of 40, 50, 60, 70, 80, 85, 90, 95, or higher %). Again, in such a cell binding assay, an appropriate concentration of antibody is added, e.g., so that there are sufficient antibody molecules present to bind the number of cells in the culture or sample, and antibody concentration is not the limiting factor.

In some embodiments, the CLL-1 antibody as described above is a chimeric antibody with a human Fc region, e.g., from IgG1. In some embodiments, the CLL-1 antibody as described above is humanized. In some embodiments, the CLL-1 antibody as described above is an Fv fragment (e.g., Fab, Fab', or F(ab')2). In some embodiments, the CLL-1 antibody as described above is labeled e.g., conjugated to a detectable moiety. In some embodiments, the CLL-1 as described above is attached to a therapeutic compound, e.g., a cytotoxin or cell growth inhibitor.

In some embodiments, the CLL-1 antibody is selected from the group consisting of:
an antibody comprising variable region sequences with substantial identity (at least any of 85, 90, 95, or 98% identity) to those of M26 (Vh=SEQ ID NO:4; V1=SEQ ID NO:6)
an antibody comprising variable region sequences with substantial identity to those of M31 (Vh=SEQ ID NO:8; V1=SEQ ID NO:10);
an antibody comprising variable region sequences with substantial identity to those of G4 (Vh=SEQ ID NO:12; V1=SEQ ID NO:14);
an antibody comprising variable region sequences with substantial identity to those of M22 (Vh=SEQ ID NO:16; V1=SEQ ID NO:18);
an antibody comprising variable region sequences with substantial identity to those of M29 (Vh=SEQ ID NO:20; V1=SEQ ID NO:22);
an antibody comprising variable region sequences with substantial identity to those of M2 (Vh=SEQ ID NO:24; V1=SEQ ID NO:26);
an antibody comprising variable region sequences with substantial identity to those of M5 (Vh=SEQ ID NO:28; V1=SEQ ID NO:30);
an antibody comprising variable region sequences with substantial identity to those of G12 (Vh=SEQ ID NO:32; V1=SEQ ID NO:34)
an antibody comprising variable region sequences with substantial identity to those of M41;
an antibody comprising variable region sequences with substantial identity to those of E3;
an antibody comprising variable region sequences with substantial identity to those of B10;
an antibody comprising variable region sequences with substantial identity to those of G2;
an antibody comprising variable region sequences with substantial identity to those of G6;
an antibody comprising variable region sequences with substantial identity to those of G8;
an antibody comprising variable region sequences with substantial identity to those of G10;
an antibody comprising variable region sequences with substantial identity to those of G14;
an antibody comprising variable region sequences with substantial identity to those of G16;
an antibody comprising variable region sequences with substantial identity to those of G23;
an antibody comprising variable region sequences with substantial identity to those of G26;
an antibody comprising variable region sequences with substantial identity to those of G28; and
an antibody comprising variable region sequences with substantial identity to those of G30.

In some embodiments, the substantially identical antibody has the CDR sequences of the original antibody.

In some embodiments, the CLL-1 antibody competes for binding with an antibody selected from the group consisting of:
an antibody comprising variable region sequences of M26 (Vh=SEQ ID NO:4; V1=SEQ ID NO:6)
an antibody comprising variable region sequences of M31 (Vh=SEQ ID NO:8; V1=SEQ ID NO:10);
an antibody comprising variable region sequences of G4 (Vh=SEQ ID NO:12; V1=SEQ ID NO:14);
an antibody comprising variable region sequences of M22 (Vh=SEQ ID NO:16; V1=SEQ ID NO:18);
an antibody comprising variable region sequences of M29 (Vh=SEQ ID NO:20; V1=SEQ ID NO:22);
an antibody comprising variable region sequences of M2 (Vh=SEQ ID NO:24; V1=SEQ ID NO:26);
an antibody comprising variable region sequences of M5 (Vh=SEQ ID NO:28; V1=SEQ ID NO:30);
an antibody comprising variable region sequences of G12 (Vh=SEQ ID NO:32; V1=SEQ ID NO:34)
an antibody comprising variable region sequences of M41;
an antibody comprising variable region sequences of E3;
an antibody comprising variable region sequences of B10;
an antibody comprising variable region sequences of G2;
an antibody comprising variable region sequences of G6;
an antibody comprising variable region sequences of G8;
an antibody comprising variable region sequences of G10;
an antibody comprising variable region sequences of G14;
an antibody comprising variable region sequences of G16;
an antibody comprising variable region sequences of G23;
an antibody comprising variable region sequences of G26;
an antibody comprising variable region sequences of G28; and
an antibody comprising variable region sequences of G30.

In some embodiments, the CLL-1 antibody is selected from the group consisting of:
an antibody comprising variable region sequences of M26 (Vh=SEQ ID NO:4; V1=SEQ ID NO:6)
an antibody comprising variable region sequences of M31 (Vh=SEQ ID NO:8; V1=SEQ ID NO:10);
an antibody comprising variable region sequences of G4 (Vh=SEQ ID NO:12; V1=SEQ ID NO:14);
an antibody comprising variable region sequences of M22 (Vh=SEQ ID NO:16; V1=SEQ ID NO:18);
an antibody comprising variable region sequences of M29 (Vh=SEQ ID NO:20; V1=SEQ ID NO:22);
an antibody comprising variable region sequences of M2 (Vh=SEQ ID NO:24; V1=SEQ ID NO:26);
an antibody comprising variable region sequences of M5 (Vh=SEQ ID NO:28; V1=SEQ ID NO:30);
an antibody comprising variable region sequences of G12 (Vh=SEQ ID NO:32; V1=SEQ ID NO:34)
an antibody comprising variable region sequences of M41;
an antibody comprising variable region sequences of E3;
an antibody comprising variable region sequences of B10;
an antibody comprising variable region sequences of G2;
an antibody comprising variable region sequences of G6;
an antibody comprising variable region sequences of G8;
an antibody comprising variable region sequences of G10;
an antibody comprising variable region sequences of G14;
an antibody comprising variable region sequences of G16;
an antibody comprising variable region sequences of G23;
an antibody comprising variable region sequences of G26;
an antibody comprising variable region sequences of G28; and
an antibody comprising variable region sequences of G30.

In some embodiments, the CLL-1 antibody comprises the heavy and light chain variable region sequences of M26. In some embodiments, the CLL-1 antibody comprises the heavy and light chain variable region sequences of M31. In some embodiments, the CLL-1 antibody comprises the heavy and light chain variable region sequences of G4.

In some embodiments, the CLL-1 antibody as described binds a polypeptide consisting of the C-lectin domain of CLL-1 with a Kd at least 5-fold higher than a polypeptide consisting of the C-lectin and stalk domains of CLL-1 (e.g., any of 10, 20, 50, 100 or higher fold). In some embodiments, the CLL-1 antibody binds the C-lectin domain of CLL-1 with a Kd at least 5-fold higher than it binds full length CLL-1 extracellular domain (e.g., any of 10, 20, 50, 100 or higher fold). In some embodiments, the CLL-1 antibody as described above further binds at least 80% of the cells in a culture of HL60 cells (e.g., any of 85, 90, 95 or higher %). In some embodiments, the CLL-1 antibody as described above further binds at least 30% of the nucleated cells in a sample of AML cells from an individual with AML (e.g., any of 40, 50, 60, 70, 80, 85, 90, 95, or higher %).

In some embodiments, the CLL-1 antibody as described above is an Fv fragment (e.g., Fab, Fab', or F(ab')2). In some embodiments, the antibody comprises two distinct variable regions, with two distinct epitope binding sequences, in a single antibody construct (e.g., with one epitope binding region from M26, M31, G4, or M22 and one epitope binding region from M26, M31, G4, or M22 in any combination). In some embodiments, the CLL-1 antibody as described above is labeled, e.g., conjugated to a detectable moiety. In some embodiments, the CLL-1 as described above is attached to a therapeutic compound, e.g., a cytotoxin or cell growth inhibitor.

Further provided are pharmaceutical compositions comprising a CLL-1 antibody as described herein and a pharmaceutically acceptable excipient or carrier.

Provided are methods for determining whether a cell expresses CLL-1 comprising: contacting a CLL-1 antibody (i.e., a CLL-1 antibody having any of the activities or sequences described above) with the cell; detecting binding of the antibody to the cell, wherein binding of the antibody to the cell indicates that the cell expresses CLL-1; and determining whether the cell expresses CLL-1. In some embodiments, the method further comprises determining whether the cell expresses CD34. In some embodiments, the method further comprises determining whether the cell expresses CD38. In some embodiments, the method further comprises determining whether the cell expresses CD45. In some embodiments, the cell is in a biological sample obtained from an individual (e.g., a blood sample or a biopsy from a tumor or tissue). In some embodiments, antibody binding is detected by FACS.

Also provided are methods of identifying a myeloid cancer cell (a CLL-1 expresssing cancer cell, e.g., from a myeloproliferative disorder such as AML, CML, CMML, multiple myeloma, plasmacytoma, or MDS) or a CSC (e.g., LSC or myeloid cancer cell blast) comprising: contacting a CLL-1 antibody (i.e., a CLL-1 antibody having any of the activities or sequences described above) with a cell; detecting binding of the antibody to the cell; and identifying a CSC or myeloid cancer cell when the antibody binds the cell. In some embodiments, the myeloid cancer cell is selected from an AML, CIVIL, CMML, multiple myeloma, plasmacytoma, or MDS cell. In some embodiments, the method further comprises determining whether the cell expresses CD45 and identifying an AML cell when the cell expresses CD45. In some embodiments, the method further comprises determining whether the cell expresses CD34 and identifying a CSC when the cell expresses CD34. In some embodiments, the cell is in a biological sample from an individual. In some embodiments, antibody binding is detected by FACS.

Further provided are methods of diagnosing an individual for a myeloproliferative disorder (e.g., AML, CIVIL, MDS, CMML, multiple myeloma, plasmacytoma myelofibrosis) comprising contacting a CLL-1 antibody (i.e., a CLL-1 antibody having any of the activities or sequences described above) with a biological sample from the individual; detecting binding of the antibody to a cell in the biological sample; and diagnosing the individual with a myeloproliferative disorder when the antibody binds the cell. In some embodiments, the biological sample is a blood sample (e.g., peripheral nucleated blood cells) or biopsy from a tumor or tissue. In some embodiments, the method further comprises determining whether the cell expresses CD34. In some embodiments, the method further comprises determining a course of treatment for the individual when a myeloproliferative disorder is diagnosed. In some embodiments, the course of treatment includes administration of an effective dose of a CLL-1 antibody. In some embodiments, the effective dose of the CLL-1 antibody is administered in a pharmaceutical composition comprising a pharmaceutically acceptable excipient. In some embodiments, the method further comprises monitoring the individual, e.g., when a myeloproliferative disorder is diagnosed, or when the individual has been previously diagnosed with a myeloproliferative disorder but received treatment for the disease.

Additionally provided are methods of inhibiting survival of a CLL-1 expressing cell (e.g., reducing cell growth or division, mediating ADC, mediating CDC) comprising contacting a CLL-1 antibody (i.e., a CLL-1 antibody having any of the activities or sequences described above) with the cell and inhibiting survival of the cell. In some embodiments, the contacting comprises administering the antibody (e.g., in a pharmaceutical composition) to an individual, e.g., an individual diagnosed with a myeloproliferative disorder (e.g., AML, CIVIL, MDS, CMML, multiple myeloma, plasmacytoma myelofibrosis). In some embodiments, the CLL-1 antibody is administered in a dose effective to inhibit survival of CLL-1 expressing cells.

Provided are methods of treating a myeloproliferative disorder in an individual (e.g., reducing tumor growth or engraftment compared to an untreated control) comprising administering an effective dose of CLL-1 antibody (i.e., a CLL-1 antibody having any of the activities or sequences described above) to the individual, thereby treating the myeloproliferative disorder in the individual. In some embodiments, the myeloproliferative disorder is selected from AML, CML, MDS, CMML, multiple myeloma, plasmacytoma, and myelofibrosis. In some embodiments, the effective dose of the CLL-1 antibody is administered in a pharmaceutical composition comprising a pharmaceutically acceptable excipient. In some embodiments, the individual has been diagnosed with a myeloproliferative disorder, e.g., using a CLL-1 antibody as described herein. In some embodiments, the method of treatment further comprises monitoring cell growth (e.g., tumor growth or circulating myeloid cancer cells) in the individual, e.g., using a CLL-1 antibody as described herein. In some embodiments, the CLL-1 antibody is attached to a therapeutic compound, e.g., a cytotoxin or cell growth inhibitor.

BRIEF DESCRIPTION OF THE DRAWINGS

FIG. 1C shows the results for CLL-1 antibody clones M26, M31, and negative controls E12 (unrelated antibody) and IgG. M26 and M31 both have an EC50 between 10 and 100 ng/mL.

FIG. 4A shows that seeded CD34+ HSCs form colonies in the presence of antibody drug conjugates at a level of the negative control (no antibody or antibody drug conjugate). FIG. 4B shows that, for seeded total PBMC, AML cancer stem cells (CSCs) have 80% less colony formation in the presence of CLL-1 antibody M26 conjugated to saporin compared to the negative control (no antibody or antibody drug conjugate).

FIG. 7A shows results for mouse CLL-1 antibody clones M26, M31, and G4 (31G4) compared to a negative control mouse IgG2a. FIG. 7B shows results for the corresponding chimeric human CLL-1 antibody clones.

FIG. 9A shows the percent huCD45+CD33+ AML cells, and FIG. 9B shows the percent huCD45+ CLL-1+ AML CSCs.

FIG. 10A shows the percentage of huCD45+ CD33+ AML cells. FIG. 10B shows the $\log_{10}$ percentage of huCD45+CD33+ AML cells, to observe better resolution between the results. The data show that all 4 CLL-1 antibodies tested effectively reduced tumor burden, and that M26, ChiM26, and ChiM31 had the greatest antitumor effect.

DETAILED DESCRIPTION OF THE INVENTION

I. Introduction

Figure 1A:
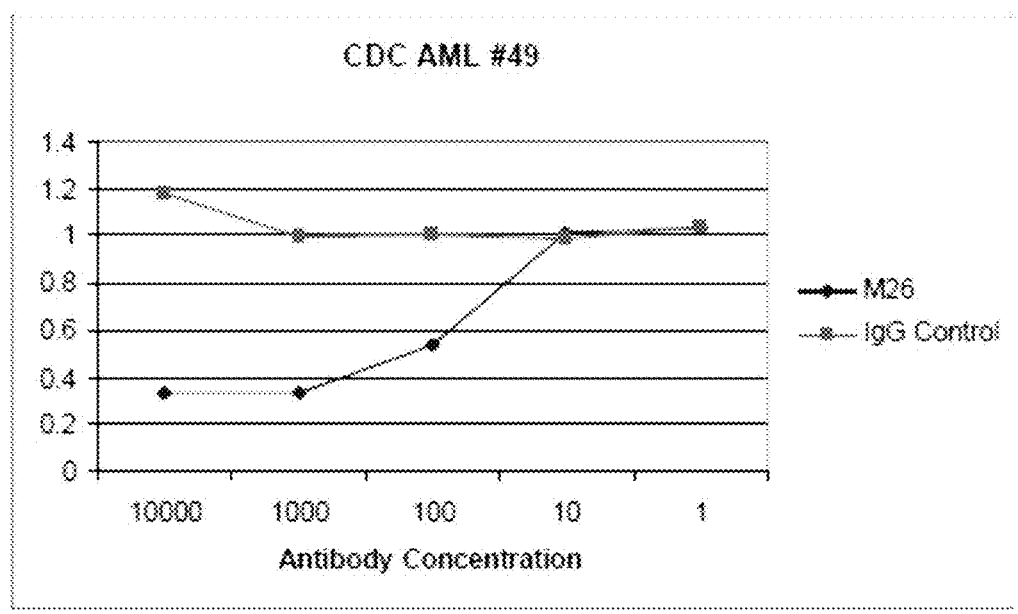
FIGS. 1A-1C show the results of complement dependent cytotoxicity (CDC) assays using primary cells from 3 different AML patients, #49 (FIG. 1A), #50 (FIG. 1B), and #52 (FIG. 1C). A and B show that CLL-1 antibody clone M26 has an EC50 between 10 and 100 ng/mL.

Provided herein are antibodies specific for CLL-1 with various advantageous properties. Such antibodies were selected based on at least one of the following criteria:

Affinity for human CLL-1 in the picomolar to nanomolar range;

Binding to a relatively high percentage of samples obtained from AML patients (e.g., a higher percentage of AML patients than the X357 or X1057 CLL-1 antibody, or at least 50% of AML patient samples);

Binding to a relatively high percentage of cells (e.g., peripheral blood mononuclear cells (PBMCs)) in an AML patient sample (e.g., a higher percentage of cells than the X357 or X1057 CLL-1 antibody, or at least 50% of the cells in an AML patient sample);

Active in antibody drug conjugate (ADC) cytotoxicity assay;

Active in complement dependent cytotoxicity (CDC) assay;

Active in antibody dependent cell cytotoxicity (ADCC) assay;

Antitumor activity, in vitro or in vivo (xenograft mouse model);

Specific binding to, and ADC activity in AML cells, but not normal HSCs;

Binding to species homolog of an animal model (e.g., cynomolgus CLL-1);

Above activities retained for antibodies in chimeric human form.

The presently described CLL-1 antibodies do not all have all of the selective characteristics, but are further described, e.g., according to sequence, below. The present CLL-1 antibodies can be used for detection of CLL-1 expressing cells, e.g., for diagnosis or monitoring of CLL-1 expressing cancer cells in an individual, or for treatment of CLL-1 expressing cancer such as AML.

II. Definitions

Unless defined otherwise, technical and scientific terms used herein have the same meaning as commonly understood by a person of ordinary skill in the art. See, e.g., Lackie, DICTIONARY OF CELL AND MOLECULAR BIOLOGY, Elsevier (4th ed. 2007); Sambrook et al., MOLECULAR CLONING, A LABORATORY MANUAL, Cold Springs Harbor Press (Cold Springs Harbor, N Y 1989). The term "a" or "an" is intended to mean "one or more." The term "comprise" and variations thereof such as "comprises" and "comprising," when preceding the recitation of a step or an element, are intended to mean that the addition of further steps or elements is optional and not excluded. Any methods, devices and materials similar or equivalent to those described herein can be used in the practice of this invention. The following definitions are provided to facilitate understanding of certain terms used frequently herein and are not meant to limit the scope of the present disclosure.

C-type Lectin-Like molecule 1 (CLL-1), also known as CLEC12A, DCAL-2, and MICL, is a type II membrane protein (ITIM domain—TM domain-stalk domain-lectin-like domain). The extracellular domain of CLL-1 is highly glycosylated, and it is expressed exclusively in cells of myeloid lineage. CLL-1 is also expressed on AML, MDS, and CIVIL cells. CLL-1 expression can be used to distinguish between normal hematopoietic stem cells (HSCs), which do not express CLL-1, and leukemic stem cells (LSCs), where it is expressed. LSCs are CD34+ cells in leukemia patients that lead to production of cancer cells and recurrence of cancer. See Bakker et al. (2004) *Cancer Res.* 64:8443.

The nucleotide and protein sequences of CLL-1 are known for many species. For example, the human sequences can be found at Genbank accession number AF247788.1 (coding sequence shown in SEQ ID NO:1) and Uniprot accession number Q5QGZ9 (SEQ ID NO:2). For the human CLL-1 protein shown as SEQ ID NO:2, the extracellular domain comprises approximately amino acids 65-265, the transmembrane domain comprises approximately amino acids 44-64, and the cytoplasmic domain comprises approximately amino acids 1-43. The stalk domain of human CLL-1 spans amino acids 65-139, and the C lectin domain spans amino acids 140-249, both with reference to the sequence shown in SEQ ID NO:2. One of skill will understand that CLL-1 variants (e.g., species homologs, allelic variants, etc.) can be optimally aligned, e.g., for identification of conserved residues and domains.

The terms "CLL-1 specific antibody," "anti-CLL-1 antibody," "CLL-1 antibody," and "anti-CLL-1" are used synonymously herein to refer to an antibody that specifically binds to CLL-1, including variously glycosylated forms of CLL-1. The CLL-1 antibodies described herein specifically bind the CLL-1 polypeptide expressed, e.g., on the surface of certain cancer cells, but not to HSCs. As discussed in more detail below, the present anti-CLL-1 antibodies can bind CLL-1 expressing cells, bind a larger percentage of AML cells compared to other AML-targeting antibodies, inhibit AML cell proliferation, and mediate their destruction.

A "CLL-1 associated disorder" (or CLL-1 related disorder, CLL-1 disorder, CLL-1 related condition or disease, etc.) refers to conditions and diseases correlated with elevated or reduced cell surface expression of CLL-1 as compared to CLL-1 expression in a standard control (e.g., a normal, non-disease, non-cancer cell). Elevated CLL-1 levels are associated with cancer cells, in particular, leukemias such as AML (acute myelogenous leukemia), MDS (myelodysplastic syndrome), and CIVIL (chronic myelogenous leukemia), and in hematopoietic CSCs (e.g., LSCs).

The term "antibody" refers to a polypeptide structure, e.g., an immunoglobulin, conjugate, or fragment thereof that retains antigen binding activity. The term includes but is not limited to polyclonal or monoclonal antibodies of the isotype classes IgA, IgD, IgE, IgG, and IgM, derived from human or other mammalian cells, including natural or genetically modified forms such as humanized, human, single-chain, chimeric, synthetic, recombinant, hybrid, mutated, grafted, and in vitro generated antibodies. The term encompases conjugates, including but not limited to fusion proteins containing an immunoglobulin moiety (e.g., chimeric or bispecific antibodies or scFv's), and fragments, such as Fab, F(ab')2, Fv, scFv, Fd, dAb and other compositions.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively. The variable region contains the antigen-binding region of the antibody (or its functional equivalent) and is most critical in specificity and affinity of binding. See Paul, *Fundamental Immunology* (2003).

Antibodies can exist as intact immunoglobulins or as any of a number of well-characterized fragments that include specific antigen-binding activity. For the sake of clarity, a tetrameric antibody with heavy and light chains is referred to herein as an "intact immunoglobulin," and can be naturally occurring, polyclonal, monoclonal, or recombinantly produced. Fragments can be produced by digestion with various peptidases. Pepsin digests an antibody below the disulfide linkages in the hinge region to produce F(ab')2, a dimer of Fab which itself is a light chain joined to $V_H$-$C_H 1$ by a disulfide bond. The F(ab')2 may be reduced under mild conditions to break the disulfide linkage in the hinge region, thereby converting the F(ab')2 dimer into an Fab' monomer. The Fab' monomer is essentially Fab with part of the hinge region. While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies or those identified using phage display libraries (see, e.g., McCafferty et al., *Nature* 348: 552-554 (1990)).

As used herein, the term "Fv" refers to a monovalent or bi-valent variable region fragment, and can encompass only the variable regions (e.g., $V_L$ and/or $V_H$), as well as longer fragments, e.g., an Fab, Fab' or F(ab')2, which also includes $C_L$ and/or $C_H 1$. Unless otherwise specified, the term "Fc" refers to a heavy chain monomer or dimer comprising $C_H 1$ and $C_H 2$ regions.

A single chain Fv (scFv) refers to a polypeptide comprising a $V_L$ and $V_H$ joined by a linker, e.g., a peptide linker. ScFvs can also be used to form tandem (or di-valent) scFvs or diabodies. Production and properties of tandem scFvs and diabodies are described, e.g., in Asano et al. (2011) *J Biol.*

*Chem.* 286:1812; Kenanova et al. (2010) *Prot Eng Design Sel* 23:789; Asano et al. (2008) *Prot Eng Design Sel* 21:597.

A "monoclonal antibody" refers to a clonal preparation of antibodies with a single binding specificity and affinity for a given epitope on an antigen. A "polyclonal antibody" refers to a preparation of antibodies that are raised against a single antigen, but with different binding specificities and affinities.

As used herein, "V-region" refers to an antibody variable region domain comprising the segments of Framework 1, CDR1, Framework 2, CDR2, and Framework 3, including CDR3 and Framework 4, which segments are added to the V-segment as a consequence of rearrangement of the heavy chain and light chain V-region genes during B-cell differentiation.

As used herein, "complementarity-determining region (CDR)" refers to the three hypervariable regions in each chain that interrupt the four "framework" regions established by the light and heavy chain variable regions. The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found.

The sequences of the framework regions of different light or heavy chains are relatively conserved within a species. The framework region of an antibody, that is the combined framework regions of the constituent light and heavy chains, serves to position and align the CDRs in three dimensional space.

The amino acid sequences of the CDRs and framework regions can be determined using various well known definitions in the art, e.g., Kabat, Chothia, international ImMunoGeneTics database (IMGT), and AbM (see, e.g., Johnson et al., supra; Chothia & Lesk, (1987)*J Mol. Biol.* 196, 901-917; Chothia et al. (1989) *Nature* 342, 877-883; Chothia et al. (1992) *J. Mol. Biol.* 227, 799-817; Al-Lazikani et al., *J. Mol. Biol* 1997, 273(4)). A helpful guide for locating CDRs using the Kabat system can be found at the website available at bioinf.org.uk/abs. Definitions of antigen combining sites are also described in the following: Ruiz et al. *Nucleic Acids Res.*, 28, 219-221 (2000); and Lefranc *Nucleic Acids Res*. January 1; 29(1):207-9 (2001); MacCallum et al., *J. Mol. Biol.*, 262: 732-745 (1996); and Martin et al, *Proc. Natl Acad. Sci. USA*, 86, 9268-9272 (1989); Martin, et al, *Methods Enzymol.*, 203: 121-153, (1991); Pedersen et al, *Immunomethods*, 1, 126, (1992); and Rees et al, In Sternberg M. J. E. (ed.), Protein Structure Prediction. Oxford University Press, Oxford, 141-172 1996).

A "chimeric antibody" refers to an antibody in which (a) the constant region, or a portion thereof, is altered, replaced or exchanged so that the antigen binding site (variable region, CDR, or portion thereof) is linked to a constant region of a different or altered class, effector function and/or species; or (b) the variable region, or a portion thereof, is altered, replaced or exchanged with a variable region having a different or altered antigen specificity (e.g., CDR and framework regions from different species). Chimeric antibodies can include variable region fragments, e.g., a recombinant antibody comprising two Fab or Fv regions or an scFv. A chimeric can also, as indicated above, include an Fc region from a different source than the attached Fv regions. In some cases, the chimeric antibody includes chimerism within the Fv region. An example of such a chimeric antibody would be a humanized antibody where the FRs and CDRs are from different sources.

Humanized antibodies are antibodies in which the antigen binding loops, i.e., CDRs, obtained from the $V_H$ and $V_L$ regions of a non-human antibody are grafted to a human framework sequence. Humanization, i.e., substitution of non-human CDR sequences for the corresponding sequences of a human antibody, can be performed following the methods described in, e.g., U.S. Pat. Nos. 5,545,806; 5,569,825; 5,633,425; 5,661,016; Riechmann et al., *Nature* 332:323-327 (1988); Marks et al., *Bio/Technology* 10:779-783 (1992); Morrison, *Nature* 368:812-13 (1994); Fishwild et al., *Nature Biotechnology* 14:845-51 (1996). Transgenic mice, or other organisms such as other mammals, may also be used to express humanized or human antibodies, as disclosed in U.S. Pat. No. 6,673,986.

The terms "antigen," "immunogen," "antibody target," "target analyte," and like terms are used herein to refer to a molecule, compound, or complex that is recognized by an antibody, i.e., can be specifically bound by the antibody. The term can refer to any molecule that can be specifically recognized by an antibody, e.g., a polypeptide, polynucleotide, carbohydrate, lipid, chemical moiety, or combinations thereof (e.g., phosphorylated or glycosylated polypeptides, etc.). One of skill will understand that the term does not indicate that the molecule is immunogenic in every context, but simply indicates that it can be targeted by an antibody.

Antibodies bind to an "epitope" on an antigen. The epitope is the localized site on the antigen that is recognized and bound by the antibody. Epitopes can include a few amino acids or portions of a few amino acids, e.g., 5 or 6, or more, e.g., 20 or more amino acids, or portions of those amino acids. In some cases, the epitope includes non-protein components, e.g., from a carbohydrate, nucleic acid, or lipid. In some cases, the epitope is a three-dimensional moiety. Thus, for example, where the target is a protein, the epitope can be comprised of consecutive amino acids, or amino acids from different parts of the protein that are brought into proximity by protein folding (e.g., a discontinuous epitope). The same is true for other types of target molecules that form three-dimensional structures.

The terms "specific for," "specifically binds," and like terms refer to a molecule (e.g., antibody or antibody fragment) that binds to a target with at least 2-fold greater affinity than non-target compounds, e.g., at least any of 4-fold, 5-fold, 6-fold, 7-fold, 8-fold, 9-fold, 10-fold, 20-fold, 25-fold, 50-fold, or 100-fold greater affinity. For example, an antibody that specifically binds a primary antibody will typically bind the primary antibody with at least a 2-fold greater affinity than a non-primary antibody target (e.g., an antibody from a different species or of a different isotype, or a non-antibody target).

The term "binds" with respect to an antibody target (e.g., antigen, analyte, immune complex), typically indicates that an antibody binds a majority of the antibody targets in a pure population (assuming appropriate molar ratios). For example, an antibody that binds a given antibody target typically binds to at least ⅔ of the antibody targets in a solution (e.g., at least any of 75, 80, 85, 90, 91, 92, 93, 94, 95, 96, 97, 98, 99, or 100%). One of skill will recognize that some variability will arise depending on the method and/or threshold of determining binding.

The term "cross-linked" with respect to an antibody refers to attachment of the antibody to a solid or semisolid matrix (e.g., sepharose, beads, culture plate), or to another protein or antibody. For example, the antibody can be multimerized to create an antibody complex with multiple (more than 2)

antigen-binding sites. The antibody can be multimerized by expressing the antibody as a high-valency isotype (e.g., IgA or IgM, which typically form complexes of 2 or 5 antibodies, respectively). Antibody multimerization can also be carried out by using a cross-linker comprising a reactive group capable of linking proteins (e.g., carbodiimide, NHS esters, etc). Methods and compositions for cross-linking an antibody to a matrix are described, e.g., in the Abcam and New England Biolab catalogs and websites (available at abcam.com and neb.com). Cross-linker compounds with various reactive groups are described, e.g., in Thermo Fisher Scientific catalog and website (available at piercenet.com).

As used herein, a first antibody, or an antigen-binding portion thereof, "competes" for binding to a target with a second antibody, or an antigen-binding portion thereof, when binding of the second antibody with the target is detectably decreased in the presence of the first antibody compared to the binding of the second antibody in the absence of the first antibody. The alternative, where the binding of the first antibody to the target is also detectably decreased in the presence of the second antibody, can, but need not be the case. That is, a second antibody can inhibit the binding of a first antibody to the target without that first antibody inhibiting the binding of the second antibody to the target. However, where each antibody detectably inhibits the binding of the other antibody to its cognate epitope or ligand, whether to the same, greater, or lesser extent, the antibodies are said to "cross-compete" with each other for binding of their respective epitope(s). Both competing and cross-competing antibodies are encompassed by the present invention. The term "competitor" antibody can be applied to the first or second antibody as can be determined by one of skill in the art. In some cases, the presence of the competitor antibody (e.g., the first antibody) reduces binding of the second antibody to the target by at least 10%, e.g., at least any of 20%, 30%, 40%, 50%, 60%, 70%, 80%, or more, e.g., so that binding of the second antibody to target is undetectable in the presence of the first (competitor) antibody.

The terms "label," "detectable moiety," and like terms refer to a composition detectable by spectroscopic, photochemical, biochemical, immunochemical, chemical, or other physical means. For example, useful labels include fluorescent dyes, luminescent agents, radioisotopes (e.g., $^{32}$P, $^{3}$H), electron-dense reagents, enzymes (e.g., as commonly used in an ELISA), biotin, digoxigenin, or haptens and proteins or other entities which can be made detectable, e.g., by incorporating a radiolabel into a peptide or antibody specifically reactive with a target analyte. Any method known in the art for conjugating an antibody to the label may be employed, e.g., using methods described in Hermanson, Bioconjugate Techniques 1996, Academic Press, Inc., San Diego. The term "tag" can be used synonymously with the term "label," but generally refers to an affinity-based moiety, e.g., a "His tag" for purification, or a "strepavidin tag" that interacts with biotin.

A "labeled" molecule (e.g., nucleic acid, protein, or antibody) is one that is bound, either covalently, through a linker or a chemical bond, or noncovalently, through ionic, van der Waals, electrostatic, or hydrogen bonds to a label such that the presence of the molecule may be detected by detecting the presence of the label bound to the molecule.

The term "differentially expressed" or "differentially regulated" refers generally to a protein or nucleic acid biomarker that is overexpressed (upregulated) or underexpressed (downregulated) in one sample compared to at least one other sample. In the context of the present disclosure, the term generally refers to overexpression of CLL-1 on a cancer cell (e.g., an AML cell or AML CSC) compared to a normal, non-cancer cell.

For example, the terms "overexpressed" or "upregulated" interchangeably refer to a protein or nucleic acid, generally a biomarker, that is transcribed or translated at a detectably greater than control level. The term includes overexpression due to transcription, post transcriptional processing, translation, post-translational processing, cellular localization (e.g., organelle, cytoplasm, nucleus, cell surface), and RNA and protein stability. Overexpression can be detected using conventional techniques for detecting biomarkers, whether mRNA (i.e., RT-PCR, hybridization) or protein (i.e., flow cytometry, imaging, ELISA, immunohistochemical techniques). Overexpression can be at least any of 10%, 20%, 30%, 40%, 50%, 60%, 70%, 80%, 90% or more in comparison to a normal cell.

The terms "agonist," "activator," "inducer" and like terms refer to molecules that increase activity or expression as compared to a control. Agonists are agents that, e.g., bind to, stimulate, increase, activate, enhance activation, sensitize or upregulate the activity of the target. The expression or activity can be increased at least any of 10%, 20%, 30%, 40%, 50%, 60%, 70%, 80%, 90% 100% or more than that in a control. In certain instances, the activation is any of 1.5-fold, 2-fold, 3-fold, 4-fold, 5-fold, 10-fold, or more in comparison to a control.

The terms "inhibitor," "repressor" or "antagonist" or "downregulator" interchangeably refer to a substance that results in a detectably lower expression or activity level as compared to a control. The inhibited expression or activity can be any of 10%, 20%, 30%, 40%, 50%, 60%, 70%, 80%, 90% or less than that in a control. In certain instances, the inhibition is any of 1.5-fold, 2-fold, 3-fold, 4-fold, 5-fold, 10-fold, or more in comparison to a control.

A "control" sample or value refers to a sample that serves as a reference, usually a known reference, for comparison to a test sample. For example, a test sample can be taken from a test condition, e.g., in the presence of a test compound, and compared to samples from known conditions, e.g., in the absence of the test compound (negative control), or in the presence of a known compound (positive control). In the context of the present disclosure, an example of a negative control would be a biological sample from a known healthy (non-cancer) individual, and an example of a positive control would be a biological sample from a known AML patient. A control can also represent an average value or a range gathered from a number of tests or results. One of skill in the art will recognize that controls can be designed for assessment of any number of parameters. For example, a control can be devised to compare therapeutic benefit based on pharmacological data (e.g., half-life) or therapeutic measures (e.g., comparison of benefit and/or side effects). Controls can be designed for in vitro applications. One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

The term "diagnosis" refers to a relative probability that a subject has a disorder such as cancer. Similarly, the term "prognosis" refers to a relative probability that a certain future outcome may occur in the subject. For example, in the context of the present disclosure, prognosis can refer to the likelihood that an individual will develop cancer, have recurrence, or the likely severity of the disease (e.g., severity of symptoms, rate of functional decline, survival, etc.). The terms are not intended to be absolute, as will be appreciated by any one of skill in the field of medical diagnostics.

"Biopsy" or "biological sample from a patient" as used herein refers to a sample obtained from a patient having, or suspected of having, a CLL-1 associated disorder. The sample can also be a blood sample or blood fraction, e.g., white blood cell fraction, serum, or plasma. In some embodiments, the sample may be a tissue biopsy, such as needle biopsy, fine needle biopsy, surgical biopsy, etc. The sample can comprise a tissue sample harboring a lesion or suspected lesion, although the biological sample may be also be derived from another site, e.g., a site of suspected metastasis, a lymph node, or from the blood. In some cases, the biological sample may also be from a region adjacent to the lesion or suspected lesion.

A "biological sample" can be obtained from a patient, e.g., a biopsy, from an animal, such as an animal model, or from cultured cells, e.g., a cell line or cells removed from a patient and grown in culture for observation. Biological samples include tissues and bodily fluids, e.g., blood, blood fractions, lymph, saliva, urine, feces, etc.

The terms "therapy," "treatment," and "amelioration" refer to any reduction in the severity of symptoms. In the case of treating cancer (e.g., AML), treatment can refer to, e.g., reducing tumor size, number of cancer cells, growth rate, metastatic activity, reducing cell death of non-cancer cells, reduced nausea and other chemotherapy or radiotherapy side effects, etc. The terms "treat" and "prevent" are not intended to be absolute terms. Treatment and prevention can refer to any delay in onset, amelioration of symptoms, improvement in patient survival, increase in survival time or rate, etc. Treatment and prevention can be complete (undetectable levels of neoplastic cells) or partial, such that fewer neoplastic cells are found in a patient than would have occurred without the present invention. The effect of treatment can be compared to an individual or pool of individuals not receiving the treatment, or to the same patient prior to treatment or at a different time during treatment. In some aspects, the severity of disease is reduced by at least 10%, as compared, e.g., to the individual before administration or to a control individual not undergoing treatment. In some aspects the severity of disease is reduced by at least 25%, 50%, 75%, 80%, or 90%, or in some cases, no longer detectable using standard diagnostic techniques.

The terms "effective amount," "effective dose," "therapeutically effective amount," etc. refer to that amount of the therapeutic agent sufficient to ameliorate a disorder, as described above. For example, for the given parameter, a therapeutically effective amount will show an increase or decrease of therapeutic effect at least any of 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least any of a 1.2-fold, 1.5-fold, 2-fold, 5-fold, or more effect over a control.

As used herein, the term "pharmaceutically acceptable" is used synonymously with physiologically acceptable and pharmacologically acceptable. A pharmaceutical composition will generally comprise agents for buffering and preservation in storage, and can include buffers and carriers for appropriate delivery, depending on the route of administration.

The terms "dose" and "dosage" are used interchangeably herein. A dose refers to the amount of active ingredient given to an individual at each administration. For the present invention, the dose can refer to the concentration of the antibody or associated components, e.g., the amount of therapeutic agent or dosage of radiolabel. The dose will vary depending on a number of factors, including frequency of administration; size and tolerance of the individual; severity of the condition; risk of side effects; the route of administration; and the imaging modality of the detectable moiety (if present). One of skill in the art will recognize that the dose can be modified depending on the above factors or based on therapeutic progress. The term "dosage form" refers to the particular format of the pharmaceutical, and depends on the route of administration. For example, a dosage form can be in a liquid, e.g., a saline solution for injection.

"Subject," "patient," "individual" and like terms are used interchangeably and refer to, except where indicated, mammals such as humans and non-human primates, as well as rabbits, rats, mice, goats, pigs, and other mammalian species. The term does not necessarily indicate that the subject has been diagnosed with a particular disease, but typically refers to an individual under medical supervision. A patient can be an individual that is seeking treatment, monitoring, adjustment or modification of an existing therapeutic regimen, etc. A "cancer patient" or "AML patient" can refer to an individual that has been diagnosed with cancer, is currently following a therapeutic regimen, or is at risk of recurrence, e.g., after surgery to remove a tumor. In some embodiments, the cancer patient has been diagnosed with cancer and is a candidate for therapy. Cancer patients can include individuals that have not received treatment, are currently receiving treatment, have had surgery, and those that have discontinued treatment.

In the context of treating cancer, a subject in need of treatment can refer to an individual that has cancer or a pre-cancerous condition, has had cancer and is at risk of recurrence, is suspected of having cancer, is undergoing standard treatment for cancer, such as radiotherapy or chemotherapy, etc.

"Cancer", "tumor," "transformed" and like terms include precancerous, neoplastic, transformed, and cancerous cells, and can refer to a solid tumor, or a non-solid cancer (see, e.g., Edge et al. *AJCC Cancer Staging Manual* ($7^{th}$ ed. 2009); Cibas and Ducatman *Cytology: Diagnostic principles and clinical correlates* ($3^{rd}$ ed. 2009)). Cancer includes both benign and malignant neoplasms (abnormal growth). "Transformation" refers to spontaneous or induced phenotypic changes, e.g., immortalization of cells, morphological changes, aberrant cell growth, reduced contact inhibition and anchorage, and/or malignancy (see, Freshney, *Culture of Animal Cells a Manual of Basic Technique* ($3^{rd}$ ed. 1994)). Although transformation can arise from infection with a transforming virus and incorporation of new genomic DNA, or uptake of exogenous DNA, it can also arise spontaneously or following exposure to a carcinogen.

The term "cancer" can refer to leukemias, carcinomas, sarcomas, adenocarcinomas, lymphomas, solid and lymphoid cancers, etc. Examples of different types of cancer include, but are not limited to, acute myelogenous leukemia (AML), chronic myelogenous leukemia (CML), B-cell lymphoma, non-Hodgkin's lymphoma, Burkitt's lymphoma, Small Cell lymphoma, Large Cell lymphoma, monocytic leukemia, myelogenous leukemia, acute lymphocytic leukemia, multiple myelomas, lung cancer (e.g., non-small cell lung cancer or NSCLC), ovarian cancer, prostate cancer, colorectal cancer, liver cancer (i.e., hepatocarcinoma), renal cancer (i.e., renal cell carcinoma), bladder cancer, breast cancer, thyroid cancer, pleural cancer, pancreatic cancer, uterine cancer, cervical cancer, testicular cancer, anal cancer, pancreatic cancer, bile duct cancer, gastrointestinal carcinoid tumors, esophageal cancer, gall bladder cancer, appendix cancer, small intestine cancer, stomach (gastric) cancer, cancer of the central nervous system, skin cancer, choriocarcinoma; head and neck cancer, osteogenic sarcoma, fibrosarcoma, neuroblastoma, glioma, and melanoma.

A "cancer target" or "cancer marker" is a molecule that is differentially expressed or processed in cancer, e.g., on a cancer cell or in the cancer milieu. Exemplary cancer targets are cell surface proteins such as CLL-1 (also, e.g., cell adhesion molecules and receptors), intracellular receptors, hormones, and molecules such as proteases that are secreted by cells into the cancer milieu. Markers for specific cancers are known in the art, e.g., CD45 for AML, CD34+CD38– for AML CSCs, MUC1 expression on colon and colorectal cancers, bombesin receptors in lung cancer, and prostate specific membrane antigen (PSMA) on prostate cancer.

In some embodiments, the cancer target can be associated with a certain type of cancer cell, e.g., AML, leukemia, myeloma, lymphoma, non-small cell lung cancer cells, prostate cancer, colorectal cancer, breast cancer or ovarian cancer. A cell type specific target is typically expressed at levels at least 2 fold greater in that cell type than in a reference population of cells. In some embodiments, the cell type specific marker is present at levels at least any of 3, 4, 5, 6, 7, 8, 9, 10, 20, 50, 100, or 1000 fold higher than its average expression in a reference population. Thus, the target can be detected or measured to distinguish the cell type or types of interest from other cells. For example, AML cancer targets include Ly86, LILRA1, and CD180.

A cancer stem cell (CSC) is a cell found in a tumor or blood cancer that can give rise to the cells that make up the bulk of the cancer. The CSC can also be self-renewing, similar to a normal (non-cancer) stem cell. CSCs can thus mediate metastasis by migrating to a non-tumor tissue in an individual and starting a "new" tumor. CSCs make up a very small percentage of any given cancer, depending on the stage that the cancer is detected. For example, the average frequency of CSCs in a sample of AML cells is believed to be about 1:10,000. Hematopoietic CSCs can be identified as CD34+, similar to normal hematopoietic stem cells (HSCs).

The terms "internalize," "internalization," "endocytose," "endocytosis," "engulf," and like terms refer to uptake of a substance by a cell, e.g., by antibody (or receptor)-mediated endocytosis or phagocytosis. The results of the ADC assays in Example 5 indicate that the presently disclosed CLL-1 antibodies can be internalized.

The terms "engraft" or "engraftment" refers to the ability of a cell to survive, proliferate, and/or properly localize upon introduction into an individual or tissue. In the case of a cancer stem cell (CSC), the term can refer to the ability of the CSC to generate a tumor de novo or to spread to a different site. The term is commonly used to describe the ability of a population of cells to survive and function in a xenograft model (e.g., engraftment of human cells in a mouse). Engraftment of hematopoietic cells can be determined as described, e.g., in WO2006/047569. Engraftment of tumor cells can be determined as described, e.g., in Beckhove et al. (2003) *Int. J. Cancer* 105:444.

The term "nucleic acid" refers to deoxyribonucleotides or ribonucleotides and polymers thereof in either single- or double-stranded form, and complements thereof. The term "polynucleotide" refers to a linear sequence of nucleotides. The term "nucleotide" typically refers to a single unit of a polynucleotide, i.e., a monomer. Nucleotides can be naturally occurring ribonucleotides or deoxyribonucleotides, or synthetic or modified versions thereof. Examples of polynucleotides contemplated herein include single and double stranded DNA, single and double stranded RNA (including siRNA), and hybrid molecules having mixtures of single and double stranded DNA and RNA.

The words "complementary" or "complementarity" refer to the ability of a nucleic acid in a polynucleotide to form a base pair with another nucleic acid in a second polynucleotide. For example, the sequence A-G-T is complementary to the sequence T-C-A. Complementarity may be partial, in which only some of the nucleic acids match according to base pairing, or complete, where all the nucleic acids match according to base pairing.

A variety of methods of specific DNA and RNA measurements that use nucleic acid hybridization techniques are known to those of skill in the art (see, Sambrook, Id.). Some methods involve electrophoretic separation (e.g., Southern blot for detecting DNA, and Northern blot for detecting RNA), but measurement of DNA and RNA can also be carried out in the absence of electrophoretic separation (e.g., quantitative PCR, dot blot, or array).

The words "protein", "peptide", and "polypeptide" are used interchangeably to denote an amino acid polymer or a set of two or more interacting or bound amino acid polymers. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

The term "amino acid" refers to naturally occurring amino acids, modified or synthetic amino acids, as well as amino acid analogs and amino acid mimetics that function similarly to naturally occurring amino acids. Naturally occurring amino acids are those encoded by the genetic code. Modified amino acids include, e.g., hydroxyproline, γ-carboxyglutamate, and 0-phosphoserine. Amino acid analogs refers to compounds that have the same basic chemical structure as a naturally occurring amino acid, e.g., an a carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated, e.g., naturally contiguous, sequences. Because of the degeneracy of the genetic code, a large number of functionally identical nucleic acids encode most proteins. For instance, the codons GCA, GCC, GCG and GCU all encode the amino acid alanine. Thus, at every position where an alanine is specified by a codon, the codon can be altered to another of the corresponding codons described without altering the encoded polypeptide. Such nucleic acid variations are "silent variations," which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, silent variations of a nucleic acid which encodes a polypeptide are implicit in a described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. The following amino acids are typically conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

The terms "identical" or "percent identity," in the context of two or more nucleic acids, or two or more polypeptides, refer to two or more sequences or subsequences that are the same or have a specified percentage of nucleotides, or amino acids, that are the same (i.e., about 60% identity, e.g., at least any of 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters, or by manual alignment and visual inspection. See e.g., the NCBI web site at ncbi.nlm.nih.gov/BLAST. Such sequences are then said to be "substantially identical." Percent identity is typically determined over optimally aligned sequences, so that the definition applies to sequences that have deletions and/or additions, as well as those that have substitutions. The algorithms commonly used in the art account for gaps and the like. Typically, identity exists over a region comprising an antibody epitope, or a sequence that is at least about 25 amino acids or nucleotides in length, or over a region that is 50-100 amino acids or nucleotides in length, or over the entire length of the reference sequence.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous," with reference to a polynucleotide or polypeptide, indicates that the polynucleotide or polypeptide comprises two or more subsequences that are not found in the same relationship to each other in nature. For instance, a heterologous polynucleotide or polypeptide is typically recombinantly produced, having two or more sequences from unrelated genes arranged to make a new functional unit, e.g., a promoter from one source and a coding region from another source. Similarly, a heterologous protein indicates that the protein comprises two or more subsequences that are not found in the same relationship to each other in nature (e.g., a fusion protein).

III. CLL-1 Associated Disorders

The presently described antibodies can be used to detect and treat CLL-1 associated disorders, i.e., diseases correlated with elevated or reduced cell surface expression of CLL-1 as compared to CLL-1 expression in a standard control (e.g., a normal, non-disease, non-cancer cell). CLL-1 expression is normally limited to myeloid lineage cells, e.g., dendritic cells, granulocytes, and monocytes in the peripheral blood and spleen. Elevated CLL-1 levels are associated with cancer, in particular, in hematopoietic CSCs (e.g., LSCs), and in myeloproliferative disorders, including leukemias such as AML (acute myelogenous or myeloproliferative leukemia), MDS (myelodysplastic syndrome), myelofibrosis, CMML (chronic myelomonocytic leukemia), multiple myeloma, plasmacytoma, and CIVIL (chronic myelogenous or myeloproliferative leukemia). See Bakker et al. (2004) Cancer Res. 64:8443; Van Rhenen et al. (2007) Blood 110:2659-66; Zhao et al. (2010) Haematologica (2010) 95:71; Van Rhenen et al. (2007) Leukemia 21:1700; and Herrmann et al. (2012) Haematologica 97:219.

AML cells can be characterized and distinguished from other cells by detecting cell surface marker expression. Aside from being CLL-1+, AML cells can be CD33+(though some are CD33-), CD45+, and CDw52+. AML blasts (including LSCs) are typically CD34+CD38-. HSCs and LSCs can be characterized by expression of CD34, but the former do not express CLL-1. MDS cells can be characterized by expression of CDS, CD7, CD13, and CD34. CIVIL cells can be characterized by expression of 7-ADD, CD33, CD34, and CD38.

Myelodysplastic Syndromes (MDS) include a group of closely-related blood formation disorders, in which the bone marrow shows qualitative and quantitative changes suggestive of a preleukemic process, but having a chronic course that does not necessarily terminate as acute leukemia. A variety of terms, including preleukemia, refractory anemia, refractory dysmyelopoietic anemia, smoldering or subacute leukemia, dysmyelopoietic syndrome (DMPS), and myelodysplasia, have all been used to describe MDS. These conditions are all characterized by a cellular marrow with impaired maturation (dysmyelopoiesis) and a reduction in the number of blood cells. DMPS is characterized by presence of megablastoids, megarkaryocyte dysplasia, and an increase in number of abnormal blast cells, reflective of enhanced granulocyte maturation process. Patients with DMPS show chromosomal abonormalities similar to those found in acute myeloid leukemia and progress to acute myeloid leukemia in a certain fraction of afflicted patients.

Chronic myeloproliferative disorders are a collection of conditions characterized by increased number of mature and immature granulocytes, erythrocytes, and platelets. Chronic myeloproliferative disorders can transition to other forms within this group, with a tendency to terminate in acute myeloid leukemia. Specific diseases within this group include polycythemia vera, chronic myeloid leukemia, agnogenic myeloid leukemia, essential thrombocythemia, and chronic neutrophilic leukemia.

Myelofibrosis is characterized by scarring of the bone marrow that results in reduced number of red and white blood cells, and platelets. Myelofibrotic scarring can result from leukemia, but can have other causes, such as thrombocytosis or adverse drug effects.

IV. CLL-1 Antibodies

Provided herein are CLL-1 antibodies (i.e., CLL-1 specific antibodies, anti-CLL-1) that specifically bind to human CLL-1, in particular to the extracellular domain of a CLL-1 expressing cell. In some embodiments, the CLL-1 antibodies bind an epitope that includes a component that is outside the C lectin domain such that the antibodies bind a polypeptide consisting of the C lectin domain with lower affinity that a polypeptide consisting of the C lectin and stalk domains of CLL-1, or the extracellular domain of CLL-1. In some embodiments, the CLL-1 antibody binds a polypeptide consisting of the C-lectin domain of CLL-1 with a Kd at least 5-fold higher than a polypeptide consisting of the C-lectin and stalk domains of CLL-1 (e.g., any of 10, 20, 50, 100 or higher fold). For example, the CLL-1 antibodies designated as M26 and M31 bind amino acids 101-265 of human CLL-1 with higher affinity than amino acids 141-265 of human CLL-1 (with reference to SEQ ID NO:2). In some embodiments, the CLL-1 antibody binds the C lectin domain with a Kd that is at least 5, 10, 20, 50, or 100-fold higher than full length CLL-1 (or the full length extracellular domain of CLL-1).

In some embodiments, the CLL-1 antibodies have an affinity for human CLL-1 with a Kd of 1000 pM or lower, e.g., any of 800 pM, 700 pM, 600 pM, 500 pM, 400 pM, 300 pM, 200 pM, 100 pM, or lower. In some embodiments, the CLL-1 antibodies have an affinity for human CLL-1 with a Kd of 10 nM or lower, e.g., 1 nM or lower, 1-10 nM, 100-1000 pM, 10-1000 pM, about 1 nM or lower, 1-500 pM. In some embodiments, the CLL-1 antibodies also bind to primate CLL-1, e.g., cynomolgus CLL-1, with Kd that is 10 nM, 1 nM, 500 pM or less. In some embodiments, the CLL-1 antibodies bind cynomolgus CLL-1 with a Kd that is within an order of magnitude of the Kd for human CLL-1. One of skill will understand that lower Kd values indicate higher affinity.

In some embodiments, the CCL-1 antibodies bind a broad range of CLL-1 glycosylation variants. In some embodiments, the CLL-1 antibodies bind a form (e.g., a glycosylation variant) of CLL-1 that is expressed on AML cells. For example, the presently described CLL-1 antibodies can bind at least any of 65, 70, 75, 80, 85, 90, 95 or higher percent of the cells in an AML cell culture (e.g., HL60, THP1, and U937 cell lines). In some embodiments, the CLL-1 antibodies can bind at least any of 50, 60, 65, 70, 75, 80, 85, 90, 95 or higher percent of the cells in an AML patent sample (e.g., a PBMC sample or biopsy from an AML patient). One of skill will understand that, in such a cell binding assay, that an appropriate concentration of antibody is added, e.g., so that there are sufficient antibody molecules present to bind the number of cells in the culture or sample.

Surprisingly, CLL-1 antibodies described herein can inhibit growth of CLL-1-expressing cells in vitro and in vivo even in the absence of a conjugated cytotoxic agent. Given the high percentage of binding to AML cells from patient samples, the presently described antibodies provide a useful therapeutic option for AML patients, as well as those suffering from CLL-1+ MDS or CML.

The CLL-1 antibodies described herein also show complement dependent cytotoxicity (CDC) activity (see, e.g., FIGS. 1A-1C) and antibody drug conjugate (ADC) activity (see Example 5). These CLL-1 antibodies can also thus be used to target CLL-1 expressing cells for destruction, e.g. in the absence of a conjugated cytotoxic agent.

CLL-1 antibodies described herein have unique cell binding activities compared to previously characterized antibodies. For example, the presently described antibodies bind an epitope that is present on a higher percentage of primary cells from AML patients. These antibodies can be used for detecting cancer cells that display an epitope that is targeted with high affinity by at least one of the CLL-1 antibodies disclosed herein. In some embodiments, those cancer cells can then be targeted for destruction with the same CLL-1 antibody. Such methods can include treating an individual having CLL-1 expressing cancer cells comprising administering the CLL-1 antibody to the individual.

In some embodiments, the invention includes CLL-1 antibodies that compete for binding to CLL-1 with a competitor antibody selected from the group consisting of:
  an antibody having the CDR sequences of M26 (see Example 1, Table 3)
  an antibody having the CDR sequences of M31;
  an antibody having the CDR sequences of G4;
  an antibody having the CDR sequences of M22;
  an antibody having the CDR sequences of M29;
  an antibody having the CDR sequences of M2;
  an antibody having the CDR sequences of M5; and
  an antibody having the CDR sequences of G12.

In some embodiments, the CLL-1 antibodies competes for binding to CLL-1 with an antibody selected from the group consisting of:
  an antibody comprising variable region sequences with substantial identity (at least (85, 90, 95, or 98% identity) to those of M26 (Vh=SEQ ID NO:4; Vl=SEQ ID NO:6)
  an antibody comprising variable region sequences with substantial identity to those of M31 (Vh=SEQ ID NO:8; Vl=SEQ ID NO:10);
  an antibody comprising variable region sequences with substantial identity to those of G4 (Vh=SEQ ID NO:12; Vl=SEQ ID NO:14);
  an antibody comprising variable region sequences with substantial identity to those of M22 (Vh=SEQ ID NO:16; Vl=SEQ ID NO:18);
  an antibody comprising variable region sequences with substantial identity to those of M29 (Vh=SEQ ID NO:20; Vl=SEQ ID NO:22);
  an antibody comprising variable region sequences with substantial identity to those of M2 (Vh=SEQ ID NO:24; Vl=SEQ ID NO:26);
  an antibody comprising variable region sequences with substantial identity to those of M5 (Vh=SEQ ID NO:28; Vl=SEQ ID NO:30); and
  an antibody comprising variable region sequences with substantial identity to those of G12 (Vh=SEQ ID NO:32; Vl=SEQ ID NO:34). In some embodiments, the substantially identical antibody has the same heavy and light chain CDR sequences as the original antibody.

Numerous types of competitive binding assays are known, including solid phase direct or indirect radioimmunoassay (RIA); solid phase direct or indirect enzyme immunoassay (EIA), sandwich competition assay (see Stahli et al., *Methods in Enzymology* 9:242-253 (1983)); solid phase direct biotin-avidin EIA (see Kirkland et al., *J. Immunol.* 137:3614-3619 (1986)); solid phase direct labeled assay;

solid phase direct labeled sandwich assay (see Harlow and Lane, *Antibodies, A Laboratory Manual*, Cold Spring Harbor Press (1988)); solid phase direct label RIA using I-125 label (see Morel et al., *Molec. Immunol.* 25(1):7-15 (1988)); solid phase direct biotin-avidin EIA (Cheung et al., *Virology* 176:546-552 (1990)); and direct labeled RIA (Moldenhauer et al., *Scand. J. Immunol.* 32:77-82 (1990)). Typically, such an assay involves the use of purified antigen bound to a solid surface or cells bearing either of these, an unlabelled test immunoglobulin and a labeled reference immunoglobulin. Competitive inhibition is measured by determining the amount of label bound to the solid surface or cells in the presence of the test immunoglobulin. Usually the test immunoglobulin is present in excess. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Usually, when a competing antibody is present in excess, it will inhibit specific binding of a reference antibody to a common antigen by at least 50 or 75%.

In some embodiments, the CLL-1 antibody binds the same epitope as an antibody selected from the group consisting of:
  an antibody having the CDR sequences of M26 (see Example 1, Table 3)
  an antibody having the CDR sequences of M31;
  an antibody having the CDR sequences of G4;
  an antibody having the CDR sequences of M22;
  an antibody having the CDR sequences of M29;
  an antibody having the CDR sequences of M2;
  an antibody having the CDR sequences of M5; and
  an antibody having the CDR sequences of G12.

In some embodiments, the CLL-1 antibody has light chain CDR sequences and heavy chain CDR sequences having up to 1, 2, or 3 amino acid substitutions, additions, or deletions/CDR relative to the CDR sequences of an antibody selected from the group consisting of M26, M31, G4, M22, M29, M2, M5, and G12. In some embodiments, the light chain CDR sequences include up to 1, 2, or 3 amino acid substitutions, additions or deletions/CDR relative to the light chain CDR sequences of the aforementioned CLL-1 antibodies. In some embodiments, the heavy chain CDR sequences include up to 1, 2, or 3 amino acid substitutions, additions, or deletions/CDR relative to the heavy chain CDR sequences of the aforementioned CLL-1 antibodies. In some embodiments, substitution, addition or deletion occurs in only 1, 2, 3, 4, or 5 CDRs of the 6 total CDRs.

In some embodiments, the CLL-1 antibody is selected from the group consisting of:
  an antibody having the CDR sequences of M26 (see Example 1, Table 3);
  an antibody having the CDR sequences of M31;
  an antibody having the CDR sequences of G4;
  an antibody having the CDR sequences of M22;
  an antibody having the CDR sequences of M29;
  an antibody having the CDR sequences of M2;
  an antibody having the CDR sequences of M5; and
  an antibody having the CDR sequences of G12. In some embodiments, any one or more of the CDR sequences includes 1, 2, or 3 conservative amino acid substitutions compared to the original antibody CDR sequences.

In some embodiments, the CLL-1 antibody is selected from the group consisting of:
  an antibody comprising variable region sequences with substantial identity (at least (85, 90, 95, or 98% identity) to those of M26 (Vh=SEQ ID NO:4; Vl=SEQ ID NO:6)
  an antibody comprising variable region sequences with substantial identity to those of M31 (Vh=SEQ ID NO:8; Vl=SEQ ID NO:10);
  an antibody comprising variable region sequences with substantial identity to those of G4 (Vh=SEQ ID NO:12; Vl=SEQ ID NO:14);
  an antibody comprising variable region sequences with substantial identity to those of M22 (Vh=SEQ ID NO:16; Vl=SEQ ID NO:18);
  an antibody comprising variable region sequences with substantial identity to those of M29 (Vh=SEQ ID NO:20; Vl=SEQ ID NO:22);
  an antibody comprising variable region sequences with substantial identity to those of M2 (Vh=SEQ ID NO:24; Vl=SEQ ID NO:26);
  an antibody comprising variable region sequences with substantial identity to those of M5 (Vh=SEQ ID NO:28; Vl=SEQ ID NO:30); and
  an antibody comprising variable region sequences with substantial identity to those of G12 (Vh=SEQ ID NO:32; Vl=SEQ ID NO:34).

In some embodiments, the antibody also has at least one activity selected from
  Binding to human CLL-1 with a Kd of 10 nM or lower, e.g., 1 nM or lower, 1-10 nM, 100-1000 pM, 10-1000 pM, about 1 nM or lower, 1-500 pM, etc.;
  An EC50 of 200 ng/ml or less in a CDC assay with HL60 cells or CLL-1 expressing AML cells from an AML patient;
  An EC50 of 100 pM of less in a ADC assay with HL60 cells or CLL-1 expressing AML cells from an AML patient; and
  Reducing cell growth of CLL-1-expressing cells (e.g., HL60, AML cells), compared to cell growth in the absence of the antibody.

Any of the antibodies described herein can be a chimeric antibody or a humanized antibody. In some embodiments, the antibody is a CLL-1-binding antibody fragment, e.g., an Fab. In some embodiments, the CLL-1 antibody is labeled with a detectable agent, e.g., as described below. In some embodiments, the CLL-1 antibody is attached to a therapeutic agent, e.g., a chemotherapeutic or cytotoxic agent as described below.

A. Methods of Making Antibodies

For preparation of the presently described antibodies, e.g., recombinant, monoclonal, or polyclonal antibodies, many techniques known in the art can be used (see, e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy*, Alan R. Liss, Inc. (1985); Coligan, *Current Protocols in Immunology* (1991); Harlow & Lane, *Antibodies, A Laboratory Manual* (1988); and Goding, *Monoclonal Antibodies: Principles and Practice* (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, *Immunology* (3$^{rd}$ ed. 1997)). Techniques for the production of single chain antibodies or recombinant antibodies (U.S. Pat. Nos. 4,946,778, 4,816,567) can be adapted to produce antibodies to polypeptides of this invention. Also, transgenic mice, or other organisms such as other mammals, can be used to express humanized or human antibodies (see, e.g., U.S. Pat. Nos. 5,545,807; 5,545,806; 5,569,825; 5,625,126; 5,633,425; 5,661,016, Marks et al., *Bio/Technology* 10:779-783 (1992); Lonberg et al., *Nature* 368:856-859 (1994); Morrison, *Nature* 368:812-13 (1994); Fishwild et al., *Nature Biotechnology* 14:845-51 (1996); *Neuberger, Nature Biotechnology* 14:826 (1996); and Lonberg & Huszar, *Intern. Rev. Immunol.* 13:65-93 (1995)). Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)). Antibodies can also be made bispecific, i.e., able to recognize two different antigens (see, e.g., WO 93/08829, Traunecker et al., *EMBO J.* 10:3655-3659 (1991); and Suresh et al., *Methods in Enzymology* 121:210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Antibodies can be produced using any number of expression systems, including prokaryotic and eukaryotic expression systems. In some embodiments, the expression system is a mammalian cell expression, such as a hybridoma, or a CHO cell expression system. Many such systems are widely available from commercial suppliers. In embodiments in which an antibody comprises both a $V_H$ and $V_L$ region, the $V_H$ and $V_L$ regions may be expressed using a single vector, e.g., in a di-cistronic expression unit, or under the control of different promoters. In other embodiments, the $V_H$ and $V_L$ region may be expressed using separate vectors. A $V_H$ or $V_L$ region as described herein may optionally comprise a methionine at the N-terminus.

An antibody of the invention can also be produced in various formats, including as a Fab, a Fab', a F(ab')2, a scFv, or a dAB. The antibody fragments can be obtained by a variety of methods, including, digestion of an intact antibody with an enzyme, such as pepsin (to generate $(Fab')_2$ fragments) or papain (to generate Fab fragments); or de novo synthesis. Antibody fragments can also be synthesized using recombinant DNA methodology. In some embodiments, the CLL-1 antibody comprises $F(ab')_2$ fragments that specifically bind CLL-1. An antibody of the invention can also include a human constant region. See, e.g., Fundamental Immunology (Paul ed., 4d ed. 1999); Bird, et al., *Science* 242:423 (1988); and Huston, et al., *Proc. Natl. Acad. Sci. USA* 85:5879 (1988).

Methods for humanizing non-human antibodies (i.e., using CDRs from non-human antibodies) are also known in the art. Generally, a humanized antibody has one or more amino acid residues from a source which is non-human. These non-human amino acid residues are often referred to as import residues, which are typically taken from an import variable domain. Humanization can be essentially performed following the method of Winter and co-workers (see, e.g., Jones et al., *Nature* 321:522-525 (1986); Riechmann et al., *Nature* 332:323-327 (1988); Verhoeyen et al., *Science* 239:1534-1536 (1988) and Presta, *Curr. Op. Struct. Biol.* 2:593-596 (1992)), by substituting rodent CDRs or CDR sequences for the corresponding sequences of a human antibody. Such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

In some cases, the antibody or antibody fragment can be conjugated to another molecule, e.g., polyethylene glycol (PEGylation) or serum albumin, to provide an extended half-life in vivo. Examples of PEGylation of antibody fragments are provided in Knight et al. *Platelets* 15:409, 2004 (for abciximab); Pedley et al., *Br. J. Cancer* 70:1126, 1994 (for an anti-CEA antibody); Chapman et al., *Nature Biotech.* 17:780, 1999; and Humphreys, et al., *Protein Eng. Des.* 20:227, 2007). The antibody or antibody fragment can also be labeled, or conjugated to a therapeutic agent as described below.

B. Binding Affinity

The specificity of the binding can be defined in terms of the comparative dissociation constants (Kd) of the antibody (or other targeting moiety) for target, as compared to the dissociation constant with respect to the antibody and other materials in the environment or unrelated molecules in general. Typically, the Kd for the antibody with respect to the unrelated material will be at least 2-fold, 3-fold, 4-fold, 5-fold, 10-fold, 20-fold, 50-fold, 100-fold, 200-fold or higher than Kd with respect to the target.

The desired affinity for an antibody, e.g., high (pM to low nM), medium (low nM to 100 nM), or low (about 100 nM or higher), may differ depending upon whether it is being used as a diagnostic or therapeutic. Without being limited to theory, in one example, an antibody with medium affinity may be more successful in localizing to a tumor as compared to one with a high affinity. Thus, antibodies having different affinities can be used for diagnostic and therapeutic applications.

A targeting moiety will typically bind with a Kd of less than about 1000 nM, e.g., less than 250, 100, 50, 20 or lower nM. In some embodiments, the Kd of the affinity agent is less than 15, 10, 5, or 1 nM. In some embodiments, the Kd is 1-100 nM, 0.1-50 nM, 0.1-10 nM, or 1-20 nM. The value of the dissociation constant (Kd) can be determined by well-known methods, and can be computed even for complex mixtures by methods as disclosed, e.g., in Caceci et al., Byte (1984) 9:340-362.

Affinity of an antibody, or any targeting agent, for a target can be determined according to methods known in the art, e.g., as reviewed in Ernst et al. Determination of Equilibrium Dissociation Constants, *Therapeutic Monoclonal Antibodies* (Wiley & Sons ed. 2009).

Quantitative ELISA, and similar array-based affinity methods can be used. ELISA (Enzyme linked immunosorbent signaling assay) is an antibody-based method. In some cases, an antibody specific for target of interest is affixed to a substrate, and contacted with a sample suspected of containing the target. The surface is then washed to remove unbound substances. Target binding can be detected in a variety of ways, e.g., using a second step with a labeled antibody, direct labeling of the target, or labeling of the primary antibody with a label that is detectable upon antigen binding. In some cases, the antigen is affixed to the substrate (e.g., using a substrate with high affinity for proteins, or a Strepavidin-biotin interaction) and detected using a labeled antibody (or other targeting moiety). Several permutations of the original ELISA methods have been developed and are known in the art (see Lequin (2005) *Clin. Chem.* 51:2415-18 for a review).

The Kd, Kon, and Koff can also be determined using surface plasmon resonance (SPR), e.g., as measured by using a Biacore T100 system. SPR techniques are reviewed, e.g., in Hahnfeld et al. Determination of Kinetic Data Using SPR Biosensors, *Molecular Diagnosis of Infectious Diseases* (2004). In a typical SPR experiment, one interactant (target or targeting agent) is immobilized on an SPR-active, gold-coated glass slide in a flow cell, and a sample containing the other interactant is introduced to flow across the surface. When light of a given frequency is shined on the surface, the changes to the optical reflectivity of the gold indicate binding, and the kinetics of binding.

Binding affinity can also be determined by anchoring a biotinylated interactant to a streptaviden (SA) sensor chip. The other interactant is then contacted with the chip and detected, e.g., as described in Abdessamad et al. (2002) *Nuc. Acids Res.* 30:e45.

C. Determining CLL-1 Epitope

The site of antibody binding to CLL-1 can be mapped using known techniques for epitope mapping. One of skill will appreciate that the approach used for epitope mapping can vary depending on the antigen, e.g., where it is expressed in the cell, post-translational modifications of the primary polypeptide sequence, and differences between antigen structure on different cells or in different environments. CLL-1 is a transmembrane protein with approximately 200 extracellular amino acids. The extracellular domain is glycosylated, and includes a C lectin domain. The epitope for a CLL-1 antibody can be determined or partially determined by varying the primary sequence or glycosylation state of CLL-1, and comparing the affinity of the CLL-1 antibody to the different variants of CLL-1.

Such epitope mapping can be carried out in vitro, e.g., by screening phage display libraries or synthetic peptide libraries, e.g., using beads or other solid matrices. Linear epitopes are typically about six amino acids, though this can vary somewhat. In order to mimic linear epitopes present in a protein, synthetic peptides can be made corresponding to the sequence. In some embodiments, this sequence is extended on the N and/or C terminals to provide additional amino acid residues that are present in the flanking sequences in the protein. This can more closely mimic the primary, and to a certain extent, the secondary structure environment of the epitope. Additionally, residues including but not limited to one or more glycines or gamma amino butyric acid, can be appended to either terminus to provide a spacer to minimize steric interactions with, for example, a solid phase used in an immunoassay. Spacer length is often varied to determine empirically the best structure.

Because of the variable nature of the epitope and the potential effects due to the flanking sequences, in some embodiments, one can use peptides that vary in length by extending the N or C terminals by a certain number of residues. Another approach utilizes repeating peptide epitopes, or alternating epitopes with intervening spacer residues. The length of these peptides is often varied according to the number of repeating units desired.

One approach for epitope mapping is to synthesize overlapping peptides, for example 20 residues in length, with a six residue overlap, which cover the primary sequence of the CLL-1 extracellular region. If such peptide screening is used to map the epitope, peptides can be modified to overcome the undesirable interactions with solid phase supports used in immunoassays. One way is to substitute hydrophobic residues in the peptide with hydrophilic ones, in order to reduce or minimize the hydrophobic interactions, and increased peptide accessibility. Similarly, charged peptide residues can be substituted with noncharged residues to eliminate ionic interactions with the solid phase. Peptides can also be modified by adding spacer groups of a variety of structures to position the peptide epitope further from the solid phase and minimize steric hindrance.

Peptides can be synthesized to reflect post-translational modifications that are present on the native protein, or the native protein on targeted cells. Modifications include but are not limited to glycosylation and phosphorylation at specific sites in the protein.

Another approach for determining the epitope is to express CLL-1 variants in cells, and compare CLL-1 antibody affinities between the different variants. The CLL-1 variants can be designed as described for the peptide studies. In addition, glycosylated residues (e.g., asparagine, arginine, serine, threonine, tyrosine) can be substituted to determine whether the epitope includes a glycosylation site. Similarly, phosphorylated residues (serine, threonine, tyrosine) can be substituted.

The epitope can also be determined or partially determined by comparing antibody affinity for different types of CLL-1 expressing cells. For example, antibody affinity can be determined and compared for primary AML cells, e.g., AML blasts and engrafted AML tumor cells; for AML cell lines, for other non-cancerous myeloid cells, etc.

D. CDC, ADCC, and ADC Assays

The presently described antibodies are effective for Cell dependent cytotoxicity (CDC), Antibody dependent cell-mediated cytotoxicity (ADCC), and Antibody drug conjugate cytotoxicity (ADC) of cells that express CLL-1. Exemplary cells that express CLL-1 include cell lines that express heterologous, recombinant CLL-1 (e.g., human CLL-1); human AML cell lines such as HL60, THP1, TF1-alpha, U937, and OCI AML-5 (the first four of which are available from ATCC); primary cells from one or more AML patients (e.g., PBMC or engrafted tumor cells); human CML cell lines such as K562 and KU812 (available from ATCC); and primary cells from one or more CIVIL or MDS patients.

An antibody is described as having CDC activity and mediating CDC if it results in complement dependent killing of cells that express the antibody target. CDC assays are known in the art, and are described, e.g., in Gazzano-Santoro et al. (1997) *J. Immunol. Methods* 202:163; Idusogie et al. (2000) 1 *Immunol.* 164:4178; and in Example 6 below. CDC kits and services are commercially available, e.g. from GeneScript® and Cell Technology Inc.

In brief, the assay is typically carried out in vitro, and includes antibody binding to a cell expressing the antibody target on its surface. Complement components, including Clq which binds to the Ch region of the antibody, are added. The complement components then interact to kill the targeted cell. CDC is measured after a period of incubation of generally between 4 and 24 hours, for example, by determining the release of intracellular enzyme or granules known to be present in the targeted cell, by comparing the starting and ending target cell population, etc.

An antibody is described as having ADCC activity and mediating ADCC if it results in killing of antibody-bound cells (e.g., CLL-1 expressing cells) by effector cells. Effector cells are typically natural killer cells, but can also be macrophages, neutrophils, or eosinophils. Genetically engineered effector cell lines have also been developed for use in ADCC assays (see, e.g., Schnueriger et al. (2011) *Mol. Immunol.* 48:1512). ADCC assays are known in the art, and are described, e.g., in Perussia and Loza (2000) *Methods in Mol. Biol.* 121:179; Bretaudeau and Bonnaudet (2011) *BMC Proceedings* 5(Suppl 8):P63; and in Example 12 below.

ADCC kits and services are commercially available, e.g. from GeneScript® and Promega®.

In brief, the assay is typically carried out in vitro, and includes antibody binding to a cell expressing the antibody target on its surface. Effector cells are added that recognize antibody-bound cells, typically through an Fc receptor such as CD16. The effector cells kill the antibody-bound cell, e.g., by releasing cytotoxins that cause apoptosis. Cell death is detected by release of a detectable element within the target cells (e.g., Cr51) or by detection of an element involved in the cell mediated toxicity (e.g., activation of NFAT signaling in effector cells).

An antibody is described as having antibody-drug conjugate (ADC) activity (or mediating ADC) if the antibody, when conjugated with a cytotoxic agent (drug), results in killing (inhibiting survival) a cell that expresses the target of the antibody, in this case, CLL-1. Appropriate cytotoxic agents are known in the art, e.g., saporin, doxorubicin, daunomycin, *vinca*-alkaloids, taxoids, tubulin agents (e.g., Maytansin, auristatin), and DNA agents (e.g., calicheamicin, duocarmycin, pyrrolobenzodiazepine dimers), etc. ADC assays are known in the art, e.g., as described in Gerber et al. (2009) 3:247, and in the Examples below.

E. Internalization

The CLL-1 antibodies described herein can be internalized into CLL-1-expressing cells, including CLL-1 AML cells. That is, a CLL-1 expressing cell can internalize the antibodies described herein. The CLL-1 antibodies described herein provide an effective means for targeting such cells, e.g., with detectable or cytotoxic conjugates.

The percent internalization and internalization rate of an antibody can be evaluated by using methods known in the art, including, e.g., flow cytometry (FACS) and confocal fluorescent microscopy. Such methods are described, e.g., in Lue et al. (2007) *Nature Protocols* (*Nature Med.* 13:587-96); Cho et al. (2010) *Biomacromolecules* and Corbani et al. (2004) *Endocrinology* 145:2876-85, and as described herein.

For FACS and confocal microscopy, cells are incubated with a fluorescently-labeled targeting agent, e.g., antibody. The cells are typically selected to express the target of the labeled antibody, e.g., CLL-1. Control cells can then be used that do not express the target. Internalization typically occurs at 37° C., but not at 4° C., which provides another control for the reaction. The cells can thus be contacted with the labeled agent and incubated at 37° C. or 4° C. (e.g., to detect binding without internalization).

Unbound, and surface-bound agent is removed by washing the cells, e.g., in an acid wash, followed by wash with a buffer at normal pH.

If adherent cells are used, the cells are removed from substrate prior to flow cytometry. The percentage of fluorescent cells indicates the percent internalization of the fluorescently-labeled agent. Percent internalization can also be expressed, e.g., as a percent of initial labeled agent added to the cells.

Internalization of an agent can also be evaluated by determining the localization of the fluorescently labeled agent by confocal microscopy. Methods of using confocal microscopy to determine internalization are described in, e.g., Xiao et al. (2008) *Chem. Eur.* 1, 14:1769-1775. Briefly, the cells are contacted with labeled agent and incubated as described above. Following incubation, the cells can be incubated on ice, washed in PBS buffer at 4° C., treated with 0.25% trypsin (to remove from substrate, if applicable). The cell suspension can then be applied to slides for confocal fluorescent microscopy. Suitable confocal microscopes include the FV500-IX81 confocal microscope (Olympus America Inc.; Center Valley, Pa.) and Eclipse Ti-E (Nikon Instruments Inc.; Melville, N.Y.).

V. Diagnostic Applications

The CLL-1 antibodies described herein specifically bind CLL-1-expressing cells. CLL-1 antibodies can thus be used for in vitro and in vivo diagnostic assays to detect CLL-1-expressing cells (e.g., AML cells and AML CSCs). For example, a sample (e.g., blood sample or tissue biopsy) can be obtained from a patient and contacted with a CLL-1 antibody, and the presence of a CLL-1-expressing cell in the patient sample can be determined by detecting antibody binding. Antibody binding can be detected directly (e.g., where the antibody itself is labeled) or by using a second detection agent, such as a secondary antibody. The detectable label can be associated with an antibody of the invention, either directly, or indirectly, e.g., via a chelator or linker.

In some embodiments, the CLL-1 antibody is contacted with a biological sample from an individual having or suspected of having a CLL-1 associated disorder, and antibody binding to a cell in the sample is determined, wherein higher or lower than normal antibody binding indicates that the individual has a CLL-1 associated disorder. In some embodiments, the biological sample is a blood sample or blood fraction (e.g., serum, plasma, platelets, red blood cells, white blood cells, PBMCs). In some embodiments, the biological sample is a tissue sample (biopsy), e.g., from a suspected tumor site, or from a tissue that is known to be affected, e.g., to determine the boundaries of a known tumor.

Biopsies are typically performed to obtain samples from tissues, i.e., non-fluid cell types. The biopsy technique applied will depend on the tissue type to be evaluated (e.g., breast, skin, colon, prostate, kidney, lung, bladder, lymph node, liver, bone marrow, airway or lung). In the case of a cancer the technique will also depend on the size and type of the tumor (e.g., solid, suspended, or blood), among other factors. Representative biopsy techniques include, but are not limited to, excisional biopsy, incisional biopsy, needle biopsy, surgical biopsy, and bone marrow biopsy. An "excisional biopsy" refers to the removal of an entire tumor mass with a small margin of normal tissue surrounding it. An "incisional biopsy" refers to the removal of a wedge of tissue that includes a cross-sectional diameter of the tumor. A diagnosis or prognosis made by endoscopy or fluoroscopy can require a "core-needle biopsy" of the tumor mass, or a "fine-needle aspiration biopsy" which generally obtains a suspension of cells from within the tumor mass. Biopsy techniques are discussed, for example, in *Harrison's Principles of Internal Medicine*, Kasper, et al., eds., 16th ed., 2005, Chapter 70, and throughout Part V.

Any method of detecting antibody binding to a cell in a sample can be used for the present diagnostic assays. Methods of detecting antibody binding are well known in the art, e.g., flow cytometry, fluorescent microscopy, ELISAs, etc. In some embodiments, the method comprises preparing the biological sample for detection prior to the determining step. For example, a subpopulation of cells (e.g., white blood cells, CD34+ cells, CD45+ cells, etc.) can be separated from the rest of the sample from the individual (e.g., other blood components) or cells in a tissue can be suspended for easier detection.

In some embodiments, the percentage of CLL-1-expressing cells in the sample is determined and compared to a control, e.g., a sample from an individual or group of individuals that are known to have a CLL-1 associated disorder (positive control) or from an individual or group of individuals that are known not to have a CLL-1 associated disorder (normal, healthy, non-disease, or negative control). In some embodiments, the control is a standard range of CLL-1 expression established for a given tissue. A higher or lower than normal percentage of CLL-1 expressing cells, or higher or lower expression level, indicates that the individual has a CLL-1 associated disorder.

In some embodiments, a labeled CLL-1 antibody can be provided (administered) to an individual to determine the applicability of an intended therapy. For example, a labeled antibody may be used to detect CLL-1 density within a diseased area, where the density is typically high relative to non-diseased tissue. A labeled antibody can also indicate that the diseased area is accessible for therapy. Patients can thus be selected for therapy based on imaging results. Anatomical characterization, such as determining the precise boundaries of a cancer, can be accomplished using standard imaging techniques (e.g., CT scanning, MM, PET scanning, etc.).

In some embodiments, labeled CLL-1 antibodies as described herein can be further associated with a therapeutic compound, e.g., to form a "theranostic" composition. For example, an CLL-1 antibody can be linked (directly or indirectly) to both a detectable label and a therapeutic agent, e.g., a cytotoxic agent to kill CLL-1-expressing cancer cells. In some embodiments, a labeled CLL-1 antibody is used for diagnosis and/or localization of a CLL-1 expressing cancer cell, and the CLL-1 expressing cancer cell is then targeted with a separate therapeutic CLL-1 specific antibody. In some embodiments, the diagnostic CLL-1 specific antibody is one that is not internalized into CLL-1-expressing cells at a high rate or percentage.

In some embodiments, the therapeutic CLL-1 antibody is internalized into CLL-1-expressing cells at a high rate or percentage.

A. Labels

A diagnostic agent comprising a CLL-1 antibody can include any diagnostic agent known in the art, as provided, for example, in the following references: Armstrong et al., *Diagnostic Imaging*, 5$^{th}$ Ed., Blackwell Publishing (2004); Torchilin, V. P., Ed., *Targeted Delivery of Imaging Agents*, CRC Press (1995); Vallabhajosula, S., *Molecular Imaging: Radiopharmaceuticals for PET and SPECT*, Springer (2009). A diagnostic agent can be detected by a variety of ways, including as an agent providing and/or enhancing a detectable signal. Detectable signals include, but are not limited to, gamma-emitting, radioactive, echogenic, optical, fluorescent, absorptive, magnetic, or tomography signals. Techniques for imaging the diagnostic agent can include, but are not limited to, single photon emission computed tomography (SPECT), magnetic resonance imaging (MRI), optical imaging, positron emission tomography (PET), computed tomography (CT), x-ray imaging, gamma ray imaging, and the like. The terms "detectable agent," "detectable moiety," "label," "imaging agent," and like terms are used synonymously herein.

In some embodiments, the label can include optical agents such as fluorescent agents, phosphorescent agents, chemiluminescent agents, and the like. Numerous agents (e.g., dyes, probes, labels, or indicators) are known in the art and can be used in the present invention. (See, e.g., Invitrogen, The Handbook—A Guide to Fluorescent Probes and Labeling Technologies, Tenth Edition (2005)). Fluorescent agents can include a variety of organic and/or inorganic small molecules or a variety of fluorescent proteins and derivatives thereof. For example, fluorescent agents can include but are not limited to cyanines, phthalocyanines, porphyrins, indocyanines, rhodamines, phenoxazines, phenylxanthenes, phenothiazines, phenoselenazines, fluoresceins, benzoporphyrins, squaraines, dipyrrolo pyrimidones, tetracenes, quinolines, pyrazines, corrins, croconiums, acridones, phenanthridines, rhodamines, acridines, anthraquinones, chalcogenopyrylium analogues, chlorins, naphthalocyanines, methine dyes, indolenium dyes, azo compounds, azulenes, azaazulenes, triphenyl methane dyes, indoles, benzoindoles, indocarbocyanines, benzoindocarbocyanines, and BODIPY™ derivatives. Fluorescent dyes are discussed, for example, in U.S. Pat. Nos. 4,452,720, 5,227,487, and 5,543,295.

The label can also be a radioisotope, e.g., radionuclides that emit gamma rays, positrons, beta and alpha particles, and X-rays. Suitable radionuclides include but are not limited to $^{225}$Ac, $^{72}$As, $^{211}$At, $^{11}$B, $^{128}$Ba, $^{212}$Bi, $^{75}$Br, $^{77}$Br, $^{14}$C, $^{109}$Cd, $^{62}$Cu, $^{64}$Cu, $^{67}$Cu, $^{18}$F, $^{67}$Ga, $^{68}$Ga, $^{3}$H, $^{166}$Ho, $^{123}$I, $^{124}$I, $^{125}$I, $^{130}$I, $^{131}$I, $^{177}$Lb, $^{13}$N, $^{15}$O, $^{32}$P, $^{33}$P, $^{212}$Pb, $^{103}$Pd, $^{186}$Re $^{188}$Re, $^{47}$Sc, $^{153}$Sm, $^{89}$Sr, $^{99m}$Tc, $^{88}$Y and $^{90}$Y. In some embodiments, radioactive agents can include $^{111}$In-DTPA, $^{99m}$Tc(CO)$_3$-DTPA, $^{99m}$Tc(CO)$_3$-ENPy2, $^{62/64/67}$Cu-TETA, $^{99m}$Tc(CO)$_3$-IDA, and $^{99m}$Tc(CO)$_3$triamines (cyclic or linear). In some embodiments, the agents can include DOTA and its various analogs with $^{111}$In, $^{177}$Lu, $^{153}$Sm, $^{88/90}$Y, $^{62/64/67}$Cu, or $^{67168}$Ga. In some embodiments, a nanoparticle can be labeled by incorporation of lipids attached to chelates, such as DTPA-lipid, as provided in the following references: Phillips et al., *Wiley Interdisciplinary Reviews: Nanomedicine and Nanobiotechnology*, 1(1): 69-83 (2008); Torchilin, V. P. & Weissig, V., Eds. *Liposomes 2nd Ed.*: Oxford Univ. Press (2003); Elbayoumi, T. A. & Torchilin, V. P., *Eur. J. Nucl. Med. Mol. Imaging* 33:1196-1205 (2006); Mougin-Degraef, M. et al., *Int'l J. Pharmaceutics* 344:110-117 (2007).

In some embodiments, the diagnostic agent can be associated with a secondary binding ligand or to an enzyme (an enzyme tag) that will generate a colored product upon contact with a chromogenic substrate. Examples of suitable enzymes include urease, alkaline phosphatase, (horseradish) hydrogen peroxidase and glucose oxidase. Secondary binding ligands include, e.g., biotin and avidin or streptavidin compounds as known in the art.

In some embodiments, the labeled antibody can be further associated to a composition that improves stability in vivo, e.g. PEG or a nanoparticle such as a liposome, as described in more detail below.

B. Methods of Labeling

Techniques for conjugating detectable and therapeutic agents to antibodies are well known (see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery" in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review" in Monoclonal Antibodies '84: Biological And Clinical Applications, Pinchera et al. (eds.), pp. 475-506 (1985); and Thorpe et al., "The Preparation And Cytotoxic Properties Of Antibody-Toxin Conjugates", Immunol. Rev., 62:119-58 (1982)).

Typically, the antibody is attached to detectable moiety in an area that does not interfere with binding to the epitope. Thus in some cases, the detectable moiety is attached to the constant region, or outside the CDRs in the variable region.

One of skill in the art will recognize that the detectable moiety can be located elsewhere on the antibody, and the position of the detectable moiety can be adjusted accordingly. In some embodiments, the ability of the antibody to associate with the epitope is compared before and after attachment to the detectable moiety to ensure that the attachment does not unduly disrupt binding.

In some embodiments, the antibody can be associated with an additional targeting moiety. For example, an antibody fragment, peptide, or aptamer that binds a different site on the target molecule or target cell can be conjugated to the antibody to optimize target binding, e.g., to a cancer cell.

VI. Therapeutic Applications

CLL-1-expressing cells such as AML cells can be targeted using the CLL-1 antibodies described herein. CLL-1 expression is elevated on AML cells and CSCs (e.g., AML CSCs). CLL-1 is not significantly expressed on normal CD34+ hematopoietic stem cells (HSCs), thus CSCs can be distinguished from HSCs using the present CLL-1 antibodies. High affinity CLL-1 antibodies that recognize a CLL-1 epitope common to AML cells, and thus able to universally bind to AML cells, is particularly valuable, as AML has a very high rate of recurrence. As noted above, a therapeutic composition comprising CLL-1 antibody can further include a detectable label to form a theranostic composition, e.g., for detection and localization of CLL-1 expressing cells, and monitoring of therapeutic effect.

As demonstrated herein, the present CLL-1 antibodies can inhibit cancer cell growth (proliferation and/or engraftment) and thus can be considered chemotherapeutic agents alone. The following disclosure provides examples of chemotherapeutic and cytotoxic agents that can be linked to CLL-1 antibody for additional effect on CLL-1-expressing cells.

A chemotherapeutic (anti-cancer) agent can be any agent capable of reducing cancer growth, interfering with cancer cell replication, directly or indirectly killing cancer cells, reducing metastasis, reducing tumor blood supply, etc. Chemotherapeutic agents thus include cytotoxic agents. Cytotoxic agents include but are not limited to saporin, taxanes, *vinca* alkaloids, anthracycline, and platinum-based agents. Classes of chemotherapeutic agents include but are not limited to alkylating agents, antimetabolites, e.g, methotrexate, plant alkaloids, e.g., vincristine, and antibiotics, e.g., doxorubicin as well as miscellaneous drugs that do not fall in to a particular class such as hydroxyurea. Platinum-based drugs, exemplified by cisplatin and oxaliplatin, represent a major class of chemotherapeutics. These drugs bind to DNA and interfere with replication. Taxanes, exemplified by taxol, represent another major class of chemotherapeutics. These compounds act by interfering with cytoskeletal and spindle formation to inhibit cell division, and thereby prevent growth of rapidly dividing cancer cells. Other chemotherapeutic drugs include hormonal therapy.

More than one therapeutic agent can be combined, either in the same composition, or in separate compositions. The therapeutic agent(s) can also be combined with additional therapeutic agents as appropriate for the particular individual. Common therapeutic agents provided to cancer patients include medications to address pain, nausea, anemia, infection, inflammation, and other symptoms commonly experienced by cancer patients.

Antibodies can be attached to a therapeutic agent, detectable agent, or nanocarrier using a variety of known cross-linking agents. Methods for covalent or non-covalent attachment of polypeptides are well known in the art. Such methods may include, but are not limited to, use of chemical cross-linkers, photoactivated cross-linkers and/or bifunctional cross-linking reagents. Exemplary methods for cross-linking molecules are disclosed in U.S. Pat. Nos. 5,603,872 and 5,401,511. Non-limiting examples of cross-linking reagents include glutaraldehyde, bifunctional oxirane, ethylene glycol diglycidyl ether, carbodiimides such as 1-ethyl-3-(3-dimethylaminopropyl) carbodiimide or dicyclohexyl-carbodiimide, bisimidates, dinitrobenzene, N-hydroxysuccinimide ester of suberic acid, disuccinimidyl tartarate, dimethyl-3,3'-dithio-bispropionimidate, azidoglyoxal, N-succinimidyl-3-(2-pyridyldithio)propionate and 4-(bromoadminoethyl)-2-nitrophenylazide.

In some embodiments, the CLL-1 antibody is associated with a nanocarrier. For antibodies conjugated to nanocarriers (e.g., liposomes), a certain number of antibodies will be present on the surface, i.e., at a given surface density. In some embodiments, the nanocarrier will have at least 5 antibodies per nanocarrier, e.g., at least 10, 30, 40, 50, 75, 100 or higher antibodies per nanocarrier. One of skill in the art will understand that surface density represents an average range, as the number of antibodies per nanocarrier will not be absolutely uniform for all members of the population.

Nanocarriers include vesicles such as liposomes and micelles, as well as polymeric nanoparticles, etc. Nanocarriers are useful for delivery of therapeutic and diagnostic agents, but can be particularly useful for shielding cytotoxic agents used to treat cancer. The nanocarrier can comprise lipids (e.g., phospholipids), hydrophilic polymers, hydrophobic polymers, amphipatic compounds, cross-linked polymers, and a polymeric matrix (see, e.g., WO2009/110939). Depending on the application, the nanocarrier can be designed to have a particular size, half-life, shelf life, and leakage rate.

Preparation of nanocarriers, such as an antibody targeted liposome, polymeric nanoparticle, or extended shelf-life liposome, is described, e.g., in U.S. Pat. Nos. 6,465,188, 7,122,202, 7,462,603 and 7,550,441.

In some embodiments, the antibody is linked to a stabilizing moiety such as PEG, or a liposome or other nanocarrier. U.S. Pat. Nos. 4,732,863 and 7,892,554 and Chattopadhyay et al. (2010) *Mol Pharm* 7:2194 describe methods for attaching the selected antibody to PEG, PEG derivatives, and nanoparticles (e.g., liposomes). Liposomes containing phosphatidyl-ethanolamine (PE) can be prepared by established procedures as described herein. The inclusion of PE provides an active functional site on the liposomal surface for attachment.

The antibody conjugate can also be formulated to provide more than one active compound, e.g., additional chemotherapeutic or cytotoxic agents, cytokines, or growth inhibitory agents. The active ingredients may also prepared as sustained-release preparations (e.g., semi-permeable matrices of solid hydrophobic polymers (e.g., polyesters, hydrogels (for example, poly (2-hydroxyethyl-methacrylate), or poly (vinylalcohol)), polylactides. The antibodies and immunocongugates can be entrapped in a nanoparticle prepared, for example, by coacervation techniques or by interfacial polymerization, for example, hydroxymethylcellulose or gelatin microcapsules and poly-(methylmethacylate) microcapsules, respectively, in colloidal drug delivery systems (for example, liposomes, albumin microspheres, microemulsions, nanoparticles and nanocapsules) or in macroemulsions.

The CLL-1 antibodies described herein can kill CLL-1-expressing cells alone, or in combination with a cytotoxic agent. In some embodiments, the method of treatment comprises administering to an individual an effective amount of a therapeutic CLL-1 antibody or CLL-1 antibody conjugate, e.g., a CLL-1 antibody attached to a therapeutic agent. In some embodiments, the individual has been diagnosed with cancer, e.g., AML. In some embodiments, the individual is receiving or has received cancer therapy, e.g., surgery, radiotherapy, or chemotherapy. In some embodiments, the individual has been diagnosed, but the cancer is in remission.

In some embodiments, the method further comprises monitoring the individual for progression of the cancer. In some embodiments, the dose of the CLL-1 antibody or CLL-1 antibody conjugate for each administration is determined based on the therapeutic progress of the individual, e.g., where a higher dose of chemotherapeutic is administered if the individual is not responding sufficiently to therapy.

In some embodiments, the invention can include an antibody or antibody-targeted composition and a physiologically (i.e., pharmaceutically) acceptable carrier. The term "carrier" refers to a typically inert substance used as a diluent or vehicle for a diagnostic or therapeutic agent. The term also encompasses a typically inert substance that imparts cohesive qualities to the composition. Physiologically acceptable carriers can be liquid, e.g., physiological saline, phosphate buffer, normal buffered saline (135-150 mM NaCl), water, buffered water, 0.4% saline, 0.3% glycine, glycoproteins to provide enhanced stability (e.g., albumin, lipoprotein, globulin, etc.), and the like. Since physiologically acceptable carriers are determined in part by the particular composition being administered as well as by the particular method used to administer the composition, there are a wide variety of suitable formulations of pharmaceutical compositions of the present invention (See, e.g., Remington's Pharmaceutical Sciences, 17$^{th}$ ed., 1989).

The compositions of the present invention may be sterilized by conventional, well-known sterilization techniques or may be produced under sterile conditions. Aqueous solutions can be packaged for use or filtered under aseptic conditions and lyophilized, the lyophilized preparation being combined with a sterile aqueous solution prior to administration. The compositions can contain pharmaceutically acceptable auxiliary substances as required to approximate physiological conditions, such as pH adjusting and buffering agents, tonicity adjusting agents, wetting agents, and the like, e.g., sodium acetate, sodium lactate, sodium chloride, potassium chloride, calcium chloride, sorbitan monolaurate, and triethanolamine oleate. Sugars can also be included for stabilizing the compositions, such as a stabilizer for lyophilized antibody compositions.

Dosage forms can be prepared for mucosal (e.g., nasal, sublingual, vaginal, buccal, or rectal), parenteral (e.g., subcutaneous, intravenous, intramuscular, or intraarterial injection, either bolus or infusion), oral, or transdermal administration to a patient. Examples of dosage forms include, but are not limited to: dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

Injectable (e.g., intravenous) compositions can comprise a solution of the antibody or antibody-targeted composition suspended in an acceptable carrier, such as an aqueous carrier. Any of a variety of aqueous carriers can be used, e.g., water, buffered water, 0.4% saline, 0.9% isotonic saline, 0.3% glycine, 5% dextrose, and the like, and may include glycoproteins for enhanced stability, such as albumin, lipoprotein, globulin, etc. Often, normal buffered saline (135-150 mM NaCl) will be used. The compositions can contain pharmaceutically acceptable auxiliary substances to approximate physiological conditions, such as pH adjusting and buffering agents, tonicity adjusting agents, wetting agents, e.g., sodium acetate, sodium lactate, sodium chloride, potassium chloride, calcium chloride, sorbitan monolaurate, triethanolamine oleate, etc. In some embodiments, the antibody-targeted composition can be formulated in a kit for intravenous administration.

Formulations suitable for parenteral administration, such as, for example, by intraarticular (in the joints), intravenous, intramuscular, intratumoral, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

The pharmaceutical preparation can be packaged or prepared in unit dosage form. In such form, the preparation is subdivided into unit doses containing appropriate quantities of the active component, e.g., according to the dose of the therapeutic agent or concentration of antibody. The unit dosage form can be a packaged preparation, the package containing discrete quantities of preparation, in unit-dose or multi-dose sealed containers, such as ampoules and vials. The composition can, if desired, also contain other compatible therapeutic agents.

The antibody (or antibody-targeted composition) can be administered by injection or infusion through any suitable route including but not limited to intravenous, subcutaneous, intramuscular or intraperitoneal routes. An example of administration of a pharmaceutical composition includes storing the antibody at 10 mg/ml in sterile isotonic aqueous saline solution for injection at 4° C., and diluting it in either 100 ml or 200 ml 0.9% sodium chloride for injection prior to administration to the patient. The antibody is administered by intravenous infusion over the course of 1 hour at a dose of between 0.2 and 10 mg/kg. In other embodiments, the antibody is administered by intravenous infusion over a period of between 15 minutes and 2 hours. In still other embodiments, the administration procedure is via sub-cutaneous bolus injection.

The dose of antibody is chosen in order to provide effective therapy for the patient and is in the range of less than 0.1 mg/kg body weight to about 25 mg/kg body weight or in the range 1 mg-2 g per patient. In some cases, the dose is in the range 1-100 mg/kg, or approximately 50 mg-8000 mg/patient. The dose may be repeated at an appropriate frequency which may be in the range once per day to once every three months, depending on the pharmacokinetics of the antibody (e.g., half-life of the antibody in the circulation) and the pharmacodynamic response (e.g., the duration of the therapeutic effect of the antibody). In some embodiments, the in vivo half-life of between about 7 and about 25 days and antibody dosing is repeated between once per week and once every 3 months.

Administration can be periodic. Depending on the route of administration, the dose can be administered, e.g., once every 1, 3, 5, 7, 10, 14, 21, or 28 days or longer (e.g., once every 2, 3, 4, or 6 months). In some cases, administration is more frequent, e.g., 2 or 3 times per day. The patient can be monitored to adjust the dosage and frequency of administration depending on therapeutic progress and any adverse side effects, as will be recognized by one of skill in the art.

Thus in some embodiments, additional administration is dependent on patient progress, e.g., the patient is monitored between administrations. For example, after the first administration or round of administrations, the patient can be monitored for rate of tumor growth, recurrence (e.g., in the case of a post-surgical patient), or general disease-related symptoms such as weakness, pain, nausea, etc.

For the treatment of cancer, an antibody or antibody-targeted composition (e.g., including a therapeutic and/or diagnostic agent) can be administered at the initial dosage of about 0.001 mg/kg to about 1000 mg/kg daily and adjusted over time. A daily dose range of about 0.01 mg/kg to about 500 mg/kg, or about 0.1 mg/kg to about 200 mg/kg, or about 1 mg/kg to about 100 mg/kg, about 5 to about 10 mg/kg, or about 10 mg/kg to about 50 mg/kg, can be used. The in vivo xenograft results described herein indicate that a dose between 5-20 mg antibody/kg body weight is effective for dramatic reduction of tumor growth.

The dosage is varied depending upon the requirements of the patient, the severity of the condition being treated, and the targeted composition being employed. For example, dosages can be empirically determined considering the type and stage of cancer diagnosed in a particular patient. The dose administered to a patient, in the context of the present invention, should be sufficient to affect a beneficial therapeutic response in the patient over time. The size of the dose will also be determined by the existence, nature, and extent of any adverse side-effects that accompany the administration of a particular targeted composition in a particular patient, as will be recognized by the skilled practitioner.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entireties for all purposes.

VII. EXAMPLES

A. Example 1: Characterization of CLL-1 Antibody Sequences and Structure

Human CLL-1 was used to generate antibodies in mice. Antibodies specific for CLL-1 were selected and cloned into hybridomas for stable production of monoclonal antibodies. A number of antibodies specific for CLL-1 were cloned and characterized for sequence and antibody structure. These data are shown in Tables 1-3 below. The heavy and light chain variable region sequences are shown in the sequence listing.

TABLE 1

Antibody structures

| Clone | Isotype | VH | DH | JH | VK | JK |
|---|---|---|---|---|---|---|
| M26 | IgG2b | VhJ558.b14 | PseudoD3 | JH4 | IGKV9-124*01 | JK2 |
| M31 | IgG2a | VhJ558.b14 | DSP2.2 | JH2 | IGKV3-10*01 | JK1 |
| G4 | IgG1 | VHJ558 | DSP2.2 | JH4 | IGKV10-96*01 | JK1 |
| M22 | IgG2a | IGHV1-61*01 | DSP2.5 | JH4 | IGKV8-19*01 | JK5 |
| M29 | IgG1 | VhJ558.b14 | DSP2.2 | JH2 | IGKV19-93*01 | JK1 |
| M2 | IgG1 | IGHV1-36*01 | DSP2.9 | JH4 | IGKV9-124*01 | JK2 |
| M5 | IgG2a | 14-1-39 | DQ52a.1 | JH2 | IGKV8-30*01 | JK1 |
| G12 | IgG1 | | DFL16.3 | JH1 | IGKV3-10*01 | JK2 |

TABLE 2

J sequences

| Clone | J HC | J LC |
|---|---|---|
| M26 | CTRDDGYYGYAMDYW | CLQYAIYPYTF |
| M31 | CARPIYFDNDYFDYW | CQQNNYDPWTF |
| G4 | CARTDDYDDYTMDYW | CQQGKTLLWTF |
| M22 | CAIYYGNPSYYAMDYW | CQNDYSYPFTF |
| M29 | CARYYDYYFDYW | CLQYDYLWTF |
| M2 | CTRDDGYYDYAMDYW | CLQYASYPYTF |
| M5 | CTLTGRFDYW | CQQYYSYRTF |
| G12 | CARVYNWHFDVW | CQQNNEDPYTF |

J HCs: SEQ ID NOs: 35-42 (top to bottom)
J LCs: SEQ ID Nos: 43-50

TABLE 3

CDR sequences

| Clone | CDR H1 | CDR H2 | CDR H3 | CDR L1 | CDR L2 | CDR L3 |
|---|---|---|---|---|---|---|
| M26 | GYTFTSYF | INPYNDGS | TRDDGYYGYAMDY | QELSGY | AAS | LQYAIYPYT |
| M31 | GYTFTSYV | INPYNDGT | ARPIYFDNDYFDY | ESVDSYGNSF | LAS | QQNNYDPWT |
| G4 | GYSFTGYT | INPYNDGT | ARTDDYDDYTMDY | HDISNY | YTS | QQGKTLLWT |
| M22 | GYTFTRYW | IDPSDTET | AIYYGNPSYYAMDY | QNLLNSGNQKKY | WAS | QNDYSYPFT |

TABLE 3-continued

| Clone | CDR H1 | CDR H2 | CDR H3 | CDR L1 | CDR L2 | CDR L3 |
|---|---|---|---|---|---|---|
| M29 | GYIFTSYV | INPYNDGT | ARYYDYDYYFDY | QDINKY | YTS | LQYDYLWT |
| M2 | GYTFTSYF | INPYNDGT | TRDDGYYDYAMDY | QEISVY | AAS | LQYASYPYT |
| M5 | GFNIKDDY | IDPEKGDT | TLTGRFDY | QSLLYSSNQKNN | WAS | QQYYSYRT |
| G12 | GYTFPSSN | IYPGNGDT | ARVYNWHFDV | ESVDGYGDIF | FAS | QQNNEDPYT |

CDR H1s: SEQ ID NOs: 51-58
CDR H2s: SEQ ID NOs: 59-66
CDR H3s: SEQ ID NOs: 67-74
CDR L1s: SEQ ID NOs: 75-82
CDR L2s: SEQ ID NOs: 83-90
CDR L3s: SEQ ID NOs: 91-98

B. Example 2: Epitope Binding Studies

For certain clones, epitope mapping was carried out, and compared to the location of binding to CLL-1 for known antibodies. These antibodies include Nuvelo/X1057 (US20100285037), Crucell/X357 (U.S. Pat. No. 7,741,443), and Goat anti CLL-1. A summary is shown in Table 4 below. CLL-1 or the C lectin domain of CLL-1 was expressed in 293T cells. Non-transfected 293T cells, or 293T cells transfected with mouse CLL-1 were used as controls.

TABLE 4

Epitope binding

| Clone | 293T | 293T mCLL-1 | 293T hCLL-1 | 293T C lectin domain |
|---|---|---|---|---|
| M13 | − | − | + | + |
| M26 | − | − | + | − |
| M31 | − | − | + | − |
| X357 | − | − | + | + |
| X1057 | − | − | + | + |
| Goat anti-CLL-1 | − | − | + | + |

The data show that clones M26 and M31 bind to human CLL-1, but that the C lectin domain is not sufficient for significant binding.

The M26 and M31 antibodies were also tested for binding to Cynomolgus monkey CLL-1. These animals can be used for clinical studies, thus it is useful to have target-specific antibodies that bind the Cynomolgus species homolog of a human antibody target. M26 was found to bind Cynomolgus CLL-1 with high affinity.

Additional Cynomolgus CLL-1 binding studies were carried out using ELISA. The results are shown in Table 5 below.

TABLE 5

Cynomolgus CLL-1 binding

| Clone | Relative binding |
|---|---|
| M26 | ++++ |
| M31 | ++ |
| G4 | ++++ |
| M2 | +++ |
| M5 | +++ |
| M13 | − |

TABLE 5-continued

Cynomolgus CLL-1 binding

| Clone | Relative binding |
|---|---|
| M22 | − |
| M29 | + |
| M41 | + |

C. Example 3: Affinity Testing

Affinity testing was carried out for the CLL-1 antibody clones. Briefly, biotinylated CLL-1 (25 ug/ml) is loaded onto strepavidin sensor tips for 2 hours at 22 C. Ab-Ag dissociation curves were generated at three different concentrations for each antibody (10, 30, and 90 ug/ml) using a global 1:1 curve fitting. The results are shown in Table 6 below.

TABLE 6

Affinity Kd (pM)

| Clone | Affinity for hCLL-1 |
|---|---|
| M26 | 214 |
| M31 | 611 |
| G4 | 53 |
| M2 | 205 |
| M5 | 553 |
| M13 | 854 |
| M22 | 388 |
| M29 | 1480 |
| M41 | 387 |
| D11 | 436 |
| E3 | 447 |
| G2 | 4640 |
| G6 | 1492 |
| G8 | 980 |
| G10 | 194 |
| G12 | 70 |
| G14 | 187 |
| G16 | 2357 |
| G23 | 543 |
| G26 | 134 |
| G30 | 241 |

D. Example 4: Binding to AML Cell Lines and AML Patient Samples

The CLL-1 antibodies were tested for binding to recombinant 293 cells expressing human CLL-1, and two AML, cell lines, HL60 and OCI AML-5. The percentage of live cells with antibody binding, as detected by FACS, is shown in Table 7 below.

TABLE 7

Antibody binding to cell lines (%)

| Clone | 293 CLL-1 | HL60 | OCI AML-5 |
|---|---|---|---|
| M26 | 99.9 | 91 | 92.7 |
| M31 | 76 | 91 | 89.7 |
| G4 |  | 83.2 | 83.2 |
| M2 | 99.9 | 90.3 | 96.3 |
| M5 | 1.1 | 1.7 | 2.3 |
| M13 | 90 | 13.6 | 35.3 |
| M22 | 97 | 37.2 | 57.6 |
| M29 | 99.9 | 84.6 | 87.6 |
| M41 | 99 | 95.2 | 87.1 |
| B10 | 99.9 | 92 | 16 |
| D11 | 82 |  |  |
| E3 | 99.9 | 86 | 8 |
| G2 | 99.9 | 10 | 88.8 |
| G6 | 99.9 | 83.7 |  |
| G8 | 98 | 65.5 |  |
| G10 | 99.9 | 88.5 |  |
| G12 | 99.9 | 88.3 |  |
| G14 | 99.9 | 86.2 |  |
| G16 |  | 56.4 |  |
| G23 |  | 81.4 |  |
| G26 | 99.9 | 92.3 |  |
| G30 | 99.9 | 89.2 |  |

Previously characterized CLL-1 antibodies typically bind primary AML cells with high variability, which is problematic for broad use with patient samples. Some do not detectably bind samples from certain patients. The presently disclosed antibodies were tested for binding to primary cells from AML patient samples by FACS. Two groups of samples were studied: the first consisting of 6 patients, the other consisting of a larger cohort of 37. Each antibody clone was not tested for binding to every sample in the groups. Results of binding are shown in Table 8. M26 and M31 were further found to bind 90% or more cells from AML patient primary cell samples by FACS.

TABLE 8

Binding of primary AML samples
(Positive/Total number of patient samples tested)

| Clone | Group 1 | Group 2 |
|---|---|---|
| M26 | 6/6 | 32/37 |
| M31 | 2/3 | 5/12 |
| G4 | 2/2 | 4/6 |
| M2 | 2/2 |  |
| M5 | 1/6 | 0/20 |
| M13 | 2/3 | 0/20 |
| M22 | 3/5 | 1/35 |
| M29 |  | 4/26 |
| M41 | 6/6 |  |
| B10 | 5/6 |  |
| D11 |  |  |
| E3 | 4/6 | 2/6 |
| G2 | 1/2 |  |
| G6 | 1/2 |  |
| G8 | 2/2 |  |
| G10 | 1/1 | 2/5 |
| G12 | 2/2 |  |
| G14 | 2/2 |  |
| G16 | 2/2 |  |
| G23 | 2/2 |  |
| G26 | 2/2 |  |
| G30 | 1/1 |  |

E. Example 5: Antibody-Drug Conjugate (ADC) Assays

Antibody-Drug Conjugate (ADC) assays were carried out on AML cell lines HL60 and OCI AML-5, as well as recombinant 293 cells expressing CLL-1. Briefly, cells were incubated with various concentrations of saporin-conjugated antibodies for 48-72 hours at 37 C. Cell viability was determined by DHL colorimetric assay to determine EC50 values.

Results are shown below in Table 9.

TABLE 9

ADC assays

| Clone | ADC EC50 (pM) |
|---|---|
| M26 | 90.23 |
| M31 | 34.28 |
| G4 | 44.35 |
| M2 | 20.95 |
| M5 | 149.5 |
| M29 | 91.39 |
| B10 | 54.72 |
| D11 | 15.85 |
| E3 | 13.37 |
| G2 | 28.23 |
| G6 | 34.07 |
| G10 | 27.94 |
| G12 | 19.43 |
| G26 | 34.86 |
| G30 | 29.33 |

F. Example 6: Complement Dependent Cytotoxicity (CDC) Assays

Complement dependent cytotoxicity assays were carried out on primary cells from AML patients. Primary AML cells were incubated with CLL1 antibodies at various concentrations for 2 hours at 37 C in the presence of complement. Cell viability was determined by colorimetric Cellglow assay (Promega).

Figure 1B:
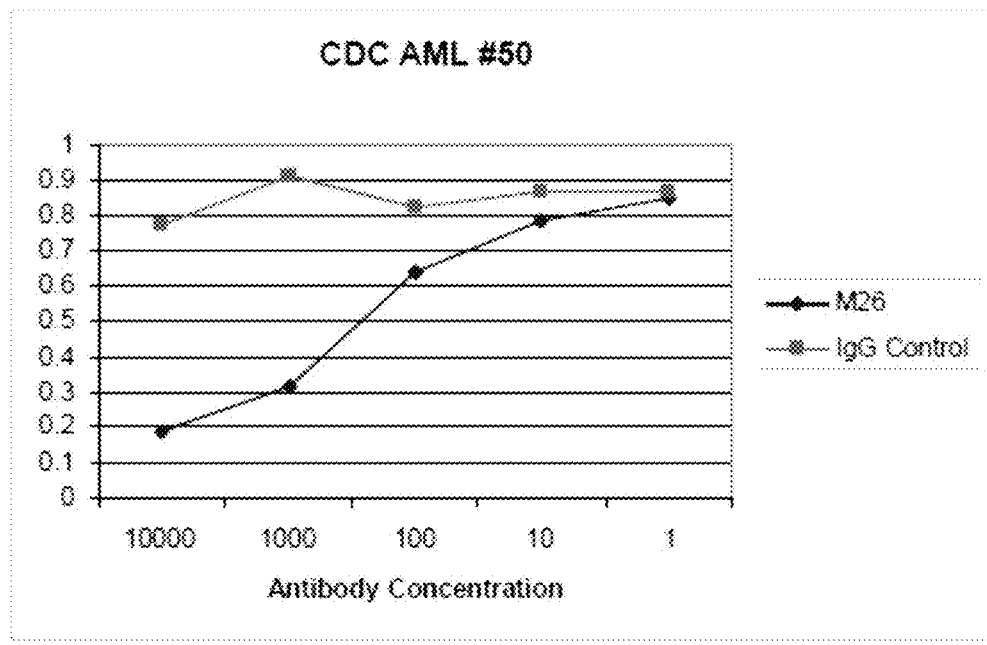
Figure 1C:
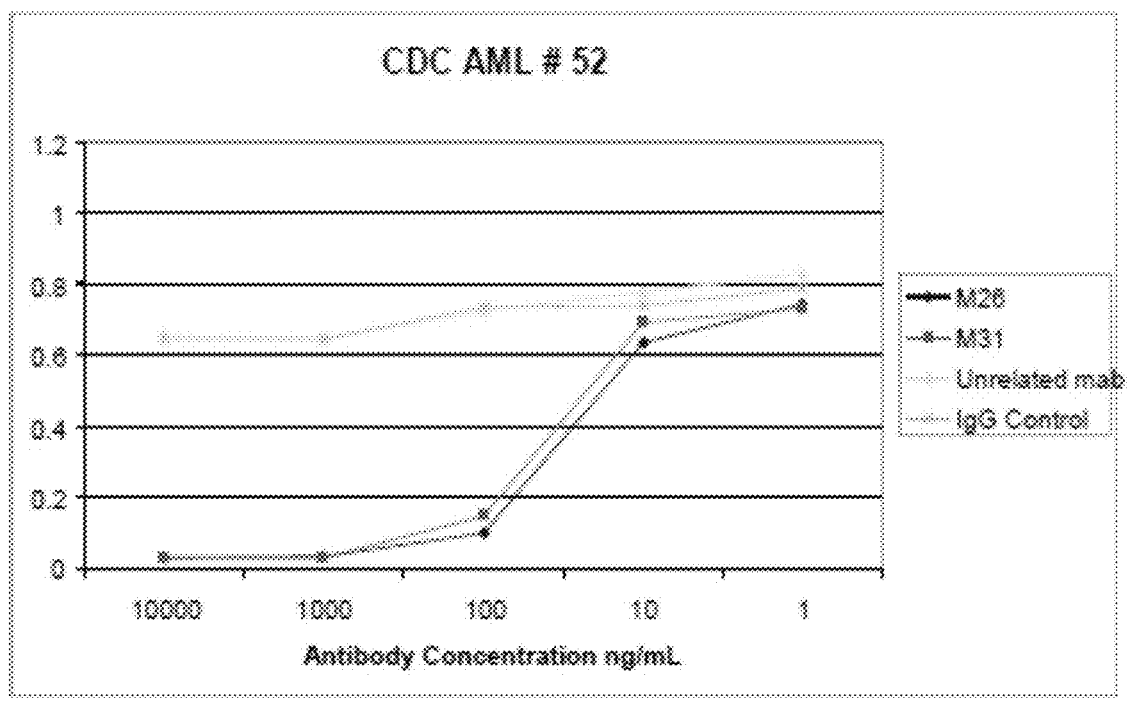

FIGS. 1A-1C shows results from 3 AML patient samples. CLL-1 antibody clone M26 has an EC50 of about 10-100 ng/mL with these cell samples. FIG. 1C, representing AML sample #52, also shows the effect of clone M31 compared to E12 (unrelated mAb) and IgG control.

Results from another round of CDC assays, using 10 ug/mL antibody, are shown in Table 10.

TABLE 10

CDC assays

| Clone | CDC (% killing) |
|---|---|
| M26 | 17.18 |
| M31 | 12.14 |
| M5 | 17.87 |
| M22 | 14.49 |
| D11 | 18.52 |

The data show that the CLL-1 antibody clones have significant CDC activity on primary AML patient samples. The CLL-1 antibody clones are effective across at least a 5-fold difference in CLL-1 antigen density in patient samples.

G. Example 7: In Vivo Inhibition of AML Tumor Growth

Two sets of in vivo efficacy studies were carried out. The first was a subcutaneous (SC) tumor engraftment and growth model utilizing the CLL-1 positive HL60 AML human cell line in mice. The second was an orthotopic (bone marrow, blood, spleen and lymph node) tumor engraftment and outgrowth model utilizing the CLL-1 positive OCI AML-5 human AML cell line.

Figure 2:
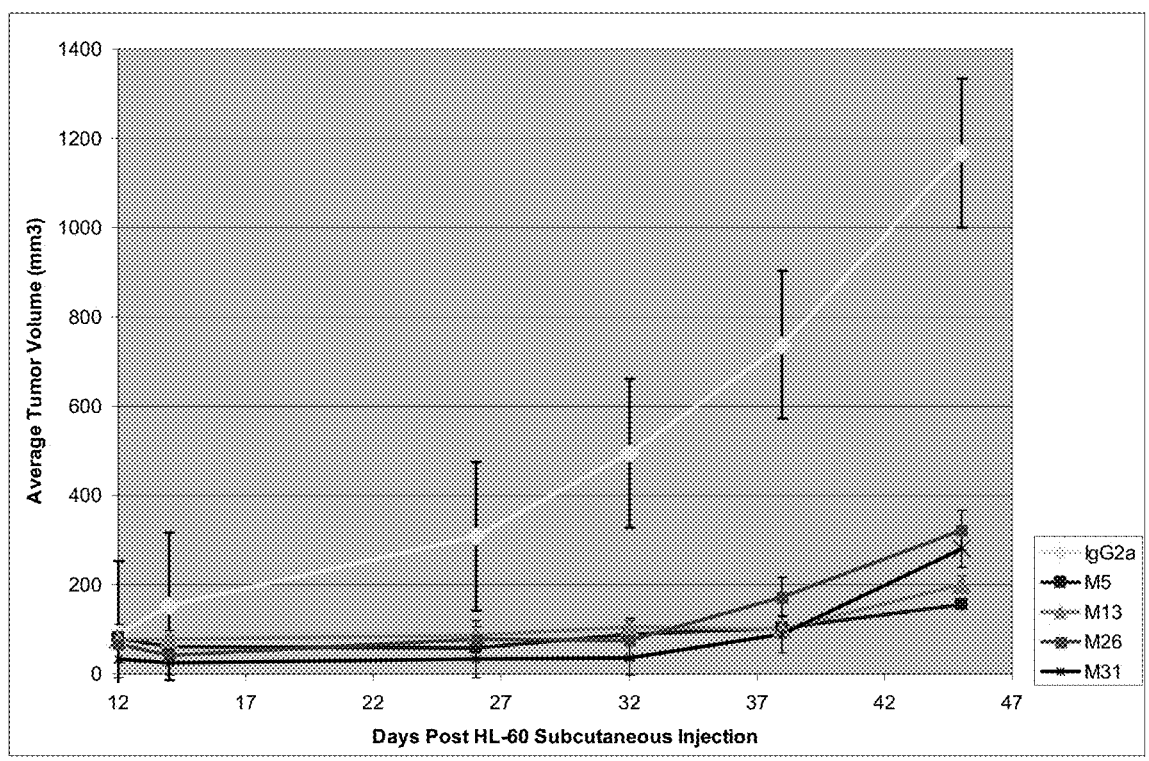
FIG. 2 shows the antitumor effect of CLL-1 antibody clones in a mouse xenograft model. HL60 AML cells were injected subcutaneously into mice. Mice were divided into 5 groups, with n=6 mice per group: (1) IgG2a control; (2) M5; (3) M13; (4) M26; and (5) M31. Mice received 200 ug antibody once per week for 7 weeks. P<0.05 vs control for all treatment groups.

The SC HL60 study was carried out as follows. One of 4 CLL-1 antibody clones (M5, M13, M26, and M31), or an IgG control, were administered i.p. at a dose of 200 ug/animal approximately 24 hours prior to SC inoculation of $5 \times 10^6$ or $10^7$ HL60 cells. Animals received additional antibody doses once per week for the next 6 weeks. The study terminated 45 days after the HL60 cell administration. FIG. 2 shows efficacy curves for various CLL1 antibody clones (M5, M13, M26, and M31) compared to control.

Figure 3:
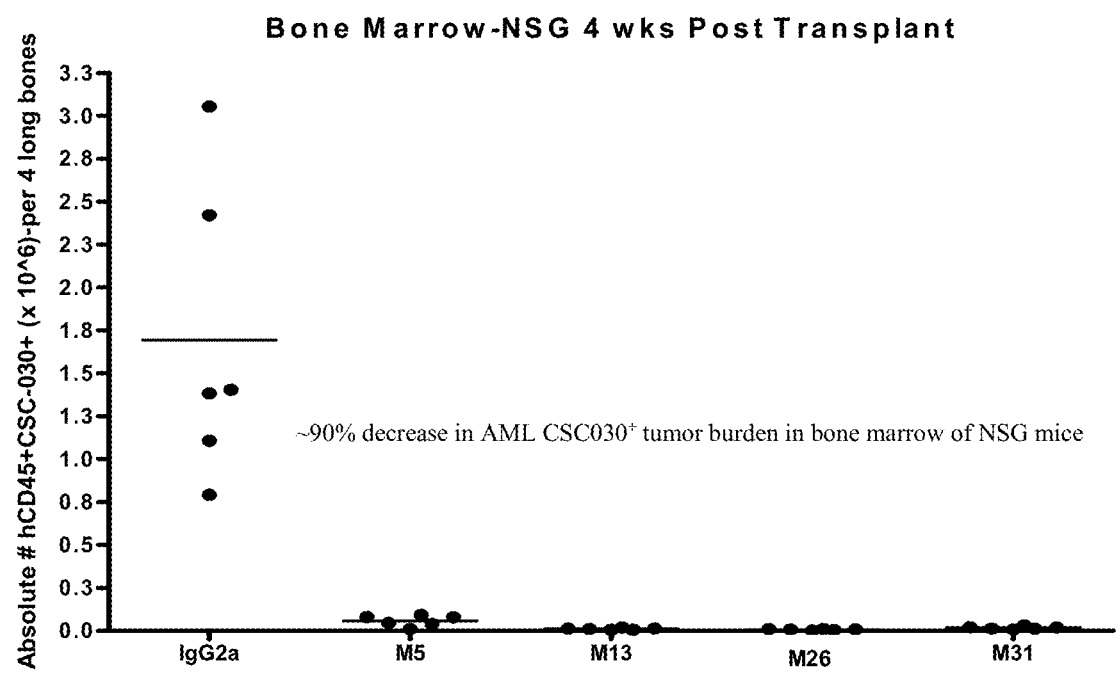
FIG. 3 shows the antitumor effect of CLL-1 antibody clones in a mouse orthotopic xenograft model. AML cells were injected intravenously into immunocompromised NSG (NOD/SCID/IL2 receptor Gamma chain knockout) mice. Mice were divided into 5 groups, with n=6 mice per group: (1) IgG2a control; (2) M5; (3) M13; (4) M26; and (5) M31. Mice received 200 ug antibody twice per week for 2 weeks, and were sacrificed 4 weeks post-transplant. Tumor burden (CD45+ CLL-1+ cells) in bone marrow was determined by FACS.

The OCI AML-5 cell orthotopic studies were carried out as follows. Immunodeficient NSG mice were split into 5 groups of 6 animals/group. One of 4 CLL-1 antibody clones (M5, M13, M26, and M31), or an IgG control, were administered i.p. at a dose of 200 ug/animal approximately 24 hours prior to intravenous inoculation of $5 \times 10^6$ or $10^7$ OCI AML-5 cells. Animals then received additional antibody doses twice per week for the next 2 weeks. The study terminated 4 weeks after administration of the OCI AML-5 cells. FIG. 3 shows that the CLL-1 antibody clones dramatically reduced the number of OCI AML-5 cells (labeled hCD45+ CSC-030+ and AML CSC030+) in vivo.

Figure 4A:
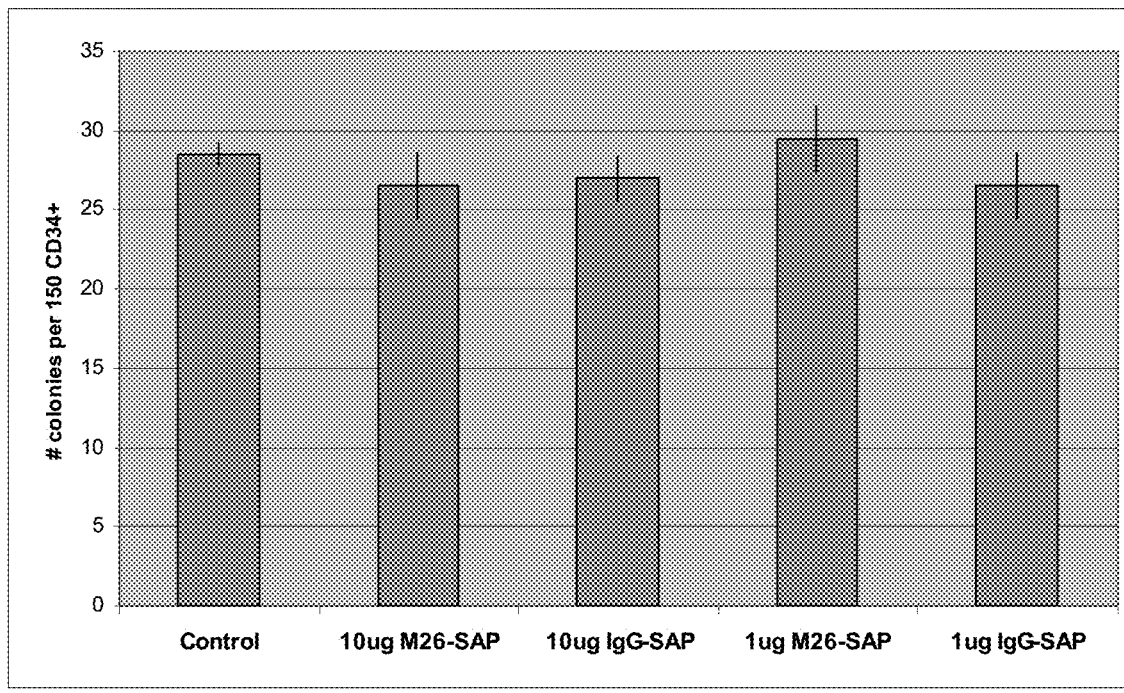
FIGS. 4A-4B show that CLL-1 Antibody Drug Conjugates (ADC) inhibit colony formation by AML stem cells but not normal hematopoietic stem cells (CD34+ HSCs).
Figure 4B:
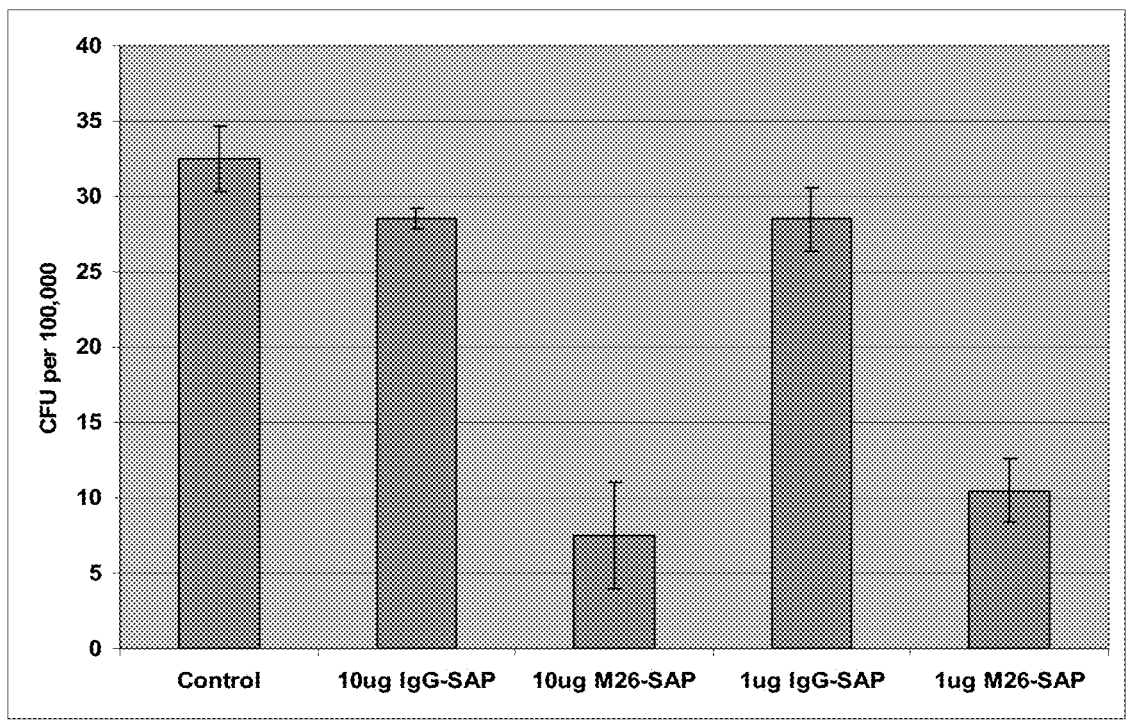

H. Example 8: CLL-1 Antibodies are Specific for AML Stem Cells in ADC Assays The M26 CLL-1 antibody was tested for specific killing in an ADC assay, conjugated to saporin. Primary patient AML cells or normal CD34 positive hematopoietic stem cells isolated from the bone marrow of human subjects, were seeded into a soft agar colony formation assay (100,000 cells/plate). The cells were then incubated in the presence of CLL-1-saporin toxin-conjugated monoclonal antibody clone M26 for 14 days. As shown in FIGS. 4A-4B, the CLL-1 antibody—saporin conjugate caused selective, specific inhibition of AML stem cell clonogenic growth, while normal HSCs were not affectted. The negative controls were untreated or treated with an unrelated IgG-saporin conjugate. The results demonstrate that CLL-1 antibody conjugated to cytotoxin reduces AML cell colony formation by about 80%, without inhibiting HSC colony formation. The results indicate that the presently disclosed CLL-1 antibodies can be used safely therapeutically to specifically target CLL-1 expressed on AML cells.

Figure 5:
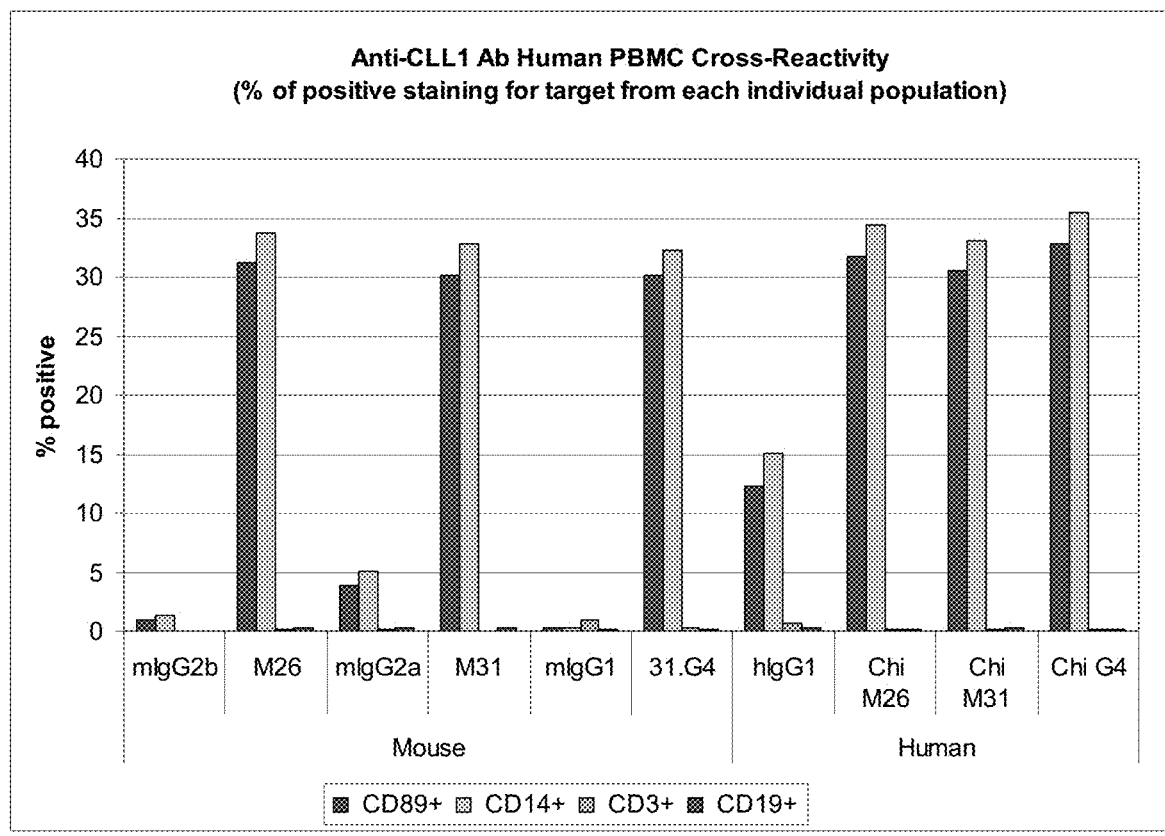
FIG. 5 shows that CLL-1 antibody clones M26, M31, and G4 (also labeled 31.G4) bind to human PBMCs in both mouse and chimeric human (Chi) forms. Negative controls include the IgG corresponding to each CLL-1 antibody, but specific for an unrelated antigen. Mononuclear cells were separated from PBMC samples, and FACS was used to characterize the cells according to expression of CD89 (granulocytes), CD14 (monocytes and granulocytes), CD3 (lymphocytes), and CD19 (B cells). The percentage of CLL-1 positive staining for each population is shown in that order from left to right for each CLL-1 antibody.

I. Example 9: Human Chimeric CLL-1 Antibodies Bind Human Peripheral Blood Mononuclear Cells (PBMCs) Similar to Mouse CLL-1 Antibody Clones The variable regions (Fab) of CLL-1 antibody clones M26, M31, and G4 were used to make chimeric antibodies with a constant region (Fc) from a human IgG1. These human chimeric antibodies are referred to as ChiM26, ChiM31, and ChiG4 (or Chi31G4). To test the specificity of the human chimeric antibodies compared to the parent mouse antibodies, the antibodies were used to stain different populations of human PBMCs. PBMCs were obtained from two human donors, separated by Ficoll gradient, and pooled. About $2 \times 10^5$ mononuclear cells were blocked with 3% human serum and then stained with antibodies specific for lineage markers CD89 (granulocyte), CD14 (monocyte and granulocyte), CD3 (lymphoid), and CD19 (B cell). FIG. 5 shows the FACS results for live-gated cells. The human chimeric CLL-1 antibodies stain the same myeloid lineage populations as the mouse CLL-1 antibodies.

Figure 6:
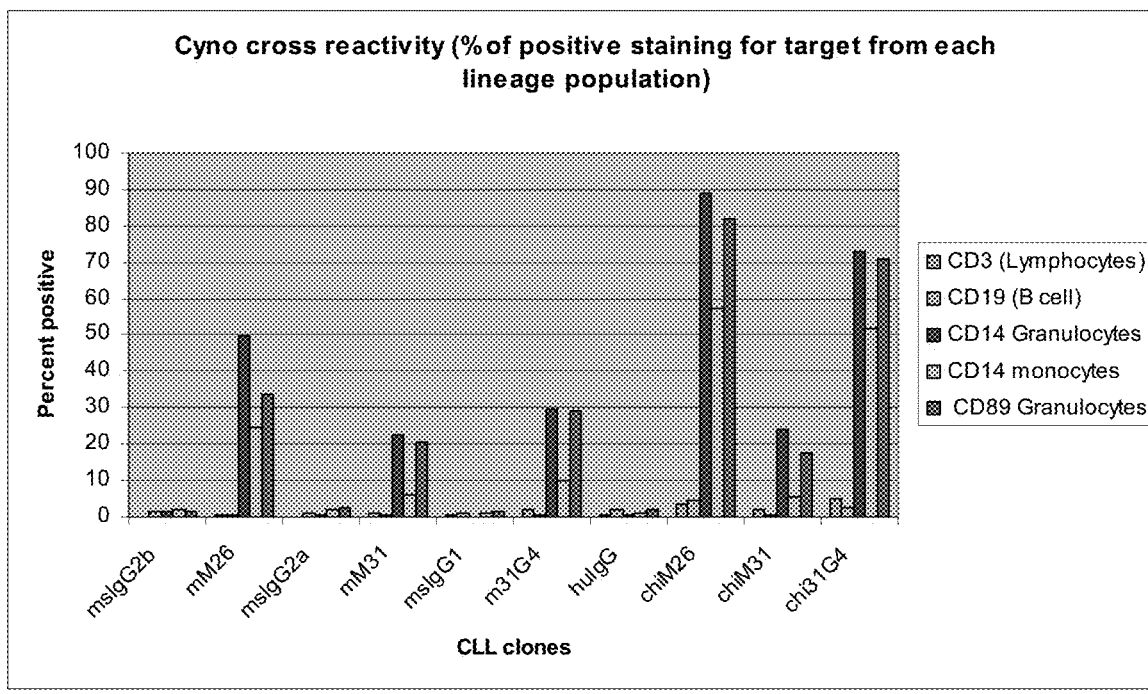
FIG. 6 shows that CLL-1 antibody clones M26, M31, and G4 (labeled 31G4) bind to cynomolgus PBMCs in both orginal mouse and chimeric human (Chi) forms. Negative controls include the IgG corresponding to each CLL-1 antibody, but specific for an unrelated antigen. Mononuclear cells were separated from PBMC samples, and FACS was used to characterize the cells according to expression of CD3 (lymphocytes), CD19 (B cells), CD14 (granulocytes), CD14 (monocytes), and CD89 (granulocytes). The percentage of CLL-1 positive staining for each population is shown in that order from left to right for each CLL-1 antibody.

J. Example 10: Human Chimeric CLL-1 Antibodies Bind Cynomolgus PBMCs Similar to Mouse CLL-1 Antibody Clones To test the specificity of the human chimeric antibodies compared to the parent mouse antibodies, the antibodies were used to stain different populations of cynomolgus PBMCs. PBMCs were obtained from three donors, separated by Ficoll gradient, and pooled. About $2 \times 10^5$ mononuclear cells were blocked with 3% human serum and then stained with antibodies specific for lineage markers CD3 (lymphoid), CD19 (B cell), CD14 (granulocyte), CD14 (monocyte), and CD89 (granulocyte). FIG. 6 shows the FACS results for live-gated cells. The human chimeric CLL-1 antibodies stain the same myeloid lineage populations as the mouse CLL-1 antibodies.

Figure 7A:
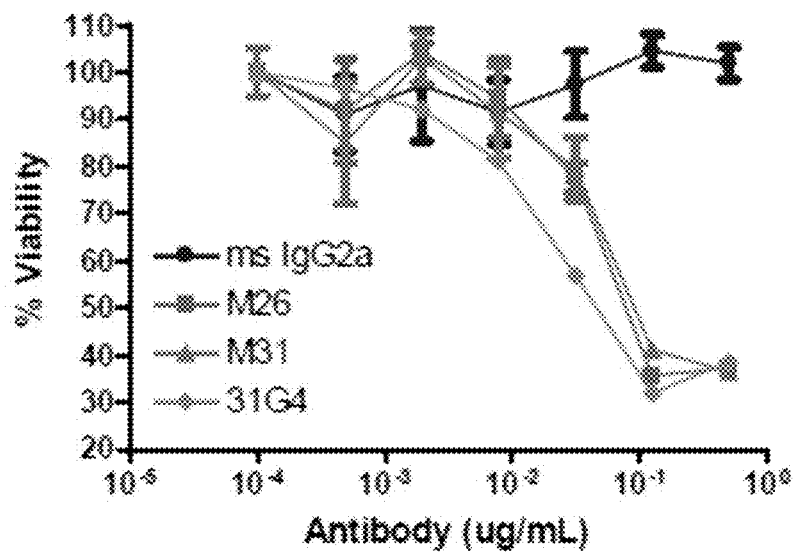
FIGS. 7A-7B show that both mouse and chimeric human CLL-1 have Antibody Drug Conjugate (ADC) activity on CLL-1 transfected 293 cells in vitro.
Figure 7B:
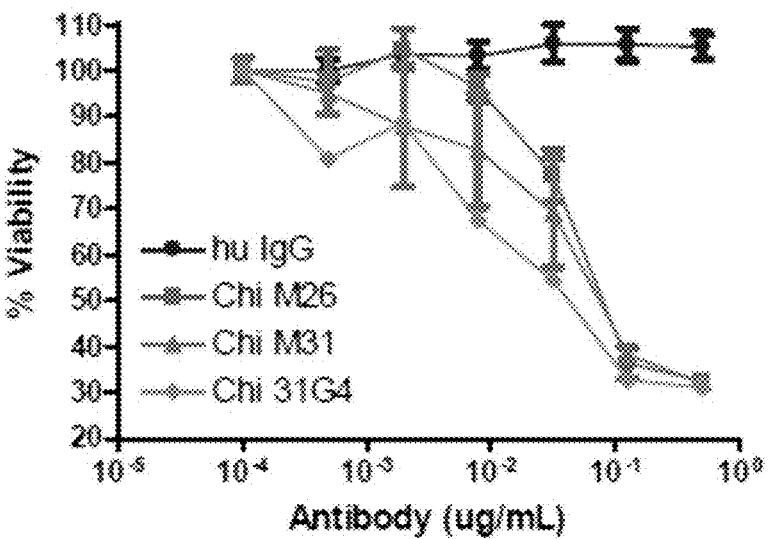

K. Example 11: Human Chimeric CLL-1 Antibodies have In Vitro Antibody-Drug Conjugate Activity The ability of the human chimeric CLL-1 antibodies to internalize and mediate ADC was tested on CLL-1 expressing 293 cells in vitro. Cells were contacted with the indicated antibodies at various concentrations. Matching IgG isotype antibodies were used for negative controls. Then saporin conjugated secondary antibody (Mousezap® or Humzap®) was added at a 2:1 ratio, and the cells were incubated for 72 hours. Cell Titre-Glo® was added to each culture well and mixed for 5-10 minutes and detected on a luminescent plate reader. Cell viability was determined by luminescent signal. FIGS. 7A-7B show that the human chimeric CLL-1 antibodies (7B) have almost identical ADC activity as the mouse CLL-1 antibody clones (7A).

Figure 8:
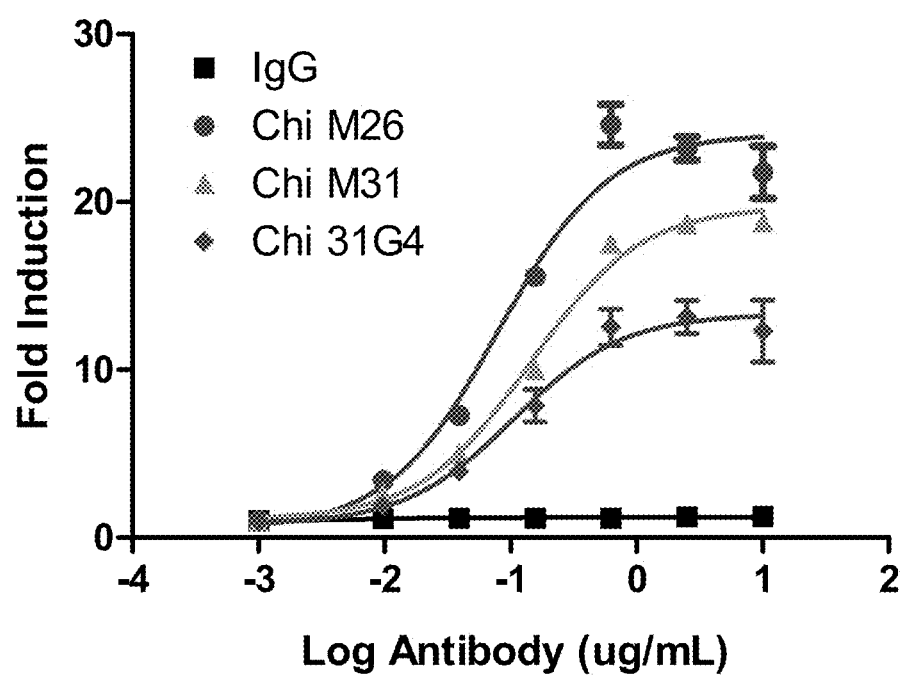
FIG. 8 shows that chimeric human CLL-1 antibody clones M26, M31, and G4 (31G4) mediate antibody-dependent cell-mediated cytotoxicity (ADCC) on CLL-1 transfected 293 cells. The $EC_{50}$ (ng/ml) for ChiM26, ChiM31, and Chi31G4 is 79, 143, and 105, respectively.

L. Example 12: Human Chimeric CLL-1 Antibodies Mediate Antibody Dependent Cell-Mediated Cytotoxicity (ADCC) Activity The ability of the human chimeric CLL-1 antibodies ChiM26, ChiM31, and ChiG4 (Chi31G4) to mediate ADCC was determined on CLL-1 expressing 293 cells. Target cells were added to 96 round bottom wells and incubated with the indicated antibodies at various concentrations and effector cells (Promega®) for 6 hours at 37 C. Viable cells were detected using Promega ADCC Reporter Assay®. Results are shown in FIG. 8. The human IgG isotype control had no detectable activity, while $EC_{50}$ in ng/ml for ChiM26, ChiM31, and Chi31G4 was determined to be 79, 143, and 105, respectively.

M. Example 13: In Vivo Inhibition of AML Tumor Growth

Two sets of in vivo xenograft studies were carried out with mouse and human chimeric CLL-1 antibodies. Both studies utilized NOD/SCID mice irradiated 1 day before tail vein injection with human AML cells on Day 0. Both studies included 8 antibody injections over the course of about 3 weeks, followed by detection of tumor growth in bone marrow cells.

Figure 9A:
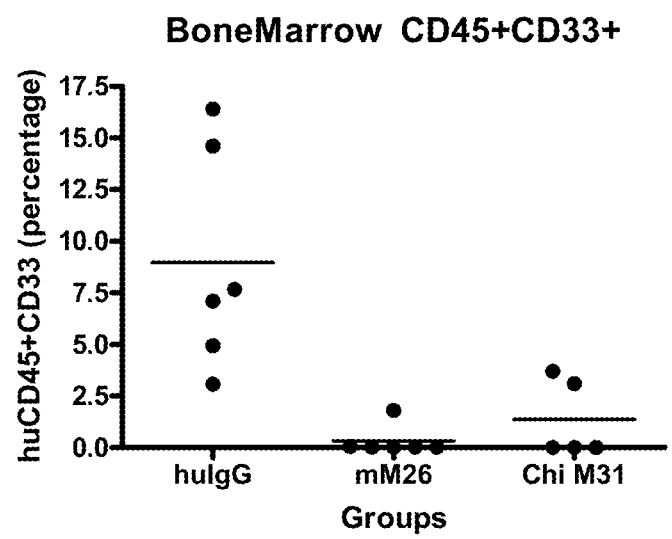
FIGS. 9A-9B show the antitumor effect of CLL-1 antibody clones in a mouse xenograft model. NOD/SCID mice were irradiated on Day −1, and on Day 0, HL60 cells were injected into the tail veins ($3\times10^6$ cells per mouse). Mice were divided into 3 groups, with n=6 mice per group: (1) huIgG control; (2) M26; (3) ChiM31. Mice received 8 antibody injections (200 ug) over the course of 22 days, and were sacrificed on day 26. Tumor burden in bone marrow was determined by FACS.
Figure 9B:
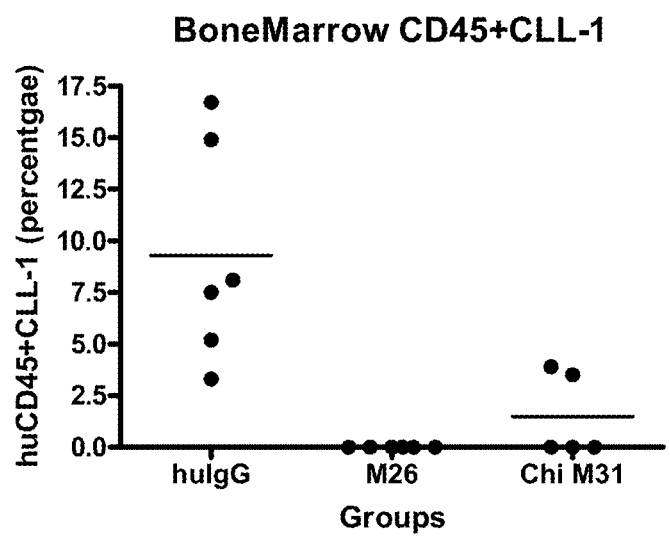

In the first study, mice were separated into three groups of 6 mice each: (1) human IgG isotype control; (2) M26; and (3) ChiM31. Mice were injected with $3 \times 10^6$ HL60 cells on Day 0. Antibody was administered at 200 ug/mouse on Days 1, 4, 7, 10, 13, 16, 19, and 22. Mice were sacrificed on Day 26. Results are shown in FIGS. 9A-9B. FIG. 9A shows that the CLL-1 antibodies significantly reduced the percentage of huCD45+CD33+ AML cells, and FIG. 9B shows that the CLL-1 antibodies significantly reduced the percentage of huCD45+ CLL-1+ AML CSCs.

Figure 10A:
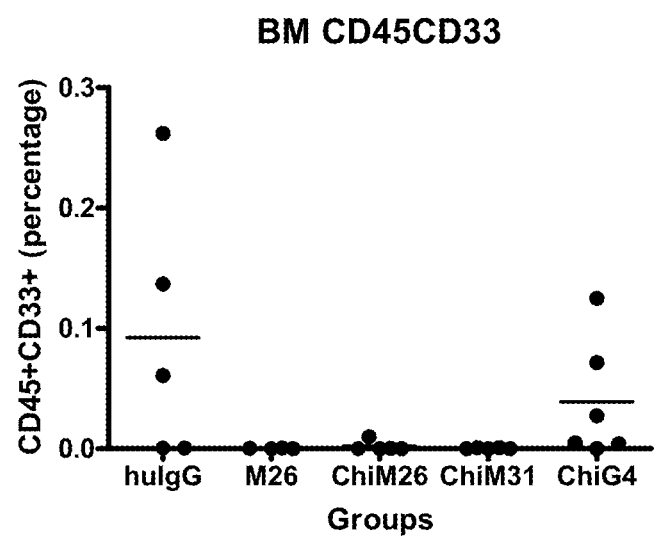
FIGS. 10A-10B show the antitumor effect of CLL-1 antibody clones in a mouse xenograft model. NOD/SCID mice were irradiated on Day −1, and on Day 0, OCI AML-5 cells were injected into the tail veins ($5\times10^6$ cells per mouse). Mice were divided into 5 groups, with n=6 mice per group: (1) huIgG control; (2) M26; (3) ChiM26; (4) ChiM31; (5) ChiG4. Mice received 8 antibody injections (200 ug) over the course of 19 days, and were sacrificed on day 24 post. Tumor burden in bone marrow was determined by FACS.
Figure 10B:
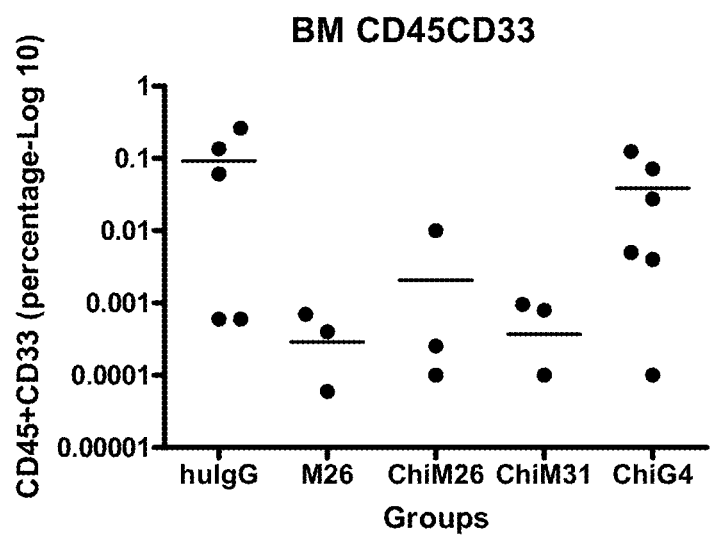

In the second study, mice were separated into five groups of 6 mice each: (1) human IgG isotype control; (2) M26; (3) ChiM26; (4) ChiM31; and (5) ChiG4. Mice were injected with $5 \times 10^6$ OCI AML-5 cells on Day 0. Antibody was administered at 200 ug/mouse on Days 1, 4, 7, 10, 13, 16, 19, and 24. Mice were sacrificed on Day 28. Results are shown in FIGS. 10A-10B. FIG. 10A shows that the CLL-1 antibodies apparently eliminated huCD45+CD33+ AML cells. A log 10 scale was used to better resolve the results, as shown in FIG. 10B.

---

What is claimed is:

1. A method of treating a myeloproliferative disorder in an individual, wherein the myeloproliferative disorder is selected from the group consisting of: acute myelogenous leukemia (AML), chronic myelogenous leukemia (CML), chronic myelomonocytic leukemia (CMML), and myelodysplastic syndrome (MDS), comprising administering to the individual a pharmaceutical composition comprising an antibody, wherein the antibody is conjugated to a cytotoxic/therapeutic compound or has the ability to induce antibody dependent cell-mediated cytotoxicity (ADCC) or complement dependent cytotoxicity (CDC) activity and wherein the antibody is selected from the group consisting of:
   an antibody comprising heavy chain complementarity determining regions (CDRs) of SEQ ID NOs:51, 59, and 67, and light chain CDRs of SEQ ID NOs:75, 83, and 91;
   an antibody comprising heavy chain CDRs of SEQ ID NOs:52, 60, and 68, and light chain CDRs of SEQ ID NOs:76, 84, and 92; and
   an antibody comprising heavy chain CDRs of SEQ ID NOs:53, 61, and 69 and light chain CDRs of SEQ ID NOs:77, 85, and 93,
   thereby treating the myeloproliferative disorder in the individual.

2. The method of claim 1, wherein the antibody is conjugated to a cytotoxic/therapeutic compound.

3. The method of claim 1, wherein the individual has been diagnosed with a myeloproliferative disorder or has undergone therapy for a myeloproliferative disorder.

4. The method of claim 1, wherein the antibody is humanized.

5. The method of claim 1, wherein the antibody is an Fv antibody fragment.

6. The method of claim 1, wherein the antibody has the ability to induce ADCC or CDC activity.

7. The method of claim 1, wherein the antibody comprises a heavy chain variable region of SEQ ID NO: 4 and a light chain variable region of SEQ ID NO: 6.

8. The method of claim 1, wherein the antibody comprises a heavy chain variable region of SEQ ID NO: 8 and a light chain variable region of SEQ ID NO: 10.

9. The method of claim 1, wherein the antibody comprises a heavy chain variable region of SEQ ID NO: 12 and a light chain variable region of SEQ ID NO: 14.

10. The method of claim 2, wherein the cytotoxic/therapeutic agent is selected from saporin, doxorubicin, daunomycin, a vinca-alkaloid, a taxoid, Maytansin, auristatin, calicheamicin, duocarmycin, and a pyrrolobenzodiazepine dimer.

11. The method of claim 2, wherein the antibody is humanized.

* * * * *